(12) United States Patent
Christensen et al.

(10) Patent No.: US 11,806,329 B2
(45) Date of Patent: *Nov. 7, 2023

(54) TREATING IRON DEFICIENCY WITH FERRIC CARBOXYMALTOSE

(71) Applicant: PHARMACOSMOS HOLDING A/S, Holbaek (DK)

(72) Inventors: Tobias Sidelmann Christensen, Roskilde (DK); Philip Schaffalitzky De Muckadell, Virum (DK); Lars Lykke Thomsen, Holte (DK); Claes Christian Strom, Rungsted (DK)

(73) Assignee: PHARMACOSMOS HOLDING A/S, Holbaek (DK)

( * ) Notice: Subject to any disclaimer, the term of this patent is extended or adjusted under 35 U.S.C. 154(b) by 134 days.

This patent is subject to a terminal disclaimer.

(21) Appl. No.: 17/187,992

(22) Filed: Mar. 1, 2021

(65) Prior Publication Data

US 2021/0290587 A1    Sep. 23, 2021

Related U.S. Application Data

(62) Division of application No. 16/822,911, filed on Mar. 18, 2020, now Pat. No. 11,020,369, which is a division of application No. PCT/EP2019/079528, filed on Oct. 29, 2019.

(30) Foreign Application Priority Data

Oct. 29, 2018  (EP) ..................................... 18203223
Oct. 31, 2018  (EP) ..................................... 18203818

(51) Int. Cl.
| A61K 31/7016 | (2006.01) |
| A61P 7/06 | (2006.01) |
| A61P 43/00 | (2006.01) |
| A61K 31/295 | (2006.01) |

(52) U.S. Cl.
CPC .............. *A61K 31/295* (2013.01); *A61P 7/06* (2018.01)

(58) Field of Classification Search
CPC ......... A61K 31/7016; A61P 7/06; A61P 43/00
USPC ......................................................... 514/53
See application file for complete search history.

(56) References Cited

U.S. PATENT DOCUMENTS 11,020,369 B2 * 6/2021 Christensen ............ G01N 33/82

FOREIGN PATENT DOCUMENTS

| CN | 104884055 A | 9/2015 |
| CN | 105873583 A | 8/2016 |
| WO | WO 2004037865 | 5/2004 |
| WO | WO 2007081744 | 7/2007 |
| WO | WO 20131334278 | 9/2013 |
| WO | WO 2016066172 | 5/2016 |

OTHER PUBLICATIONS

Bokemeyer et al. "EORTC guidelines for the use of erythropoietic proteins in anaemic patients with cancer. 2006 update." European Journal of Cancer. Jan. 1, 2007;43(2):258-70.
Van Wyck et al. "intravenous ferric carboxymaltose compared with oral iron in the treatment of postpartum anemia: a randomized controlled trial." Obstetrics a Gynecology. Aug. 1, 2007;110(2 Part 1):267-78.
Nice C. Heavy menstrual bleeding. Clinical Guideline. Jan. 2007,44(6):25-6.
Breymann et al. "Comparative efficacy and safety of intravenous ferric carboxymaltose in the treatment of postoartum iron deficiency anemia." International Journal of Gynecology & Obstetrics. Apr. 1, 2008;101(1):67-73.
Kulnigg et al. "A novel intravenous iron formulation for treatment of anemia in inflammatory bowel disease: the ferric carboxymallose (FERINJECT®) randomized controlled trial." American Journal of Gastroenterology. May 1, 2008;103(5):1182-92.
Urato AC. "Intravenous ferric carboxymaltose compared with oral iron in the treatment of postpartum anemia: a randomized controlled trial." Obstetrics & Gynecology. Sep. 1, 2008;112(3):703.
Seid et al. "Ferric carboxymaltose injection in the treatment of postpartum iron deficiency anemia: a randomized controlled clinical trial." American journal of obstetrics and gynecology. Oct. 1, 2008;199(4):435-e1.
Mak et al. "Anemia in heart failure: To treat or not to treat?" Current treatment options in cardiovascular medicine. Dec. 1, 2008;10(6):455-64.
American College of Obstetricians and Gynecologists. ACOG Practice Bulletin No. 95: anemia in pregnancy. Obstetrics and gynecology. Jul. 2008; 12(1):201-7.
Tsubakihara et al. "2008 Japanese Society for Dialysis Therapy; guidelines tor renal anemia in chronic kidney disease." Therapeutic Apheresis and Dialysis. Jun. 2010; 14(3):240-75.
Hedenus et al. "The role of iron supplementation during epoietin treatment for cancer-related anemia." Medical Oncology. Mar. 1,2009;26(1):105.
Tagboto et al. "The Efficacy of a Single Dose of intravenous Ferric Carboxymaltose (Ferinject®) on Anaemia in a Pre-Dialysis Population of Chronic Kidney Disease Patients." Journal of Renal Care. 2009 Mar. 35(1):18-23.
Macdougall et al. "Current and upcoming erythropoiesis-stimulating agents, iron products, and other novel anemia medications," Advances in chronic kidney disease. Mar. 1, 2009;16(2)117-30.

(Continued)

*Primary Examiner* — Raymond J Henley, III
(74) *Attorney, Agent, or Firm* — Robin L. Teskin; Baker, Donelson, Bearman, Caldwell & Berkowitz PC

(57) ABSTRACT

The present invention relates to the field of treating iron deficiency with IV iron carbohydrate complexes such ferric carboxymaltose, monitoring or identifying subjects to determine their eligibility for being administered said IV iron carbohydrate complexes, and combining said IV iron carbohydrate complexes with additional drugs in order to mitigate or reduce side effects induced by said IV iron carbohydrate complexes.

34 Claims, 15 Drawing Sheets

(56) References Cited

OTHER PUBLICATIONS

Lyseng-Williamson et al. "Ferric carboxymallose: a review of its use in iron-deficiency anaemia Drugs." 2009;69(6):739-56.
Van Wyck et al. "Blood Management: Large-dose intravenous ferric carboxymaltose injection for iron deficiency anemia in heavy uterine bleeding: a randomized, controlled trial." Transfusion. Dec. 2009,49(12):2719-28.
López RM, Aladrén BS, Garcia FG, Use of agents stimulating erythropoiesis in digestive diseases. World Journal of Gastroenterology: WJG. Oct. 7, 2009;15(37):4675.
Muñoz et al. "Intravenous iron in inflammatory bowel disease" World J Gastroenterol. Oct. 7, 2009;15(37):4666-74.
Anker et ai. "Rationale and design cf Ferinject® Assessment In patients with IRon deficiency and chronic Heart Pailure (FAIR-HF) study; a randomized, placebo-controlled study of intravenous iron supplementation in patients with and without anaemia." European journal of heart failure. Nov. 2009;11(11):1084-91.
Pugh-Clarke et al, "An evidence-based approach to anaemia management In predialysis chronic kidney disease." J Ren Care. Dec. 2009;35 Suppl 2:29-31.
Macdougall IC. "Evolution of iv iron compounds over the last century." J Ren Care. Dec. 2009;35 Suppl 2:8-13.
Anker et al. "Ferric carboxymaltose in patients with heart failure and iron deficiency." N Engl J Med. Dec. 17, 2009;361(25):2436-48.
Dec et al. "Anemia and iron deficiency—new therapeutic targets in heart failure?" N Engl J Med. Dec. 17, 2009:361(25):2475-7.
Muñoz et al. "Iron deficiency and anaemia in bariatric surgical patients: causes, diagnosis and proper management" Nutr Hosp. Nov.-Dec. 2009;24(6):640-54.
Royal College of Obstetricians and Gynaecologists "Prevention and Management of Postpartum Haemorrhage" May 2009;52:1-24.
Bailie et al. "Safety and tolerability of intravenous ferric carboxymaltose in patients with iron deficiency anemia." Hemodial Int. Jan. 2010:14(1):47-54.
Macdougall IC. "Iron supplementation in the non-dialysis chronic kidney disease (ND-CKD) patient: oral or intravenous?" Current medical research and opinion, Feb. 1, 2010;26(2):473-82.
Covin A, Mircescu G. "The safety and efficacy of intravenous ferric carboxymaltose in anaemic patients undergoing haemodialysis: a multi-centre, open-label, clinical study" Nephrol Dial Transplant. Aug. 2010;25(8):2722-30.
Kociol et al. "Ferric carboxymaltose improved symptoms and quality of life in patients with chronic heart failure and iron deficiency" Ann Intern Med. Apr. 20, 2010;152(8):JC4-5.
Jelani et al. "Iron in heart failure: friend or foe?" Carr Heart Fail Rep. Jun. 2010;7(2):49-51.
Szczech et al. "Randomized evaluation of efficacy and safety of ferric carboxymaltose in patients with iron deficiency anaemia and impaired renal function (REPAIR-IDA): rationale and study design" Nephrol Dial Transplant, Jul. 2010,25(7):2368-75.
Toblii et al, "Comparison of the renal, cardiovascular and hepatic toxicity data of original intravenous iron compounds" Nephrol Dial Transplant. Nov. 2010;25(11):3631-40.
Breymann et ai. "Diagnosis and treatment of iron-deficiency anaemia during pregnancy and postpartum" Arch Gynecol Obstet. Nov. 2010;282(5):577-80.
Qunibi. "The efficacy and safety of current intravenous iron preparations for the management of iron-deficiency anaemia: a review" Arzneimittelforschung. 2010;60(6a):399-412. doi: 10.1055/s-0031-1296304.
Bailie GR. "Efficacy and safety of ferric carboxymaltose in correcting iron-deficiency anemia: a review of randomized controlled trials across different indications." Arzneimittelforschung. 2010;60(6a):386-98.
Geisser et al. "Pharmacodynamics and safety of ferric carboxymaltose: a multiple-dose study in patients with iron-deficiency anaemia secondary to a gastrointestinal disorder" Arzneimittelforschung, 2010;60(6a):373-85.
Geisser et al. "Pharmacokinetics, safety and tolerability of intravenous feme carboxymaltose: a dose-escalation study in volunteers with mild iron-deficiency anaemia" Arzneimittelforschung, 2010;60(6a)362-72.
Malek A. "in vitro studies of ferric carboxymalfose on placental permeability using the dual perfusion model of human placenta" Arzneimittelforschung. 2010,60(a)354-61.
Funk et al. "The new generation of intravenous iron: chemistry, pharmacology, and toxicology of ferric carboxymallose" Arzneimittelforschung. 2010,60(6a):345-53.
Marx JJ. "Progress in intravenous iron treatment" Arzneimittelforschung. 2010;60(6a):341-4.
Mani et al. "Severe hypophosphatemia after intravenous administration of iron carboxymalfose in a stable renal transplant recipient" Transplantation. Oct. 15, 2010;90(7):804-5.
Bager et al. "The health care cost of intravenous iron treatment in IBD patients depends on the economic evaluation perspective" J Crohns Colitis. Oct. 2010,4(4):427-30.
Auerbach et al. "Clinical use of intravenous iron: administration, efficacy, and safety" Hematology Am Sec Hematol Educ Program. 2010;2010:338-47.
Marret et al; on behalf of the College National des Gynecologues et Obstetriclens Francais (CNGOF) "Clinical practice guidelines on menorrhagia: management of abnormal uterine bleeding before menopause" Eur J Obstet Gynecol Reprod Biol 2010, 152 (2): 133-137.
Bross, Soch & Smith-Knuppel Anemia in Older Persons Am Fam Physician 2010; 82 (5): 480-487.
Pavord S, Hunt B, editors. Ths obstetric hematology manual. Cambridge University Press; Feb. 8, 2018.
Qunibi et al. "A randomized controlled trial comparing intravenous ferric carboxymaltose with oral iron for treatment of Iron deficiency anaemia of non-dialysis-dependent chronic kidney disease patients" Nephrol Dial Transplant May 2011;26(5):1599-607.
Von Haehling et al. "Anemia in heart fallure: an overview of current concepts" Future Cardiol. Jan. 2011;7(1):119-29.
Gozzard D. "When is high-dose intravenous iron repletion needed? Assessing new treatment options" Drug Des Devel Ther. Jan. 20, 2011;5:51-60.
Jahn et al. "A comparative study of the physicochemical properties of iron isomaltoside 1000 (Monofer), a new intravenous iron preparation and its clinical implications." Eur J Pharm Biophann. Aug. 2011;78(3):480-91.
Bhandari S. "A hospital-based cost minimization study of the potential financial impact on the UK health care system of introduction of iron isomaltoside 1000" Ther Clin Risk Manag. 2011;7:103-13.
Cowie et al. "Clinical perspective: iron replacement therapy in chronic heart failure" Int J Clin Pract. Jun. 2011;65(6)645-8.
Locatelli et al. "New erythropoiesis-stimulating agents and new iron formulations" Contrib Nephrol, 2011;171:255-260.
Evstatiev et al. "FERGI Study Group, FERGIcor, a randomized controlled trial on ferric carboxymaltose for iron deficiency anemia in inflammatory bowel disease" Gastroenterology. Sep. 2011;141(3):846-853.e1-2.
Gomollón et al. "IBD. Intravenous Iron in IBD—what's the best preparation?" Nat Rev Gastroenterol Hepatol. Jul. 26, 2011;8(9):477-8.
Bisbe et al. "Anaemia Working Group España. A multicentre comparative study on ths efficacy of intravenous ferric carboxymaltose and iron sucrose for correcting preoperative anaemia in patients undergoing major elective surgery" Br J Anaesth. Sep. 2011;107(3):477-8.
Toblii at al. "Assessment of the extent of oxidative stress induced by intravenous ferumoxytol, ferric carboxymaltose, iron sucrose and iron dextran in a nonclinical model" Arzneimittelforschung. 2011;61(7):399-410.
Moore et al. "Meta-analysis of efficacy and safety of intravenous ferric camoxymaltose (Ferinject) from clinical trial reports and published trial data" BMC Blood Disord. Sep. 24, 2011;11:4.
Alien et al. "Clinical efficacy and safety of IV ferric carboxymaltose (FCM) treatment of RLS: a multi-centred, placebo-controlled preliminary clinical trial" Sleep Med. Oct. 2011;12(9):906-13.

(56) References Cited

OTHER PUBLICATIONS

Bhandari S. "Update of a comparative analysis of cost minimization following the introduction of newly available intravenous iron therapies in hospital practice" Ther Clin Risk Manag. 2011;7:501-9.
Bhandari S. "Beyond efficacy and safety-trie need for convenient and cost-effective iron therapy in health care" NDT Plus. Jun. 2011;4(Suppl 1):i4-i19.
Ferraris et al. "2011 update to the Society of Thoracic Surgeons and the Society of Cardiovascular Anesthesiologists blood conservation clinical practice guidelines." The Annals of thoracic surgery. Mar. 1, 2011;91(3):944-82.
Who V. Haemoglobin concentrations for the diagnosis of anaemia and assessment of severity. Geneva: Vitamin and Mineral Nutrition Information System, WHO. Aug. 22, 2011.
Von Haehling et ai, "Anemia in chronic heart failure: can we treat? What to treat?" Heart Fail Rev. Mar. 2012;17(2);203-10.
Luporsi et al. "Evaluation of cost savings with ferric carboxymaltose in anemia treatment through its impact on erythropoiesis-stimulating agents and blood transfusion: French healthcare payer perspective" J Med Econ. 2012;15(2):225-32.
Hönemann et al, "Anaemia tolerance, bridging with intravenous ferric carboxymaltose in a patient with acute post-haemorrhagic anaemia" Br J Anaesth. Jan. 2012; 108(1):167-8.
Beigel et al. "Iron status and analysis of efficacy and safety of ferric carboxymaltose treatment in patterns with inflammatory bowel disease." Digestion. 2012;85(1):47-54.
Martin-Malo et ai. "Effects of intravenous iron on mononuclear cells during the haemodialysis session." Nephrol Dial Transplant. Jun. 2012;27(6)2465-71.
Bernabeu-Wittel et al. "PAHFRAC-01 investigators. Ferric carboxymaltose with or without erythropoietin for the prevention of red-cell transfusions in the perioperative period of osteoporotic hip fractures: a randomized contolled trial." The PAHFRAC-01 project BMC Musculoskelet Disord Feb. 21, 2012,13:27.
Maretty et al. "Intravenous ferric carboxy maltose accelerates erythropoietic recovery from experimental malarial anemia." J infect Dis. Apr. 1, 2012;205(7):1173-7.
Muñoz et al. "Ferric carboxymaltose for the treatment of iron-deficiency anemia." Expert opinion on pharmacotherapy. Apr. 1, 2012;13(6):907-21.
Kulnigg-Dabsch et al. "Effect of Iron therapy on platelet counts in patients with inflammatory bowel disease-associated anemia" PLoS One. 2012;7(4):e34520.
Hornyak el al. "Investigating the response io intravenous iron in restless legs syndrome: an observational study." Sleep Med. Jun. 2012;13(6)732-5.
Heming et al. "Efficacy and toxicity of intravenous iron in a mouse model of critical care anemia." Crit Care Med. Jul. 2012;40(7):2141-8.
Pragoulakis et al. "Economic evaluation of intravenous iron ireai-ments in the management of anemia patients In Greece." ClinicoEconomics and outcomes research: CEOR. 2012;4:127.
Prabhu et al. "Maximizing the erythropoietin response: iron strategies." Contrib Nephrol. 2012;178:95-99.
Gutzwiller et al. "Health economic assessment of ferric carboxymaltose in patients witn iron deficiency and chronic heart failure based on the FAIR-HF trial: an analysis for the UK" Eur J Heart Fail. Jul. 2012; 14(7):782-90.
Shander et al. "Resurrecting the Iron age" Crit Care Med. Jul. 2012;40(7):2252-3.
Hoo et al. "Intravenous iron among cystic fibrosis patients." J Cyst Fibres. Dec. 2012;11(6):560-2.
Pfenniger et al. "Safety and efficacy of high-dose intravenous iron carboxymaltose vs. iron sucrose for treatment of postpartum anemia." J Perinat Med. Apr. 2, 2012;40(4):397-402.
Christoph et al. "Intravenous iron treatment in pregnancy: comparison of high-dose ferric carboxymaltose vs. iron sucrose." J Perinat Med. May 13, 2012;40(5):469-74.

Barish et al. "Safety and Efficacy of Intravenous Ferric Carboxymaltose (750mg) in the Treatment of Iron Deficiency Anemia: Two Randomized, Controlled Trials," Anemia. 2012:2012:172104.
Calvet et al. "Cost-minimization analysis favours intravenous ferric carboxymaltose over ferric sucrose for the ambulatory treatment of severe iron deficiency." PLoS One. 2012;7(9):e45604.
Wilt et al. "Treatment for Restless Legs Syndrome Rockville (MD)" Agency for Healthcare Research and Quality (US); Nov. 2012. Report No. 12(13)-EHC147-EF.
Muñoz et al. "Perioperative intravenous iron: an upfront therapy for treating anaemia and reducing transfusion requirements." Nutr Hosp. Nov.-Dec. 2012;27(6): 1817-36.
Dilion et ah "Comparative efficacy of three forms of parenteral iron." J Blood Transfus. 2012:2012:473514.
Myers et al. "Comparative afficacy and safety of intravenous ferric carboxymallose (Ferinject) and Iron (III) hydroxide dextran (Cosmofer) in pregnancy." Obstet Med. Sep. 2012; 5(3);105-7.
Kidney Disease: improving Global Outcomes (KDIGO) Anemia Work Group. KDIGO clinical practise guideline for anemia in chronic kidney disease. Kidney Int Suppl. 2012;2(4):279-335.
Authority NB. Patient blood management guidelines: module 2. perioperative. Canberra, Australia: National Blood Authority (NBA). 2012.
Comin-Colet et al. "The effect of intravenous ferric carbexymaltose on health-related quality of life in patients with chronic heart failure and iron deficiency: a subanalysis of the FAIR-HF study." Eur Heart J. Jan. 2013;34(1):30-8.
Reinisch et al. "State of the iron: how to diagnose and efficiently treat iron deficiency anemia in inflammatory bowel disease." J Crohns Colitis. Jul. 2013;7(6):429-40.
Wilson et al. "An analysis of the health service efficiency and patient experience with two different intravenous iron preparations in a UK anaemia clinic." J Med Econ. 2013:16(1)108-14.
Steinmetz et al. "Clinical experience with ferric carboxymallose in the treatment of cancer-and chemotherapy-associated anaemia." Ann Oncol. Feb. 2013;24(2):475-482.
Evstatiev et al. "FERGI Study Group. Ferric carboxymaltose prevents recurrence of anemia in patients with Inflammatory bowel disease," Clin Gastroenterol Hepatol. Mar. 2013;11(3):289-77.
Charytan et al. "Intravenous ferric carboxymaltose versus standard medical care in the treatment of iron deficiency anemia in patients with chronic kidney disease: a randomized, active-controlled, multi-center study." Nephrol Dial Transplant. Apr. 2013;28(4):953-64.
Gomollón et al. "Intravenous iron in inflammatory bowel diseases." Curr Opin Gastroenterol. Mar. 2013;29(2):201-7.
Macdougall et al. "Use of intravenous iron supplementation in chronic kidney disease: an update" Iran J Kidney Dis. Jan. 2013;7(1):9-22.
Bregman et al. "Hepcidin levels predict nonresponsiveness to oral iron therapy in patients with iron deficiency anemia." Am J Hematol. Feb. 2013;88(2):97-101.
Schatz et al, "Iron deficiency and its management in patients undergoing lipoprotein apheresis. Comparison of two parenteral iron formulations" Atheroscler Suppl. Jan. 2013; 14(1)115-22.
Wolf et al. "Effects of iron deficiency anemia and its treatment on fibroblast growth factor 23 and phosphate homeostasis in women." J Bone Miner Res. Aug. 2013 ;28(8): 1793-803.
Malone et al. "Comparative review of the safety and efficacy of ferric carboxymaltose versus standard medical care for the treatment of iron deficiency anemia in bariatric and gastric surgery patients." Obes Surg. Sep. 2013;23(9):1413-20.
Polin et al. "iron deficiency from diagnosis to treatment" Dig Liver Dis. Oct. 2013;45(10):803-9.
Prats et al. "Acute and sub-acute effect of ferric carboxymaltose on inflammation and adhesion molecules in patients with predialysis chronic renal failure" Nefroiogia. 2013;33(3):355-61.
Van Craenenbroeck et al. "The effect of intravenous ferric carboxymalfose on red cell distribution width; a subanalysis of the FAIR-HF study" Eur J Heart Fail. Jul. 2013;15(7):756-62.
Kulnigg-Dabsch et al. "Iron deficiency generates secondary thrombocytosis and platelet activation in IBD: the randomised, controlled thromboVIT trial" Inflamm Bowel Dis. Jul. 2013:19(8):1609-16.

(56) References Cited

OTHER PUBLICATIONS

Howard st al. "Supplementation of iron in pulmonary hypertension: Rationale and design of a phase II clinical trial in idiopathic pulmonary arterial hypertension" Pulm Circ. Jan. 2013:3(1):100-7.

Bailie et al. "Oxidative effect of several Intravenous iron complexes in the rat" Biometals. Jun. 2013;26(3):473-8.

Janus et al. "Administration of intravenous iron complexes on implantable central venous access port in cancer patients in France: the FERPAC survey" Support Care Cancer. Oct. 2013;21(10):2743-8. Epub May 29, 2013.

Filippatos et al. "Intravenous ferric carboxymaltose in iron-deficient chronic heart failure patients with and without anaemia: a subanaiysis of the FAIR-HF trial" Eur J Heart Fail. Nov. 2013;15(11):1267-76.

Weiss G. "Monitoring iron therapy in chronic heart failure" Eur J Heart Fail. Jul. 2013;15(7):711-2.

Trippel et al. "The role of micronutrients and macronutrients in patients hospitalized far heart failure" Heart Fail Clin. Jul. 2013,9(3):345-57, vii.

Gutzwiller et al. "Determinants of quality of life of patients with heart failure and iron deficiency treated with ferric carboxymaltose: FAIR-HF sub-analysis" Int J Cardiol. Oct. 9, 2013;168(4):3878-83.

Befrits et al. "Anemia and Iron deficiency in inflammatory bowel disease; an open, prospective, observational study on diagnosis, treatment with feme carboxymaltose and quality of life" Scand J Gastroenterol. Sep. 2013,48(9):1 027-32.

Prats et a. "Effect of ferric carboxymaltose on serum phosphate and C-terminal FGF23 levels in non-dialysis chronic kidney disease patients: post-hoc analysis of a prospective study" BMC Nephrol. Jul. 31, 2013;14:167.

Thompson CA. "Ferric carboxymaltose approved for iron deficiency anemia" Am J Health Syst Pharm. Sep. 1, 2013;70(17):1458.

Radia et al. "Anemia management: development of a rapidaccess anemia and intravenous iron service" Risk Manag Healthc Policy. Aug. 6, 2013:6:13-22.

Fütterer et al. "Structural characterization of iron oxide/hydroxide nanoparticles in nine different parenteral drugs for the treatment of iron deficency anaemia by electron diffraction (ED) and X-ray powder diffraction (XRPD)" J Pharm Biomed Anal. Dec. 2013;86:151-60.

Koskenkorva-Frank et al. "The complex interplay of iron metabolism, reactive oxygen species, and reactive nitrogen species; insights Into the potential of various iron therapies to induce oxidative and nltrosative stress" Free Radic Biol Med. Dec. 2013;65:1174-1194.

Hussain et al. "Direct Comparison of the Safety and Efficacy of Ferric Carboxymaltose versus Iron Dextran in Patients with Iron Deficiency Anemia" Anemia. 2013;2013:169107.

Gomollón et al. "Current management of iron deficiency anemia in inflammatory bowel diseases: a practical guide" Drugs. Nov. 2013;73(16):1761-70.

Gravesen et al. "High dose intravenous iron, mineral homeostasis and intact FGF23 in normal and uremic rats" BMC Nephrol Dec. 27, 2013:14:281.

Goldenberg MM. "Pharmaceutical approval update" P T. Oct. 2013;38(10):603-36.

Cada et al. "Doxylamine succinate/pyridoxine hydrochloride" Hosp Pharm. Oct. 2013,48(9):762-6.

Van Assche et al. "Second European evidence-based consensus on the diagnosis and management of ulcerative colitis Part 3: Special situations" J Crohns Colitis 2013; 7(1): 1-33.

Short et al. "iron Deliciency Anemia. Evaluation and Management" Am Fam Physician 2013; 87 (2): 98-104.

Minck et al. "Patient btood management The GP's guide" Aust Fam Physician 2013; 42 (5), 291-297.

European Renal Best Practice (ERBP) group Kidney Disease: Improving Global Outcomes guidelines on anaemia management in chronic kidney disease: a European Renal Best Practice position statement Nephrol Dial Transplant 2013; 28: 1346-1359.

Onken et al. "A mullicenter, randomized, active-controlled study to investigate the efficacy and safety of Intravenous ferric carboxymaltose in patients with iron deficiency anemia" Transfusion, Feb. 2014:54(2):306-15.

Garvican et al. "Intravenous iron supplementation in distance runners with low or suboptimal ferritin" Med Sci Sports Exerc. Feb. 2014;46(2):376-85.

Onken et al. "Feme carboxymaltose in patients with iron-deficiency anemia and impaired renal function: the REPAIR-IDA trial" Nephrol Dial Transplant. Apr. 2014;29(4):833-42.

Brock et al. "Budget impact of parenteral iron treatment of iron deficiency: methodological issues raised by using real-life data" Eur J Health Econ. Dec. 2014;15(9):907-16.

Muñoz et al. "Cost of post-operative intravenous iron therapy in total lower limb arthroplasty: a retrospective, matched cohort study" Blood Transfus, Jan. 2014;12(1):40-9.

Macdougall et al. "The FIND-CKD Study Investigators The FIND-CKD study—a randomized controlled trial of intravenous iron versus oral iron in non-dialysis chronic kidney disease patients: background and rationale" Nephrol Dial Transplant. Apr. 2014;29(4)843-50.

Macdougail IC. "Intravenous iron theraoy in non-dialysis CKD patients" Nephrol Dial Transplant. Apr. 2014,29(4):717-20.

Larson et al. "Update on intravenous iron choices" Curr Opin Nephrol Hypertens. Mar. 2014;23(2):186-91.

Cada et al. "Ferric carboxymaltose" Hosp Pharm. Jan. 2014;49(1):52-9.

Blazevic et al. "Severe hypophosphataemia after intravenous iron administration" Neth J Med. Jan. 2014;72(1):49-53.

Barea Mendoza et al. [Hypophosphatemia, a poorly known adverse reaction of intravenous use of iron] Med Clin (Barc). Sep. 15, 2014;143(5):284-5.

Fell et al. "Distinct immunologic affects of different intravenous iron preparations on monocytes" Nephrol Dial Transplant. Apr. 2014;29(4):809-22.

Fierz et al. "Severe and prolonged hypophosphatemia after intravenous iron administration in a malnourished patient" Eur J Clin Nutr. Apr. 2014;68(4):531-3.

Merino et al. [Intravenous ferric carboxy maltose for the treatment of anemia in chronic renal disease] Rev Clin Esp (Barc). Jun.-Jul. 2014;214(5):282-3. doi: 10.1016/j.rce.2014.01.010. Epub Feb. 26, 2014.

Peck et al. "Medical therapy versus implantable cardioverter-defibrillator in preventing sudden cardiac death in patients with left ventricular systolic dysfunction and heart failure: a meta-analysis of > 35,000 patients" Int J Cardiol. May 1, 2014;173(2):197-203.

Froessler et al. "Intravenous ferric carboxymaltose for anaemia in pregnancy" BMC Pregnancy Childbirth. Mar. 25, 2014;14:115.

Bregman ©tai. "Experience with intravenous ferric carboxymaltose in patients with iron deficiency anemia" Ther Adv Hematoi. Apr. 2014;5(2):48-60.

Reim D, Kim YW, Nam BH, Kim MJ, Yook JH, Park YK, Roh SH. Yu WS. Bae Jm. FAIRY, a randomized controlled patient-blind phase III study to compare the efficacy and safety of intravenous ferric carboxymaltose (FerinjectÅ®) to placebo in patients with acute isovolemic anemia after gastrectomy—study protocol for a randomized controlled trial Trials. Apr. 5, 2014;15:111. doi: 10.1180/1745-6215-15-111.

Blumenstein et ai. "Current practice in the diagnosis and management, of IBD-associated anaemia and iron decency in Germany: the German AnaemiBD Study" J Crohns Colitis. Oct. 2014;8(10):1308-14.

Herfs et al. "Treatment of Iron Deficiency with or without Anaemia with Intravenous Ferric Carboxymaltose in Gynaecological Practices—A Non-Interventional Study" Geburtshilfe Frauenheilkd. Jan. 2014;74(1):81-88.

Favral et al. "Evaluation of a single dose of ferric carbexymaltose in fatigued, iron-deficient women—PREFER a randomized, placebo-controlled study" PLoS One. Apr. 21, 2014:9(4).e04217.

Bisbe ©t ai. "Randomized trial comparing ferric carboxymaltose vs oral ferrous glycine sulphate for postoperative anaemia after total knee arthroplasty" Br J Anaesth. Sep. 2014;113(3):402-9.

(56) References Cited

OTHER PUBLICATIONS

Toblii et al. "Ferric carboxymaltose-mediated attenuation of Doxorubicin-induced cardiotoxicity in an iron deficiency rat model" Chemother Res Pract. 2014;2014:570241.
Viethen et al. "Ferric carboxymallose improves exercise capacity and quality of life in patients with pulmonary arterial hypertension and iron deficiency, a pilot study" Int J Cardiol. Aug. 1, 2014;175(2):233-9.
Maodougall et al. "FIND-CKD Study Investigators. FIND-CKD: a randomized trial of intravenous ferric carboxymaltose versus oral iron in patients with chronic kidney disease and iron deficiency anaemia" Nephrol Dial Transplant. Nov. 2014;29(11):2075-84.
Keeler et al. "The feasibility and clinical efficacy of intravenous iron administration for preoperative anaemia in patients with colorectal cancel" Colorectal Dis. Oct. 2014;16(10)794-800.
Bircher et al. "Hypersensitivity from intravenous iron products Immunol" Allergy Clin North Am. Aug. 2014;34(3):707-23, x-xi.
Rineau et al. "Ferric carboxymaltose increases epoetin-α response and prevents iron deficiency before elective orthopaedic surgery" Br J Anaesth. Aug. 2014;113(2):296-8.
Woods at al. "Four weeks of IV iron supplementation reduces perceived fatigue and mood disturbance in distance runners" PLoS One. Sep. 23, 2014;9(9):e108042.
Lim et al. "Cost-utility of ferric carboxymallose (Ferinject®) for iron-deficiency anemia patients with chronic heart failure in South Korea" Cost Eff Resour Alloc. Sep. 10, 2014;12:19.
Laase el al. "Effectiveness and safely of ferric carboxymalfose treatment in children and adolescents with inflamomatory bowel disease and other gastrointestinal diseases" BMC Gastroenterol. Oct. 17, 2014:14:184.
Hedenus et al. "Intravenous iron alone resolves anemia in patients with functional iron deficiency and lymphoid malignancies undergoing chemotherapy" Med Oncol. Dec. 2014 ;31(12):302.
Becurzi et al. "Long-term efficacy of postoarturn intravenous iron therapy" Biomed Res Int. 2014:2014:815437.
Litton et al. "Australian and New Zealand Intensive Care Society Clinical Trials Group. The IRONMAN trial: a protocol for a multicentre randomised placebo-controlled trial of intravenous iron in intensive care unit patients with anaemia" Crit Care Resusc. Dec. 2014:16(4):285-90.
Thanusubramanian et al. "Adverse reactions of ferric carboxymaltose" J Clin Diagn Res. Oct. 2014:8(10):HD01-2.
Vandemergel et al. "Potentially life-threatening phosphate diabetes induced by ferric carboxymaltose injection: a case report and review of the literature" Case Rep Endocrinol. 2014;2014:843689.
Toblii et al. "Optimizing iron delivery in the management of anemia: patient considerations and the role of ferric carboxymaltose" Drug Des Devel Ther. Dec. 11, 2014;8:2475-91.
Deho et al. "Health Economic Evaluation Comparing Iv Iron Feme Carboxymaltose, Iron Sucrose and Blood Transfusion For Treatment of Patients with Iron Deficiency Anemia (Ida) in Singapore" Value Health. Nov. 2014;17(7):A784.
Myonas et al. Economic Evaluation of Ferric Carbexymaltose in Patients With Chronic Heart Failure and Iron Deficiency: An Analysis for Greece Based on Fair-Hf Trial Value Health. Nov. 2014;17(7):A486.
Ponikowski et al. "Rationale and design of the CONFIRN-HF study: a double-blind, randomized, placebo-controlled study to assess the effects of intravenous ferric carboxymaltose on functional capacity in patients with chronic heart failure and iron deficiency" ESC Heart Fail. Sep. 1, 2014;1(1):52-58.
Lothian NHS iron Therapy (intravenous) in pregnancy and the postnatal period: Maternity Services Lothian—Guidelines; 2014.
"Guideline for the management of anaemia in pregnancy and postnatalty." South West RTC Management of Anaemia in Pregnancy, Apr. 2014.
Toblii et al. "Nitrosative Stress and Apoptosis by Intravenous Ferumoxytol, Iron isomaltoside 1000, Iron Dextran, Iron Sucrose, and Ferric Carboxymaltose in a Nonclinical Model" Drug Res (Stuttg). Jul. 2015;65(7):354-60.

Ponikowski et al. "CONRIRM-HF Investigators. Beneficial effects of long-term intravenous iron therapy with ferric carboxymaltose in patients with symptomatic heart failure and iron deficiency" Eur Heart J. Mar. 14, 2015,36(11):657-68.
Kuster et al. "Treatment of iron deficiency with intravenous ferric carboxymalfose in general practice: a retrospective database study" J Clin Med Res. Jan. 2015;7(1):37-40.
Keating, GM. "Ferric carbexymaltose: a review of its use in iron deficiency" Drugs. Jan. 2015;75(1):101-27.
Iqbal et al. "Clinical significance of C-reactive protein levels in predicting responsiveness to iron therapy in patients with inflammatory bowel disease and iron deficiency anemia" Dig Dis Sci. May 2015:60(6):1375-81.
Sáchez et al., [Intravenous ferric carboxymaltose-assoclated hypophosphatemia in patients with iron deficiency anemia. A common side effect] Med Clin (Barc) Aug. 7, 2015:145(3):108-11.
McDonagh et al. "Iron therapy for the treatment of iron deficiency in chronlo heart failure: intravenous or oral?" Ear J Heart Fail. Mar. 2015;17(3)248-62.
Comin-Colet et al. "A Cost-effectiveness Analysis of Ferric Carbexymaltose in Patients With Iron Deficiency and Chronic Heart Failure in Spain" Rev Esp Cardiol (Engl Ed). Oct. 2015;68(10):846-51.
Rathod et al. "Ferric carboxymaltose: A revolution in the treatment of postpartum anemia In Indian women" Int J Appl Basic Med Res. Jan.-Apr. 2015;5(1):25-30.
Ponikowski et ai, "FAIR-HF Trial Investigators. The impact of intravenous ferric carboxymallose on renal function: an analysis of the FAIR-HF study" Eur J Heart Fail. 2015 Mar. 17(3):329-39.
Cotroneg et al. "Iron homeostasis and pulmonary hypertension: iron deficiency leads to pulmonary vascular remodeling in the rat" Circ Res. May 8, 2015;116(10);1680-90.
Hoimarcher et al. "Cost-effectiveness analysis of ferric carboxymalfose in iron-deficient patients with chronic heart failure in Sweden" J Med Econ. 2015;18(7):492-501.
Hofmarcher et al. "Cost-effectiveness analysis of ferric carboxymaltose in iron-deficient patients with chronic heart failure in Sweden" J Med Econ. 2015;18(7):492-501.
Neiser et al. "Physico-chemical properties of the new generation IV iron preparations ferumoxytol, iron isomaltoside 1000 and ferric carboxymaltose" Biometals. Aug. 2015;28(4):615-35.
McKavanagh et al. "A Review of the Key Clinical Trials of 2014" Cardiol Ther. Jun. 2015;4(1):5-23.
Mattinson et al. "Spontaneous bacterial peritonitis in a patient with anorexia nervosa with profound zinc and iron deficiency," Am J Med. Aug. 2015;128(8):e1-2.
Toblii et al. "Switching patients with non-dialysis chronic kidney disease from oral iron to intravenous ferric carboxymaltose: effects on erythropoiesis-stimulating agent requirements, costs, hemoglobin and iron status" PLoS One. Apr. 30, 2015;10(4):e0125528.
Schatz et al., "TIDILAP: Treatment of Iron deficiency in lipoprotein apheresis patients—A prospective observational multi-center cohort study comparing efficacy, safety and tolerability of ferric gluconate with ferric carboxymaltose" Atheroscler Seppl. May 2015;18:199-208.
Bridgeman et al. "Drugs for urologic disorders" Nursing. Jun. 2015;45(0):68.
Connor et al. "Comparative evaluation of nephrotoxicity and management by macrophages of intravenous pharmaceutical iron formulations." PLoS One. May 14, 2015;10(5):e0125272.
Hardy et al. "Intravenous iron administration and hypophosphatemia in clinical practice" Int J Rheumatol. 2015;2015:468675.
Cortes et al. "Safety of ferric carboxymallose immediately after infliximab administration, in a single session, in inflammatory bowel disease patients with iron deficiency: a pilot study" PLoS One. May 26, 2015;10(5):e0128156.
Richards ei ai. "PREVENTT: preoperative intravenous iron to treat anaemia in major surgery: study protocol for a randomised controlled trial" Trials. Jun 4, 2015:254, doi: 10.1186/s13063-015-0774-2.

(56) References Cited

OTHER PUBLICATIONS

Borstiap et al. "Multicentre randomized controlled trial comparing ferric(III)carboxymaltose infusion with oral iron supplementation in the treatment of preoperative anaemia in colorectal cancer patients" BMC Surg. Jun. 28, 2015;15:78.

Vikrant et al. "The safety and efficacy of high dose ferric carboxymaltose in patients with chronic kidney disease: A single center study" Indian J Nephrol. Jul.-Aug. 2015;25(4) :213-21.

Bach et al. "Efficacy and Safety of Intravenous Ferric Carboxymaltose in Geriatric Inpatients at a German Tertiary University Teaching Hospital: A Retrospective Observational Cohort" Study of Clinical Practice Anemia. 2015;2015:647930.

Koch el ai, "Intravenous iron Therapy in Patients with iron Deficiency Anemia: Dosing Considerations" Anemia. 2015;2015:763576.

Minutolo et al. [Clinical experience with ferric carboxymaltose in non-dialysis chronic kidney disease] G Ital Nefrol, Sep-Oct. 2015;32(5):gin/32.5.11 English Abstract.

Schneider et al. "Open-label study of the efficacy and safety of intravenous ferric carboxymalfose in pregnant women with restless legs syndrome" Sleep Med. Nov. 2015;16(11):1342-1347.

Rottembourg et al. [Use of intravenous iron supplementation in chronic kidney disease: Interests, limits, and recommendations for a better practice] Nephrol Ther. Dec. 2015;11(7):531-42 doi: 10.1016/j.nephro.2015.04.009. Epub Oct. 20, 2015. English Abstract.

Brunetta et al. "Severe Acute Anemia After Liver Transplantation in an Elderly Jehovah's Witness Treated With High-dose Erythropoietin and Ferric Carboxymaltose. A Case Report" Transplant Proc. Oct. 2015;47(8):2548-51.

Friedrisch et al. "Intravenous ferric carboxymaltose for the treatment of iron deficiency anemia" Rev Bras Hematol Hemoter. Nov.-Dec. 2015;37(6):400-5.

Pels et al. "Safety and Efficacy of Ferric Cardoxymaltose in Anemic Pregnant Women: A Retrospective Case Control Study" Obstet Gynecol Int. 2015;2015:728952.

Toblli et al. "The Induction of Oxidative/Nitrosative Stress, Inflammation, and Apoptosis by a Ferric Carboxymalfose Copy Compared to Iron Sucrose in a Non-Clinical Model" J Clin Diagn Res. Dec. 2015;9(12):FF08-12.

Sobrado et al. "Treatment of Anemia and Improvement of Quality of Life Among Patients With Crohn's Disease: experience using ferric carboxymaltose" Arq Gastroenterol. Dec. 2015,52(4):255-9.

Nores et al. "the Efficacy of IV Ferric Cardoxymaltose in the Perioperative Management of Moderate to Severs Iron Deficiency" Anemia J Minim Invasive Gynecol. Nov.-Dec. 2015;22(6S):S211-S212.

European Crohn's and Colitis Organisation [ECCO] European Consensus on the Diagnosis and Management of Iron Deficiency and Anaemia in Inflammatory Bowel Diseases J Crohns Colitis 2015; 9 (3): 211-222.

Royal College of Obstetricians and Gynaecologists Blood Transfusion in Obstetrics Green-top Guideline No. 47; May 2015.

NCGC National Clinical Guideline Centre (NICE) Anaemia Management in Chronic Kidney Disease Partial update 2015 Clinical Guideline Methods, evidence and recommendations © National Clinical Guideline Centre—2015.

Kotzé et al. "British committee for standards in haematology guidelines on the identification and management of pre-operative anaemia." British Journal of Haematology. Nov. 2015;171(3):322-31.

National Comprehensive Cancer Network Cancer- and chemotherapy-induced anemia; 2015.

Nice UK Blood transfusion NICE guideline: 2015.

Society for the Advancement of Blood Management Anemia Prevention and Management Program Implementation Guide; 2015.

Toledano et al. "Clinical use of ferric carboxymalfose in patients with solid tumours or haematological malignancies in France" Support Care Cancer. Jan. 2016;24(1):67-75.

Mantadakis et ai. "Advances in Pediatric Intravenous Iron Therapy" Pediatr Blood Cancer. Jan. 2016;63(1):11-6.

Robles-Mezcua et al. "Efficacy, safety and prognostic benefit of intravenous iron therapy with ferric carboxymaltose in patients with heart failure and left ventricular dysfunction" Int J Cardiol. Jan. 1, 2016:202:118-20.

Calvet et al. "Cost-minimization analysis favours intravenous ferric carboxymaltose over ferric sucrose or oral iron as preoperative treatment in patients with colon cancer and iron deficiency anaemia" Technol Health Care. 2016;24(1):111-20.

Okam et al. "Iron deficiency anemia treatment response to oral iron therapy: a pooled analysis of five randomized controlled trials" Haematologica. Jan. 2016;101(1):e6-7.

Lieske et al. "Intravenous iron administration in restless legs syndrome: An observational study in geriatric pattents" Z Gerontol Geriatr. Oct. 2016;49(7):626-631.

Quintana-Diaz et al. "A fast-track anaemia clinic in the Emergency Department: feasibility and efficacy of intravenous iron administration for treating sub-acute iron deficiency anaemia" Blood Transfus. Mar. 2016;14(2):126-33.

Rognoni et al. "Efficacy and Safety of Ferric Carboxymaltose and Other Formulations in Iron-Deficient Patients: A Systematic Review and Network Meta-analysis of Randomised Controlled Trials" Clin Drug Investig. Mar. 2016;36(3):177-94.

Calleja et al. "Colon Cancer Study Group. Ferric carboxymaltose reduces transfusions and hospital stay in patients with colon cancer and anemia" Int J Colorectal Dis. Mar. 2016,31(3):543-51.

Rineau et al. "implementing a blood management protocol during the entire perioperative period allows a reduction in transfusion rate in major orthopedic surgery: a before-after study" Transfusion. Mar. 2016;56(3):873-81.

Koduru et al. "The role of ferric carboxymaltose in the treatment of iron deficiency anemia in patients with gastrointestinal disease" Therap Adv Gastroenterol. Jan. 2016;9(1): 76-85.

Froessler et al. "The Important Role for Intravenous Iron in Perioperative Patient Blood Management in Major Abdominal Surgery: A Randomized Controlled Trial" Ann Surg. Jul. 2016,264(1):41-6.

Philipp et al. "Diluting ferric carboxymaltose in sodium chloride infusion solution (0.9% w/v) in polypropylene bottles and bags, effects on chemical stability" Eur J Hosp Pharm. Jan. 2016;23(1)22-27.

Mahey et al. "Randomized controlled trial comparing ferric carboxymaltose and iron sucrose or treatment of iron deficiency anemia due to abnormal uterine bleeding" Int J Gynaecol Obstet. Apr. 2016; 133(1):43-8.

Gupta et al. "Ferrous iron content of intravenous iron formulations" Biometals. Jun. 2016;29(3):411-5.

Cooper et al. "Relation of Longitudinal Changes in Quality of Life Assessments to Changes in Functional Capacity in Patients With Heart Failure With and Without Anemia" Am J Cardiol. May 1, 2016,117(9):1482-7.

Frew et al. "Impact of a blood management protocol on transfusion rates and outcomes following total hip and knee arthroplasty" Ann R Coll Surg Engl. Jul. 2016;98(6):380-6.

García-López et al. "High-dose intravenous treatment in iron deficiency anaemia in inflammatory bowel disease: early efficacy and impact on quality of life" Blood Transfus. 2016 May;14(2):199-205.

Fell et al. "Impact of individual intravenous iron preparations on the differentiation of monocytes towards macrophages and dendritic cells" Nephrol Dial Transplant. Nov. 2016;31(11):1835-1645.

Bernabeu-Wittel et al. "PAHFRAC-01 Investigators, Ferric carboxymaltose with or without erythropoietin in anemic patients with hip fracture: a randomized clinical trial" Transfusion. Sep. 2016;56(9):2199-211.

Pandey et al. "Iron Treatment Strategies in Dialysis-Dependent CKD" Semin Nephrol Mar. 2016;36(2):105-11.

Macdougall IC. "Iron Treatment Strategies in Nondialysis CKD" Semin Nephrol. Mar. 2016,36(2):99-104.

Sangrós el al. "Symptomatic hypophosphataemic osteomalacia secondary to the treatment with iron carboxymaltose detected in bene scintigraphy" Rev Esp Med Nucl Imagen Mol. Nov.-Dec. 2016;35(6):391-393.

Gaillard et al. "Hepcidin Response to Iron Therapy in Patients with Non-Dialysis Dependent CKD: An Analysis of the FIND-CKD Trial" PLoS One. Jun. 8, 2016;11(6):e0157063.

(56) References Cited

OTHER PUBLICATIONS

Ghaly S. "Iron and vitamin D deflciency in inflammatory bowel disease" J Gastroenterol Hepatol. Jun. 2016;31 Suppl 1:27-8.
Gearry RB. "Introduction" J Gastroenterol Hepatol. Jun. 2016:31 Suppl 1:23.
Drakou et al. "Assessment of serum bioactive hepcidin-25, soluble transferrin receptor and their ratio in prediaiysis patients: Correlation with the response to intravenous ferric carboxymaltose" Blood Cells Mol Dis. Jul. 2016;59:100-5.
Shepshelovich ei al. "Intravenous Versus Oral Iron Supplementation for the Treatment of Anemia in CKD: An Updated Systematic Review and Meta-analysis" Am J Kidney Dis. Nov. 2016;68(5):677-690.
Lofruthe et al. "Intravenous Iron Carboxymaltose as a Potential Therapeutic in Anemia of inflammation" PLoS One. Jul. 12, 2016;11(7):e0158599.
Bart et al, "Elevation of iron storage in humans attenuates the pulmonary vascular response te hypoxia" J Appl Physiol (1985). Aug. 1, 2016;121(2):537-44.
Varcher et al. "Iron deficiency intravenous substitution in a Swiss academic primary care division: analysis of practices" Int J Gen Med. Jul. 4, 2016;9:221-7. doi: 10.2147/IJGM.S107821. eCollection 2016.
Neiser et al. "Assessment of Dextran Antigenicity of Intravenous Iran Preparations with Enzyme-Linked Immunosorbent Assay (ELISA)" Int J Mol Sci. Jul. 21, 2016;17(7):1185.
Khalafallah et al. "Intravenous ferric carboxymalfose versus standard care in the management of postoperative anaemia; a prospective, open-label, randomised controlled trial" Lancet Haematol. Sep. 2016;3(9):e415-25.
Muñoz et al. "Postoperative intravenous iron: a simple strategy to improve outcomes" Lancet Haematol. Sep. 2016;3(9):e401-2.
Rocha et al. "Acute decompensated heart failure (ADHF): A comprehensive contemporary review on preventing early readmissions and postdischarge death" Int J Cardiol. Nov. 15, 2016;223:1035-1044.
Salvadori et al. "Ferric carboxymaltose reduces the number of red blood cell units transfused and allows transfusion independence to be obtained in patients with iron deficiency anemia secondary to gastrointestinal chronic blood loss" Transfusion. Nov. 2016,56(11);2720-2726.
Litton et al. "Australian and New Zealand Intensive Care Society Clinical Trials Group, Intravenous iron or placebo for anaemia in intensive care: the IRONMAN multicentre randomized blinded trial : A randomized trial of IV Iron in critical illness" Intensive Care Med. Nov. 2016;42(11)1715-1722.
Wienbergen et al. "RAID-HF (Registry Analysis of Iron Deficiency-Heart Failure) REGISTRY Study Group. Usefulness of Iron Deficiency Correction in Management of Patients With Heart-Failure [from the Registry Analysis of iron Deficiency-Heart Failure (RAID-HF) Registry]" Am J Cardiol. Dec. 15, 2016;118(12):1875-1880.
Cook et al. "Evolving therapies for the management of chronic and acute decompensated heart failure" Am J Health Syst Pharm. Nov. 1, 2016;73(21);1745-1754.
Yeo et al. "Rationale and design of a pilot randomized controlled trial to assess the role of intravenous ferric carboxymaltose in Asian patients with heart failure (Practice-Asia-HF)" ESC Heart Fail. Jun. 2016;3(2):71-76.
Macher et al. "High-dose intravenously administered iron versus orally administered iron in blood donors with iron deficiency: study protocol for a randomised, controlled trial" Trials. Oct. 28, 2016;17(1):527.
Cho et al. "Clinical efficacy of ferric carboxymaltose treatment in patients with restless legs syndrome" Sleep Med. Sep. 2016;25:16-23.
Aporta et al., "Retrospective Case Reports of Anemic Pregnant Women Receiving Intravenous Ferric Carboxymaltose: Experience from a Tertiary Hospital in Spain" Obstet Gynecoi Int. 2016;2016:5060252.
Roberts et al. "Effects of intravenous iron on fibroblast growth factor 23 (FGP23) in haemodialysis patients: a randomized controlled trial" BMC Nephrol. Nov. 16, 2016; 17(1):177.
Schaefer et al. "Choice of High-Dose Intravenous iron Preparation Determines Hypophosphatemia Risk" PLoS One. Dec. 1, 2016,11(12):e0167146.
Baird-Gunning et al. "Correcting iron deficiency" Aust Prescr. Dec. 2016;39(6):193-199.
Damineni et al. "IV Ferric Carboxymaltose Vs Oral Iron in the Treatment of Post-partum Iron Deficiency Anaemia" J Ciin Diagn Res. Nov. 2016,10(11):QC08-QC10.
Barking, Havering and Redbridge University Hospitals—NHS Trust A Protocol for Use and Administration of Intravenous Iron Isomaltoside (Monofer®)—2016.
Wang M Iron Deficiency and Other Types of Anemia in Infants and Children Am Fam Physician 2016; 93 (4): 270-278.
National Blood Authority, Australia Iron product choice and dose calculation—adults Guidance for Australian Health Providers: 2016.
South Australia Maternal A Neonatal Community of Practice Clinical Guideline Iron Infusion.
City Hospitals Sunderland NHS Foundation Trust Directorate of Obstetrics and Gynaecology Anaemia in Pregnancy: 2016.
Belfast Health and Social Care Trust Management of iron deficiency in pregnancy; 2016.
Dorset County Hospital NHS Foundation Trust The Management of Iron Deficiency Anaemia in Pregnancy; Maternity Unit Guideline: 2016.
Maidstone and Tunbridge Wells NHS Trust MonoFer® (Intravenous Iron Isomaltoside) use in the Antenatal & Postnatal period guideline; 2019.
Luton & Dunstable University Hospital Iron Isomaltoside 1000 (Monofer®) prescription sheet for Adult IBD Patients 2016???? English Abstract.
Munoz et al. Network far the Advancement of Patient Blood Management, Haemostasis and Thrombosis (NATA) in collaboration with the International Federation of Gynaecology and Obstetrics (FIGO) and the European Board and Collage of Obstetrics and Gynaecology (EBCOG) Patient blood management in obstetrics: management of anaemia and haematinic deficiencies in pregnancy and in the post-partum period: NATA consensus statement Transfus Med 2018; 28 (1): 22-39.
Task Force far the diagnosis and treatment of acute and chronic heart failure of the European Society of Cardiology (ESC) 2016 ESC Guidelines for the diagnosis and treatment of acute and chronic heart failure Eur J Heart Fail 2016; 18 (8): 891-975.
European Society of Anaesthesiology Management of severe perioperative bleeding: guidelines from the European Society of Anaesthesiology First update 2016 Eur J Anaesthesiol 2017; 34: 332-395.
"Adult Monofer infusion guideline-" University Hospital Southampton; issued Apr. 2016.
Breymann et al. FER-ASAP investigators. Ferric, carboxymallose vs. oral Iron in the treatment of pregnant women with iron deficiency anemia: an international open-label, randomized controlled trial (FER-ASAP) J Perinat Med. May 24, 2017,45(4):443-453.
Haddad et al. "Iron-regulatory proteins secure iron availability in cardiomyocytes to prevent heart failure" Eur Heart J. Feb. 1, 2017;38(5):362-372.
Valério et al. "Pediatric Crohn's disease, iron deficiency anemia and intravenous iron treatment: a follow-up study" Scand J Gastroenterol. Jan. 2017;52(1):29-33.
Powers et al. "Intravenous Ferric Carboxynialtose In Children with Iron Deficiency Anemia Who Respond Poorly to Oral Iron" J Pediatr. Jan. 2017; 180:212-216.
Bager et al. "Drug-specific hypophosphatemia and hypersensitivity reactions following different Intravenous Iron infusions" Br J Clin Pharmacol, May 2017;83(5):1118-1125.
Hempel et al. "Distinct in vitro Complement Activation by Various Intravenous iron Preparations." Am J Nephrol. 2017;45(1):49-59.
Luporsi et al. "Use of iron sucrose and red blood cell transfusions in anaemic cancer patients in France (OncoFer study)" Support Care Cancer. Mar. 2017,25(3):973-982.

(56) References Cited

OTHER PUBLICATIONS

Verhoef et al. "Iron nanomedicines induce Toll-like receptor activation, cytokine production and complement activation." Biomaterials. Mar. 2017, 119:68-77.
Keeler et ai. "IVICA Trial Group. Randomized clinical trial of preoperative oral versus intravenous iron in anaemic patients with colorectal cancer" Br Surg. Feb. 2017:104(3):214-221.
Macdougall et al. "FIND-CKD Study investigators Renal function in patients with non-dialysis chronic kidney disease receiving intravenous ferric carboxymaltose: an analysis of the randomized FIND-CKD trial" BMC Nephrol. Jan. 17, 2017:18(1)24.
Quintana-Diaz et al. "A fast-track anaemia clinic in the Emergency Department: cost-analysis of intravenous iron administration for treating iron-deficiency anaemia." Blood Transfus. Sep. 2017,15(5):438-446.
Mantadakis et al. "Safety and efficacy of ferric carboxymaltose in children and adolescents with iron deficiency anemia." J Pediatr. May 2017;184:241.
Rodrigues et ai. "Porphyria Cutanea Tarda in a Patient with End-Stage Renal Disease: A Case of Successful Treatment with Deferoxamine and Ferric Carbexymaltose Case." Rep Nephrol. 2017;2017:4591871.
Pacho et al. "Early Postdischarge STOP-HF-Clinic Reduces 30-day Readmissions in Old and Frail Patients With Heart Failure." Rev Esp Cardiol (Engl Ed). Aug. 2017;70(8)631-638.
San et al. "Ferric carboxymaltose-induced hypophosphataemia after kidney transplantation." Neth J Med. Mar. 2017;75(2):65-73.
Anand et al. "Severe hypophosphataemia after intravenous iron administration." BMJ Case Rep. Mar. 13, 2017;2017:bcr2016219160.
Aksan et al. "Systemalic review with network meta-analysis: comparative efficacy and tolerability of different intravenous iron formulatlons for the treatment of iron deficiency anaemia in patients with inflammatory bowel disease." Aliment Pharmacol Ther. May 2017:45(10):1303-1318.
Roger et al. "FIND-CKD Study Investigators. Safety of intravenous ferric carboxymaltose versus oral iron in patients with nondialysis-dependent CKD: an analysis of the 1-year FIND-CKD trial." Nephrol Dial Transplant. Sep. 1, 2017;32(9):1530-1539.
Keeler et al. "IVICA Trial 'Group. Randomized clinical trial of preoperative oral versus intravenous iron in anaemic patients with colorectal cancer" Br J Surg. Feb. 2017;104(3):214-221.
Macdougail et al. "FIND-CKD Study investigators. Renal function in patients with non-dialysis chronic kidney disease receiving intravenous ferric carboxymaltose: an analysis of the randomized FIND-CKD trial" BMC Nephrol. Jan. 17, 2017;18(1):24.
Rodrigues et al. "Porphyria Cutanea Tarda in a Patient with End-Stage Renal Disease: A Case of Successful Treatment with Deferoxamine and Ferric Carboxymalfose Case." Rep Nephrol. 2017;2017:4591871.
Sari et al. "Ferric carboxymaltose-induced hypophosphataemia after kidney transplantation," Neth J Med. Mar. 2017;75(2):65-73.
Anand et ai. "Severe hypophosphataemia after intravenous iron administration." BMJ Case Rep. Mar. 13, 2017;2017:bcr2016219160.
Aksan et al. "Systematic review with network meta-analysis: comparative efficacy and tolerability of different intravenous iron formulations for the treatment of iron deficiency anaemia in patients with inflammatory bowel disease." Aliment Pharmacol Ther. May 2017;45(10):1303-1318.
Amenós et al. "Heart failure in patients with kidney disease and iron deficiency; the role of iron therapy" Nefrologia. Nov.-Dec. 2017;37(6):587-591.
Trenkwalder et al. "Ferric carboxymaltose in patients with restless legs syndrome and nonanemic iron deficiency: A randomized trial" Mov Disord. Oct. 2017; 32(10):1478-1482.
Gstrein et al, "Iron substitution in the treatment of chronic heart failure" Swiss Med Wkly. Jun. 23, 2017;147:w14453.
Van Veldhuisen et al. "Effect of Ferric Carboxymattose on Exercise Capacity in Patients With Chronic Heart Failure and Iron Deficiency" Circulation. Oct. 10, 2017;136(15):1374-1383.
Low et al. "Iron deficiency and new insights into therapy" Med J Aust. Jul. 17, 2017;207(2):81-87.

Sharma et al. "Comparative Study of Efficacy and Safety of Ferric Carboxymaltose Versus Iron Sucrose in Post-partum" Anaemia J Obstet Gynaecol India. Aug. 2017;67(4):253-257.
Robalo et al. "Efficacy and Tolerability of Intravenous Ferric Carboxymaltose in Patients with Iron Deficiency at a Hospital Outpatient Clinic: A Retrospective Cohort Study of Real-World Clinical Practice." Anemia. 2017;2017:3106890.
Poscia et al. "Sustainability of Endovenous Iron Deficiency Anaemia Treatment: Hospital-Based Health Technology Assessment in IBD Patients," Biomed Res Int. 2017;2017:3470893.
Theidel et al. "Budget impact of intravenous iron therapy with ferric carboxymaltose in patients with chronic heart failure and iron deficiency in Germany" ESC Heart Fail. Aug. 2017;4(3):274-281.
Milovanovic et ak "Therapy experiences and preferences among patients with anemia: Results of a cross-sectional survey among Italian patients with inflammatory bowel disease," Dig Liver Dis. Oct. 2017;49(10):1098-1103.
Toblli et al. "Markers of oxidative/nitrosative stress and inflammation in lung tissue of rats exposed to different intravenous iron compounds." Drug Des Devel Ther. Aug. 1, 2017;11:2251-2263.
Tan et al. "Retrospective review of effectiveness and safety of intravenous ferric carboxymaltose given to children with iron deficiency anaemia in one UK tertiary centre." Eur J Pediatr. Oct. 2017;176(10):1419-1423.
Pollock et al. "A budget impact analysis of parenteral iron treatments for iron deficiency anemia in the UK: reduced resource utilization with iron isomaltoside 1000." Clinicoecon Outcomes Res. Aug. 10, 2017;9:475-483.
Breymann et al. "Diagnosis and treatment of iron-deficiency anaemia in pregnancy and postpartum." Arch Gynecol Obstet. Dec. 2017;296(6):1229-1234.
Kim et al. "Ferric Carboxymaltose to Treat Isovolemic Anemia-Reply" JAMA. Oct. 3, 2017:318(13):1261-1282.
Yu et al. "Ferric Carboxymalfose to Treat Isovolemic Anemia." JAMA. Oct. 3, 2017;318(13):1281.
Mishra et al. "Role of Intravenous Ferric Carboxy-maltose in Pregnant Women with Iron Deficiency Anaemia." J Nepal Health Res Counc. Sep. 8, 2017;15(2):96-99.
Katz SD, "Pumping Iron" to Improve Exercise Performance in Heart Failure: New Data and New Guidelines Circulation. Oct. 10, 2017;136(15):1384-1386.
Adkinson et al. "Comparative safety of intravenous Ferumoxytol versus Ferric Carboxymaltose for the Treatment of iron Deficiency Anemia: rationale and study design of a randomized double-blind study with a focus on acute hypersensitivity reactions." J Blood Med. Sep. 26, 2017;8:155-163.
Pollock et al. "Intravenous iron treatments for iron dsficiency anemia in inflammatory bowel disease: a budget impact analysis of iron isomaltoside 1000 (Monofer) in the UK." Expert Opin Drug Deliv. Dec. 2017; 14(12):1439-1446.
Verhaeghe et al. "The effectiveness of intravenous iron for iron deficiency anemia in gastrointestinal cancer patients: a retrospective study." Ann Gastroenterol. 2017;30(6):654-663.
Dalal et al. "Effect of ferric carboxymaltose on hospitalization and mortality outcomes in chronic heart failure: A meta-analysis," Indian Heart J. Nov.-Dec. 2017(69);(6);736-741.
Macdougall IC. "Intravenous iron therapy in patients with chronic kidney disease: recent evidence and future directions." Clin Kidney J. Dec. 2017;10(Suppl 1):i16-124.
Toblli et al. "Cardiovascular, liver, and renal toxicity associated with an intravenous ferric carboxymaltose similar versus the originator compound." Drug Des Devel Ther. Nov. 30, 2017;11:3401-3412.
Munoz et al International consensus statement on the peri-operative management of anaemia and iron deficiency Anaesthesia 2017; 72 (2): 233-247.
Achebe et al. "How I treat anemia in pregnancy: iron, cobalamin, and folate." Blood 2017; 129 (8): 940-949.
The Dudley Group NHS Foundation Trust Intravenous Iron to Correct Pre-Operative Iron Deficiency Anaemia Standard Operating Procedure; 2017.

(56) References Cited

OTHER PUBLICATIONS

European Commission Supporting Patient Blood Management (PBM) in the EU A Practical Implementation Guide for Hospitals: Mar. 2017.
Singleton Hospital Swansea NHS Wales Intravenous Iron Infusion in Pregnancy (MONOFER®); 2017.
Vaglio et al. "The Italian regulatory guidelines for the implementation of patient blood management." Blood Transfusion. Jul. 2017;15(4):325.
Royal United Hospitals Bath NHS Foundation Trust Guidelines for use of parenteral iron; HAEM 006; 2017.
South Tees Hospitals NHS Foundation Trust Anaemia in pregnancy, 2017.
Royal National Orthopaedic Hospital NHS Trust Intravenous Iron for the Treatment of Pre Operative Anaemia in Adults; 2017.
American College of Cardiology, American Heart Association, and the Heart Failure Society of America 2017 ACC/AHA/HFSA Focused Update of the 2013 ACCF/AHA Guideline for the Management of Heart Failure Circulation 2017; 136 (6): e137-e161.
Canadian Cardiovascular Society 2017 Comprehensive Update of the Canadian Cardiovascular Society Guidelines for the Management of Heart Failure Canadian Journal of Cardiology 2017; 33: 1342-1433.
Ashford and St Peter's Hospital NHS Foundation Trust MonoFer® (Iron Isomaltoside) Total Dose Iron Infusion; 2017.
The Renal Association Clinical Practice Guideline Anaemia of Chronic Kidney Disease BMC Nephrol 2017; 18 (1): 345.
Adult Cardiac Surgery of the European Association for Cardio-Thoracic Surgery (EACTS) and the European Association of Cardiothoracic Anaesthesiology (EACTA) 2017 EACTS/EACTA Guidelines on patient blood management for adult cardiac surgery Eur J Cardiothorac Surg 2018; 53 (1): 79-111.
European Society of Medical Oncology (ESMO) Management of anaemia and Iron deficiency in patients with cancer: ESMO Clnical Practice Guidelines Ann Oncol 2018; 29 (Suppl 4): iv96-iv110.
City Hospitals Sunderland NHS Foundation Trust a Protocol for Use and Administration of Intravenous Iron Isomaltoside (MONOFER®) in Management of Pre-Operative Anaemia, Jan. 2017.
Anker et ai. "Effects of ferric carboxymaltose on hospitalisations and mortality rates in iron-deficient heart failure patients: an individual patient data meta-analysis." Eur J Heart Fail. Jan. 2018;20(1):125-133.
Qassim et al. "Safety and efficacy of intravenous iron polymaltose, iron sucrose and ferric carboxymaltose in pregnancy: A systematic review," Aust N Z J Obstet Gynaecol Feb. 2018;58(1):22-39.
Garvican-Lewis el al. "Influence of combined iron supplementation and simulated hypoxia on the haematological module of the athlete biological passport." Drug Test Anal. Apr. 2018;10(4):731-741.
Stewart Coats AJ. "Intravenous ferric carboxymaltose for heart failure with Iron deficiency" Eur J Heart Fail Jan. 2018;20(1):134-135.
Daniilidis et al. "Safety and efficacy of intravenous iron administration for uterine bleeding or postpartum anaemia: a narrative review." J Obstet Gynaecol. May 2018;38(4):443-447.
Schindler et al. "Intravenous Ferric Carboxymaltose in Patients with Type 2 Diabetes Mellitus and Iron Deficiency. CLEVER Trial Study Design and Protocol." Diabetes Ther. Feb. 2018;9(1):37-47.
Boomershine et al. "A Blinded, Randomized. Placebo-Controlled Study to Investigate the Efficacy and Safety of Ferric Carboxymaltose in Iron-Deficient Patients with Fibromyalgia." Rheumatol Ther. Jun. 2018;5(1):271-281.
Huang et al. "A controlled study of the effects cf ferric carboxymaltose on bone and haematinic biomarkers in chronic kidney disease and pregnancy." Nephrol Dial Transplant. Sep. 1, 2018;33(9):1628-1635.
Singler K. [Iron, a "mlraicle cure" for chronic cardiac insufficiency?] Z Gerontol Geriatr. Feb. 2018;51(2):157-159. doi: 10.1007/s00391-017-1357-5. Epub Dec. 14, 2017. English Abstract.
Papadopoulos et al. "Safety and efficacy of parenteral iron in children with inflammatory bowel disease." Br J Clin Pharmacol. Apr. 2018;84(4):694-699.
Klein et al. "Severe FGF23-based hypophosphataemic osteomalacia due to ferric carboxymaltose administration." BMJ Case Rep, Jan. 3, 2018;2018:bcr2017222851.
Naqash et al., "Effectiveness and safety of ferric carboxymaltose compared to iron sucrose in women with iron deficiency anemia; phase IV clinical trials." BMC Womens Health. Jan. 5, 2018;18(1):6.
Castberg et al. "Increased Plasmodium chabaudi malaria mortality in mice with nutritional iron deficiency can be reduced by short-term adjunctive iron supplementation." Malar J. Jan. 16, 2018;17(1):34.
Yeo et al. "Single-dose intravenous iron in Southeast Asian heart failure patients; A pilot randomized placebo-controlled study (Practice-Asia-HF)." ESC Heart Fail. Apr. 2018;5(2):344-353.
Ikuta et al. "Pharmacokinetics, pharmacodynamics, safety, and tolerability of intravenous ferric carboxymaltose: a dose-escalation study in Japanese volunteers with iron-deficiency anemia." Int J Hematol. May 2018;107(5):519-527.
Mishra et al. "Safety and Efficacy of Intravenous Ferric Carboxy Maltose in Iron Deficiency Anaemia During Post-partum." Period J Nepal Health Res Counc. Jan. 1, 2018;15(3):208-211.
Grote et al. "Definition of Iron Deficiency Based on the Gold Standard of Bone Marrow Iron Staining in Heart Failure Patients." Circ Heart Fail. Feb. 2018;11(2):e004519.
Adkinson et al. "Comparative safely of intravenous ferumoxytol versus ferric carboxymaltose in iron deficiency anemia: A randomized trial," Am J Hematol. May 2018;93(5):683-690.
Allen et al. "International Restless Legs Syndrome Study Group (IRLSSG). Evidence-based and consensus clinical practice guidelines for the iron treatment of restless legs syndrome/Willis-Ekbom disease in adults and children: an IRLSSG task force report." Sleep Med. Jan. 2018;41;27-44.
Rocha et al. "The Burden of Iron Deficiency in Heart Failure: Therapeutic Approach," J Am Coll Cardiol Feb. 20, 2018:71(7):782-793.
Schnorr et al. "Bioequivalence decision for nanoparticular iron complex drugs for parenteral administration based on their disposition." Regul Toxicol Pharmacol. Apr. 2018;94:293-298.
Cho et al. "Efficacy of ferric carboxymaltose (FCM) 500 mg dose for the treatment of Restless Legs Syndrome." Sleep Med. Feb. 2018;42:7-12.
Kangaspunta et al. "Inflammatory bowei disease and anemia: intravenous iron treatment," Scand J Gastroenterol. Apr. 2018;53(4):430-434.
Gilmartin et al. "Retrospective cohort study comparing the adverse reactions and efficacy of intravenous iron polymaltose with ferric carboxymaltose for iron deficiency anemia." Int J Gynaecol Obstet. Jun. 2018;141:(3):315-320.
Delpeuch et al. "Financial impact of intravenous iron treatments on the management of anaemia inpatients: a 1 year observational study." Int J Clin Pharm. Jun. 2018;40(3):686-692.
Scott LJ. "Ferric Carboxymaltose: A Review in Iron Deficiency." Drugs. Mar. 2018;78(4):479-493.
Garvican-Lewis et al. "Intravenous Iron Does Not Augment the Hemoglobin Mass Response to Simulated Hypoxia." Med Sci Sports Exerc Aug. 2018;50(8):1669-1878.
Kim et al. "Postoperative Intravenous Ferric Carboxymaltose Reduces Transfusion Amounts after Orthopedic Hip Surgery." Clin Orthop Surg. Mar. 2018;10(1):20-25.
Peters et al. "Post-Operative Iron Carboxymaltose May Have an Effect on Haemoglobin Levels in Cardiothoracic Surgical Patients on the ICU—an Observational Pilot Study about Anaemia Treatment with Intravenous Iron Transfus." Med Hemother. Jan. 2018;45(1):42-46.
Knoeff et al. "Medication practice in hospitals: rare nanosimilars evaluated and substituted correctly?" Eur J Hosp Pharm. Mar. 2018,25(2):79-84.
Miñana et al. "Changes in myocardial iron content following administration of intravenous iron (Myocardial-IRON): Study design." Ciin Cardiol. Jun. 2018;41(6):729-735.

(56) References Cited

OTHER PUBLICATIONS

Akhuemonkhan et al. "Adverse Reactions After Intravenous Iron Infusion Among inflammatory Bowel Disease Patients in the United States, 2010-2014." Inflamm Bowel Dis. Jul. 12, 2018;24(8):1801-1807.
Cunha et al. "Iron deficiency in chronic and acute heart failure: A contemporary review on intertwined conditions." Eur J Intern Med. Jun. 2018;52:1-7.
Froessler et al. "Assessing the costs and benefits of perioperative iron deficiency anemia management with ferric carboxymalfose in Germany." Risk Manag Healthc Policy. Apr. 24, 2018:11:77-82.
Froessler et al. "Treatment of iron deficiency and iron deficiency anemia with intravenous ferric carboxymaltose in pregnancy." Arch Gynecol Obstet. Jul. 2018;298(1):75-82.
Stöhr et al. "High-Dose Ferric Carboxymaltose in Patients With HFrEF Induces Significant Hypophosphatemia." J Am Coll Cardiol. May 15, 2018;71(19):2270-2271.
Winkelmann et al. "Treatment of restless legs syndrome: Evidence-based review and implications for clinical practice (Revised 2017)§" Mov Disord. Jul.2018;33(7): 1077-1091.
Coussirou et al. "Impact of ferric carboxymaltose on ths evolution of hemoglobin and ECOG performance status in iron-deficient patients with solid tumors: a 3-month follow-up retrospective study." Support Care Cancer. Nov. 2018;26(11):3827-3834.
Beverina et al. "Extreme anemia (Hb 33 g/L) in a 13-year-old girl: Is the transfusion always mandatory?" Transfus Apher Sci. Aug. 2018;57(4):512-514.
Blanche et al., "Use of intravenous iron in cyanotic patients with congenital heart disease and/or pulmonary hypertension." Int J Cardiol. Sep. 15, 2018,267:79-83.
Rineauet al. "Iron deficiency without anemia is responsible for decreased left ventricular function and reduced mitochondrial complex I activity in a mouse model," Int J Cardiol. Sep. 1, 2018;266:206-212.
Darba et al. "Impact Analysis of Oral Fisiogen Ferro Forte® versus Intravenous Iron tor the Management of Iron Deficiency in Chronic Kidney Disease in Spain." Clin Drug Investig. Sep. 2018;38(9):801-811.
Ellermann et al. "Treating Anemia in the Preanesthesia Assessment Clinic: Results of a Retrospective Evaluation." Anesth Analg. Nov. 2018;127(5):1202-1210.
Stein et al., "Safety and Efficacy of Ferric Carbexymaltose in the Treatment of iron Deficiency Anaemia in Patients with Inflammatory Bowel Disease, in Routine Daily Practice." J Crohns Colitis, Jun. 28, 2018;12(7):826-834.
Mishra et al. "Iron Deficiency Anemia with Menorrhagia: Ferric Carboxymaltose a Safer Alternative to Blood Transfusion." J Midlife Health. Apr.-Jun. 2016;9(2):92-96.
Mundy et al. "A comment on the comparative safety of intravenous ferumoxytol versus ferric carboxymaltose in iron deficiency anemia." Am J Hematol. Sep. 2018;93(9):E231-E232.
Strauss et al. "A response by Strauss et al. to" a comment on the comparative safely of intravenous ferumoxytol versus ferric carboxymaltose in iron deficiency anemia, Am J Hematol. Sep. 2018;93(9):232-E233.
Basora et al. "Cost-effectiveness analysis of ferric carboxymaltose in pre-operative haemoglobin optimisation in patients undergoing primary knee arthroplasty." Blood Transfus. Sep. 2018;16(5):438-442.
Füllenbach et al. "Iron supplementation in a case of severe iron deficiency anaemia." Br J Anaesth. Aug. 2018;121(2):502-504.
Lichtenstein et al. "Improved Hemoglobin Response with Ferric Carboxymaltose in Patients with Gastrointestinal-Related Iron-Deficiency Anemia Versus Oral Iron." Dig Dis Sci. Nov. 2018,63(11):3009-3019.
Biboulet et al., "Preoperative Epoetin-α with Intravenous or Oral Iron for Major Orthopedic Surgery: A Randomized Controlled Trial." Anesthesiology, Oct. 2018;129(4):710-720.
Lam et al. "Iron deficiency in chronic heart fallure: case-based practical guidance." ESC Heart Fail Oct. 2018,5(6):764-771.

Wittkamp et al. "Hepcidin as a potential predictor for preoperative anemia treatment with intravenous iron-A retrospective pilot study." PLoS One, Aug. 8, 2018;13(8):e0201153.
Shim et al. "Efficacy and safety of ferric carboxymaltose versus ferrous sulfate for iron deficiency anemia during pregnancy: subgroup analysis of Korean women." BMC Pregnancy Childbirth. Aug. 28, 2018;18(1):349.
Auerbach et al. "Ferumoxytol for the treatment of iron deficiency anemia." Expert Rev Hematol. Oct. 2018;11(10):829-834.
Lima et al. "Role of intravenous iron in the treatment of anemia in patients with gastrointestinal tract tumors undergoing chemotherapy: a single-center, observational study." Int Gen Med. Aug. 22, 2018:11:331-336.
Dinatolo et al. "Iron deficiency in heart failure." J Cardiovasc Med (Hagerstown). Dec. 2018;19(12):706-716.
Hofman et al. "Switching iron sucrose to ferric carboxymaltose associates to better control of iron status in hemodialysis patients." BMC Nephrol. Sep. 20, 2018:19(1):242.
McDonagh et al. "Screening, diagnosis and treatment of iron deficiency in chronic heart failure: putting the 2016 European Society of Cardiology heart failure guidelines into clinical practice." Ear J Heart Fail. Dec. 2018;20(12):1664-1672.
Abdelazim et al. "Treatment of iron deficiency and iron deficiency anemia with intravenous ferric carboxymaltase in pregnancy." Arch Gynecoi Obstet. Dec. 2018;298(6):1231-1232.
Melenovsky et al. "Skeletal Muscle Abnormalities and Iron Deficiency in Chronic Heart Failure(An Exercise (31)P Magnetic Resonance Spectroscopy Study of Calf Muscie)." Circ Heart Fail Sep. 2018;11(9):e004800.
Paterek et al. "Beneficial effects of intravenous iron therapy in a rat model of heart failure with preserved systemic iron status but depleted intracellular cardiac stores," Sci Rep, Oct. 25, 2018:8(1):15758.
Froessler et al. "Response to letter to the Editor: Treatment of iron deficiency and iron deficienov anemia with intravenous ferric carboxymaltose in pregnancy." Arch Gynecol Obstet. Dec. 2018;298(6):1233-1234.
Salminen et al. "Restless Legs Syndrome and Other Movement Disorders of Sleep-Treatment Update." Curr Treat Options Neural. Nov. 9, 2018;20(12):55.
Hofmarcher et al. "Cost effectiveness of implementing ESC guidelines for treatment of iron deficiency in heart failure in the Nordic countries." Scand Cardiovasc J. Dec. 2018;52(6):348-355.
Pollock et al. "An Economic Evaluation of Iron Isomaltoside 1000 Versus Ferric Carboxymaltose in Patients with inflammatory Bowel Disease and Iron Deficiency Anemia in Denmark." Adv Ther. Dec. 2018;35(12):2128-2137.
Khalafallah et al. "A Prospective Randomised Controlled Trial of a Single Intravenous Infusion of Ferric Carboxymaltose vs Single Intravenous Iron Polymaltose or Daily Oral Ferrous Sulphate in the Treatment of Iron Deficiency Anaemia in Pregnancy." Semin Hematol. Oct. 2018;55(4):223-234.
Wolf et al. "Randomized trial of intravenous iron-induced hypophosphatemia." JCI Insight. Dec. 6, 2018;3(23):e124486.
Northern Health and Social Care Trust Antrim Area Hospital GastroenteroloEv IV Iron Protocol; 2018.
NHS GG&C South Sector Iron Deficiency Anaemia in Inflammatory Bowel Disease Guidelines—Jan. 2016.
The Newcastle upon Tyne Hospitals NHS Foundation Trust Protocol for intravenous iron(III) isomaltoside 1000 (monofer) in the perioperative care setting for the treatment of Iron deficiency anaemia where oral iron is not appropriate; 2018.
Liverpool Women's NHS Foundation Trust Standard Operational Procedure (SOP) Treatment of Iron Deficiency Anaemia with Monofer IV therapy.
Royal Papworth Hospital NHS Foundation Trust Intravenous iron isomaltoside (monofer) for correction of pre-operative iron deficiency anaemia in adult patients undergoing cardiac surgery; 2018.
Munoz et al. "An international consensus statement on the management of postoperative anaemia after major surgical procedures." Anaesthesia 2018; 73 (11): 1418-1431.
Liverpool Heart and Chest Hospital NHS Foundation Trust Parenteral Iron- Pre-Operative Protocol; Aug. 2818.

(56) References Cited

OTHER PUBLICATIONS

Enhanced Recovery Alter Surgery (ERAS) Society Guidelines for Perioperative Care in Elective Colorectal Surgeiy: Enhanced Recovery After Surgery (ERAS) Society Recommendations: 2018 World J Surg 2019; 43 (3): 659-695.
The Newcastle upon Tyne Hospitals NHS Foundation Trust Anaemia and Pregnancy; 2018.
Crohn's & Colitis Foundation Crohn's & Colitis Foundation's IBD Anemia Care Pathway Adapted from "Assessment of Gaps in Care and the Development of a Care Pathway for Anemia in Patients with inflammatory Bowel Diseases" by J. K. Hou, et al., 2017, IBP Journal, 23, p. 35.
Royal Free London NHS Foundation Trust Maternity—Intravenous Iron Infusion Monofer Prescribing and Administration Guideline; 2018.
Ikuta et al. "Comparison of efficacy and safety between intravenous ferric carboxymaltose and saccharated ferric oxide in Japanese patients with iron-deficiency anemia due to hypermenorrhea: a multi-center, randomized, open-label noninferiority study." Int J Hematol. Jan. 2019;109(1):41-49.
Govindappagari et al. "Treatment of Iron Deficiency Anemia in Pregnancy with Intravenous versus Oral Iron: Systematic Review and Meta-Analysis," Am J Perinatol. Mar. 2019;36(4):366-376.
Mulder et al. "Comparison of hypersensitivity reactions of intravenous iron: iron isomaltoside-1000 (Monofer®) versus ferric carboxymaltose (Ferinject®). A single center, cohort study." Br J Clin Pharmacol Feb. 2019;85(2):385-392.
Von Haehling et al. "Iron Deficiency in Heart Failure: An Overview." JACC Heart Fail. Jan. 2019;7(1):36-46.
Vikrant et al. "Successful Administration of Iron Sucrose in a Patient with an Anaphylactic Reaction to Ferric Carboxymaltose." Indian J Hematol Blood Transfus. Jan. 2019,35(1):199-200.
FIGO Working Group on Good Clinical Practice in Maternal-Fetal Medicine Good clinical practice advice: Iron deficiency anemia in pregnancy Int J Gynaecol Obstet 2019: 144 (3): 322-324.
Therapeutic Guidelines Limited (www.tg.org.au) Parenteral iron supplementation https://tgldcp.tg.org.au/viewTopic?topicfile=iron-deficency&sectionld=gig-c17-s3#toc_d1e234; 2019.
British Columbia Ministry of Health Guidelines & Protocols Advisory Committee Iron Deficiency—Diagnosis and Management BCGuidelines.ca; 2019.
Royal College of Nursing Iron Deficiency and Anaemia in Adults: RCN guidance for nursing practice; 2019.
American Society of Clinical Oncology (ASCO)/American Society of Hematology (ASH) Management of Cancer-Associated Anemia With Erythropoiesis-Stimulating Agents; ASCO/ASH Clinical Practice Guideline Update J Clin Oncology 2019; 37 (15): 1336-1351.
Government of Western Australia King Edward Memorial Hospital; 2019 Obstetrics & Gynaecology Clinical Practice Guideline Iron therapy: Intravenous.
QE Gateshead Maternity Anaemia in pregnancy and postnatal period; 2019.
British Society of Gastroenterology British Society of Gastroenterology consensus guidelines on the management of inflammatory bowel disease in adults Gut 2019; 68: s1-s106.
British Society for Haematology UK guidelines on the management of iron deficiency in pregnancy Br J Haematol 2020; 188 (6): 819-839.
Society for the Advancement of Blood Management Anemia in the Pre-Surgial Patient Recognition, Diagnosis and Management New Insights and Concepts for the Primary Care Provider; 2019.
Society for the Advancement of Blood Management SABM Administrative and Clinical Standards for Patient Blood Management Programs®; 2019.
Northern Health and Social Care Trust Maternity—Intravenous Iron Infusion Monofer Prescribing and Administration Guideline; 2019.
Royal Berkshire NHS Foundation Trust iron deficiency anaemia in Maternity—Guideline for the management of (GL783); 2020.
Department of Health & Human Services, State Government of Victoria, Australia Guidelines for Perioperative Care in Elective Colorectal Surgery: Enhanced Recovery After Surgery (ERAS) Society Recommendations: 2018 https://www2.health.vic.gov.au/hospitals-and-health-services/patient-care/speciality-diagnostics-therapeutics/blood-matters/patient-blood-management/guiding-principles-for-iron.
Auerbach M Treatment of iron deficiency anemia in adults; 2020, https://www.uptodate.com/contents/treatment-of-iron-deficiency-anemia-in-adults/print?search=iron.
Medway NHS Foundation Trust IV Iron Integrated Care Pathway (ICP), 2016.
International Society of Blood Transfusion (ISBT) Pre-operative optimisation of haemoglobin; 2016.
University Hospital Southampton Preoperative optimisation of anaemia for surgery (POAS) pathway at UHS—The Monofer Quick Reference Guide, Aug. 2017.
Aksan A, Işik H, Radeke HH, Dignass A, Stein J. Letter: inconsistency in reporting of hypophosphataemia after intravenous iron-authors' reply. Aliment Pharmacol Ther. 2017;46(6):643-644. doi: 10.1111/apt.14254.
Aksan, et al. "Systematic review with network meta-analysis: comparative efficacy and tolerability of different intravenous iron formulations for the treatment of iron deficiency anaemia in patients with inflammatory bowel disease," Aliment Pharmacol Ther. May 2017;45(10):1303-1318.
Bager P, Hvas CL, Dahlerup JF. Drug-specific hypophosphatemia and hypersensitivity reactions following different intravenous iron infusions. Br J Clin Pharmacol. 2017;83(5):1118-1125. doi:10.1111/bcp.13189.
Blazevic A, Hunze J, Boots JM. Severe hypophosphataemia after intravenous iron administration. Neth J Med. 2014;72(1):49-53.
Bregman, et al. "Experience with intravenous ferric carboxymaltose in patients with iron deficiency anemia," Ther Adv Hematoi. Apr. 2014;5(2):48-60.
Evstatiev, et al. "FERGIcor, a randomized controlled trial on ferric carboxymaltose for iron deficiency anemia in inflammatory bowel disease," Gastroenterology. Sep. 2011;141(3):846-853.e1-2.
Holm C, Thomsen LL, Norgaard A, Langhoff-Roos J. Single-dose intravenous iron infusion versus red blood cell transfusion for the treatment of severe postpartum anaemia: a randomized controlled pilot study. Vox Sang. 2017;112(2):122-131. doi:10.1111/vox.12475.
Huang LL, Lee D, Troster SM, et al. A controlled study of the effects of ferric carboxymaltose on bone and haematinic biomarkers in chronic kidney disease and pregnancy. Nephrol Dial Transplant. 2018;33(9):1628-1635. doi:10.1093/ndt/gfx310.
Hussain I, Bhoyroo J, Butcher A, Koch TA, He A, Bregman DB."Direct Comparison of the Safety and Efficacy of Ferric Carboxymaltose versus Iron Dextran in Patients with Iron Deficiency Anemia." Anemia. 2013;2013:169107. doi:10.1155/2013/169107.
Sari V, Atiqi R, Hoorn EJ, Heijboer AC, van Gelder T, Hesselink DA. Ferric carboxymaltose-induced hypophosphataemia after kidney transplantation. Neth J Med. 2017;75(2):65-73.
Schaefer B, Glodny B, Zoller H. Blood and Bone Loser. Gastroenterology. 2017;152(6):e5-e6. doi:10.1053/j.gastro.2016.09.050.
Schaefer B, Würtinger P, Finkenstedt A, et al. Choice of High-Dose Intravenous Iron Preparation Determines Hypophosphatemia Risk. PLoS One. 2016;11(12):e0167146. Published Dec. 1, 2016. doi:10.1371/journal.pone.0167146.
Seid MH, Derman RJ, Baker JB, Banach W, Goldberg C, Rogers R. Ferric carboxymaltose injection in the treatment of postpartum iron deficiency anemia: a randomized controlled clinical trial. Am J Obstet Gynecol. 2008;199(4):435.e1-435.e4357. doi:10.1016/j.ajog.2008.07.046.
Stein J, Walper A, Klemm W, Farrag K, Aksan A, Dignass A. Safety and efficacy of intravenous iron isomaltoside for correction of anaemia in patients with inflammatory bowel disease in everyday clinical practice. Scand J Gastroenterol. 2018:53(9):1059-1065. doi:10.1080/00365521.2018.1498914.
Stöhr R, Sandstede L, Heine GH, Marx N, Brandenburg V. High-Dose Ferric Carboxymaltose in Patients With HFrEF Induces Significant Hypophosphatemia. J Am Coll Cardiol. 2018;71(19):2270-2271. doi:10.1016/j.jacc.2018.03.448.

(56) References Cited

OTHER PUBLICATIONS

Strauss WE, Franklin Adkinson N, Macdougail IC, et al. A response by Strauss et al. to "a comment on the comparative safety of intravenous ferumoxytol versus ferric carboxymaltose in iron deficiency anemia". Am J Hematol. 2018;93(9):E232-E233. doi:10.1002/ajh.25200.

Van Wyck DB, Mangione A, Morrison J, Hadley PE, Jehle JA, Goodnough LT. Large-dose intravenous ferric carboxymaltose injection for iron deficiency anemia in heavy uterine bleeding: a randomized, controlled trial. Transfusion. 2009;49(12):2719-2728. doi:10.1111/j.1537-2995.2009.02327.x.

Vandemergel X, Vandergheynst F. Potentially life-threatening phosphate diabetes induced by ferric carboxymaltose injection: a case report and review of the literature. Case Rep Endocrinol. 2014;2014:843689. doi:10.1155/2014/843689.

Zoller H, Schaefer B, Glodny B. Iron-induced hypophosphatemia: an emerging complication. Curr Opin Nephrol Hypertens. 2017;26(4):266-275. doi: 10.1097/MNH.0000000000000329.

Center for Drug Evaluation and Research Application No. 203565Orig1s000; Summary Review, 2013, 10 pages.

Schubert, Laurie, and Hector F DeLuca. "Hypophosphatemia is responsible for skeletal muscle weakness of vitamin D deficiency." Archives of biochemistry and biophysics vol. 500,2 (2010): 157-61. doi:10.1016/j.abb.2010.05.029.

Tiosano, Dov, and Ze'ev Hochberg. "Hypophosphatemia: the common denominator of all rickets." Journal of bone and mineral metabolism vol. 27,4 (2009): 392-401. doi:10.1007/s00774-009-0079-1.

Schober, Hans-Christof et al. "Selective blood sampling for FGF-23 in tumor-induced osteomalacia." Endocrinology, diabetes & metabolism case reports vol. 2017 17-0006. Oct. 6, 2017, doi: 10.1530/EDM-17-0006.

Whyte, Michael P., and Rajesh V. Thakker. "Rickets and osteomalacia." Medicine 37.9 (2009): 483-488.

Park, Wan et al. "Serum phosphate levels and the risk of cardiovascular disease and metabolic syndrome: a double-edged sword." Diabetes research and clinical practice vol. 83,1 (2009): 119-25. doi:10.1016/j.diabres.2008.08.018.

Christopoulou, E C et al. "Phosphate imbalance in patients with heart failure." Heart failure reviews vol. 22,3 (2017): 349-356. doi:10.1007/s10741-017-9615-6.

Aubier, M et al. "Effect of hypophosphatemia on diaphragmatic contractility in patients with acute respiratory failure." The New England journal of medicine vol. 313,7 (1985): 420-4. doi:10.1056/NEJM198508153130705.

Fukumoto, Seiji. "FGF23-related hypophosphatemic rickets/osteomalacia: diagnosis and new treatment." Journal of molecular endocrinology vol. 66,2 (2021): R57-R65. doi:10.1530/JME-20-0089.

"BMJ Best Practice Osteomalacia" BMJ Publishing Group Ltd., Jan. 5, 2018, 34 pages total.

Edmonston, Daniel, and Myles Wolf. "FGF23 at the crossroads of phosphate, iron economy and erythropoiesis." Nature reviews. Nephrology vol. 16,1 (2020): 7-19. doi:10.1038/s41581-019-0189-5.

Florenzano, Pablo et al. "Tumor-Induced Osteomalacia." Calcified tissue international vol. 108,1 (2021): 128-142. doi:10.1007/s00223-020-00691-6.

Wolf, Myles, et al., "OR13-3 Effects of Iron Isomaltoside versus Ferric Carboxymaltose on Hormonal Control of Phosphate Homeostasis: The PHOSPHARE-IDA04/05 Randomized Controlled Trials." Journal of the Endocrine Society, vol. 3, Issue Supplement_1, Apr.-May 2019, OR13-3, https://doi.org/10.1210/js.2019-OR13-3.

Iqbal TH, et al. "Phosephare studies: Important changes in phosphate homeostasis and bone metabolism after IV iron." Poster presented at the BSG Annual Meeting, Glasgow, Jun. 17-20, 2019.

Iqbal T, et al. "Phosphare Studies: Important Changes In Phosphate Homeostasis and Bone Metabolism After IV Iron." Abstract PTH-137, GUT 2019;68(Suppl 2):A103-A104. 10.1136/gutjnl-2019-BSGAbstracts.196.

Wolf, Myles et al. "Effects of Iron Isomaltoside vs Ferric Carboxymaltose on Hypophosphatemia in Iron-Deficiency Anemia: Two Randomized Clinical Trials." JAMA vol. 323,5 (2020): 432-443. doi:10.1001/jama.2019.22450.

"Ferinject (ferric carboxymaltose)" Summary of Product Characteristics (SmPC)—History—(emc), updated Nov. 4, 2020 https://www.medicines.org.uk/emc/product/5910/smpc/history; 24 pages total.

Anker, Stefan D et al. "Ferric carboxymaltose in patients with heart failure and iron deficiency." The New England journal of medicine vol. 361,25 (2009): 2436-48. doi:10.1056/NEJMoa0908355; includes supplementary Appendix.

Ponikowski, Piotr et al. "Ferric carboxymaltose for iron deficiency at discharge after acute heart failure: a multicentre, double-blind, randomised, controlled trial." Lancet (London, England) vol. 396, 10266 (2020): 1895-1904. doi:10.1016/S0140-6736(20)32339-4.

Rosano, Giuseppe et al. "A Pooled Analysis of Serum Phosphate Measurements and Potential Hypophosphataemia Events in 45 Interventional Trials with Ferric Carboxymaltose." Journal of clinical medicine vol. 9,11 3587. Nov. 6, 2020, doi:10.3390/jcm9113587.

Schaefer, Benedikt et al. "Risk Factors for and Effects of Persistent and Severe Hypophosphatemia Following Ferric Carboxymaltose." The Journal of clinical endocrinology and metabolism vol. 107,4 (2022): 1009-1019. doi:10.1210/clinem/dgab852.

"Ferric carboxymaltose (Ferinject ▼): risk ofsymptomatic hypophosphataemia leading to osteomalacia and fractures" https://www.gov.uk/drug-safety-update, dated Nov. 16, 2020. 5 pages total.

"INJECTAFER® (ferric carboxymaltose injection), for intravenous use Initial U.S. Approval: 2013" FDA label, revised Apr. 2018. 12 pages total.

"INJECTAFER® (ferric carboxymaltose injection), for intravenous use Initial U.S. Approval: 2013" FDA label, revised Feb. 2020. 14 pages total.

"Position of the Co-ordination Group for Mutual Recognition and Decentralised Procedures for human use on Periodic Safety Update Reports for Active substance(s): iron (parenteral preparations, except for iron dextran)" Co-ordination group for Human Use, European Medicines Agency, Jul. 23, 2020. 8 pages total.

Zoller, H., et al. "Pooled analysis of the Phosphare-IDA 04/05 studies: findings relevant to respiratory muscle function." Poster presented at the 20th Annual NATA Symposium, Berlin, Apr. 4-5, 2019.

* cited by examiner

| Analysis of Primary Endpoint: Hypophosphatemia at Any Time from Baseline to Day 35 - Safety Analysis Set | | | | | | |
|---|---|---|---|---|---|---|
| | N | n | Rate | Rate (%) | 95% CI | Difference | 95% CI | P-value |
| Safety Analysis Set | | | | | | |
| Treatment | | | | | | |
| Iron Isomaltoside | 63 | 63 | 5/63 | 7.9 | (2.6; 17.6) | | |
| Ferric Carboxymaltose | 60 | 59 | 45/60 | 75.0 | (62.1; 85.3) | | |
| Adjusted treatment difference* | | | | | | |
| Iron Isomaltoside - Ferric Carboxymaltose | | | | | | -67.0 | (-77.4; -51.5) | <0.0001 |

N: Number in analysis set, n: Number with non-imputed post-baseline values, Rate: Number of subjects experiencing the event at least once/N, CI: Confidence interval, Rate with exact 95% CI
* Hypophosphatemia: Phosphate < 2.0 mg/dL
* Rate difference with 95% Newcombe CI adjusted for stratum using the Cochran-Mantel-Haenszel method

Figure 1

| Analysis of Primary Endpoint: Hypophosphatemia at Any Time from Baseline to Day 35 – Safety Analysis Set | | | | | | |
|---|---|---|---|---|---|---|
| Safety Analysis Set | N | n | Rate | Rate (%) | Difference | 95% CI | P-value |
| Treatment | | | | | | |
| Iron Isomaltoside | 62 | 61 | 5/62 | 8.1 | (2.7; 17.8) | | |
| Ferric Carboxymaltose | 57 | 56 | 42/57 | 73.7 | (60.3; 84.5) | | |
| Adjusted treatment difference* | | | | | | |
| Iron Isomaltoside – Ferric Carboxymaltose | | | | | -65.8 | (-76.6; -49.8) | <0.0001 |

N: Number in analysis set, n: Number with non-imputed post-baseline values, Rate: Number of subjects experiencing the event at least once;N, CI: Confidence Interval, Rate with exact 95% CI Hypophosphatemia: Phosphate < 2.0 mg/dL
* Rate difference with 95 % Newcombe CI adjusted for stratum using the Cochran-Mantel-Haenszel method

Figure 2

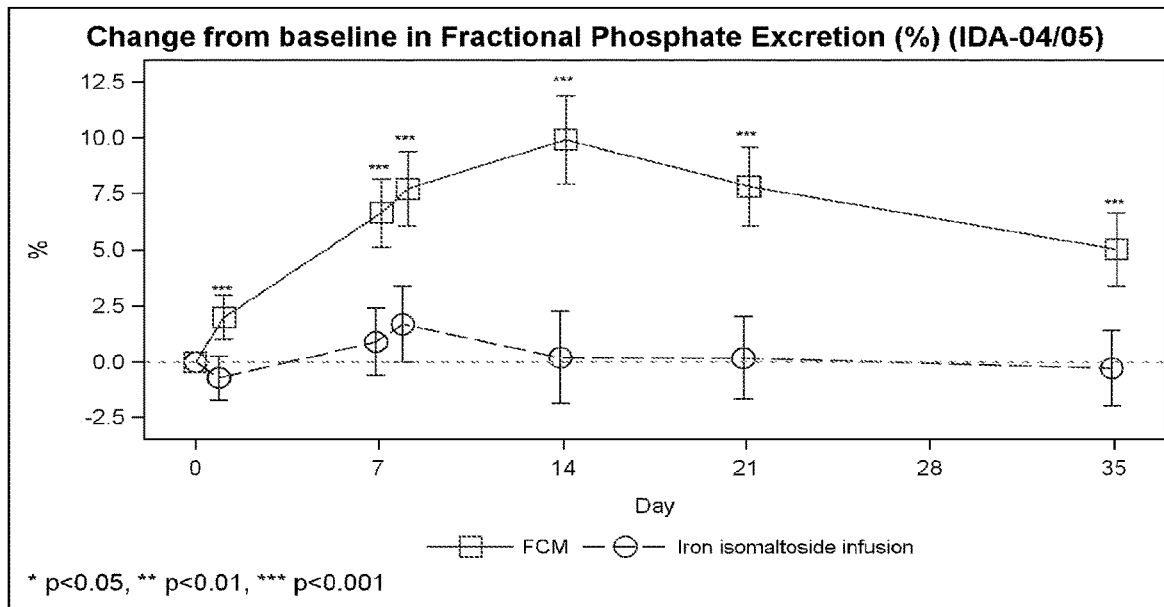
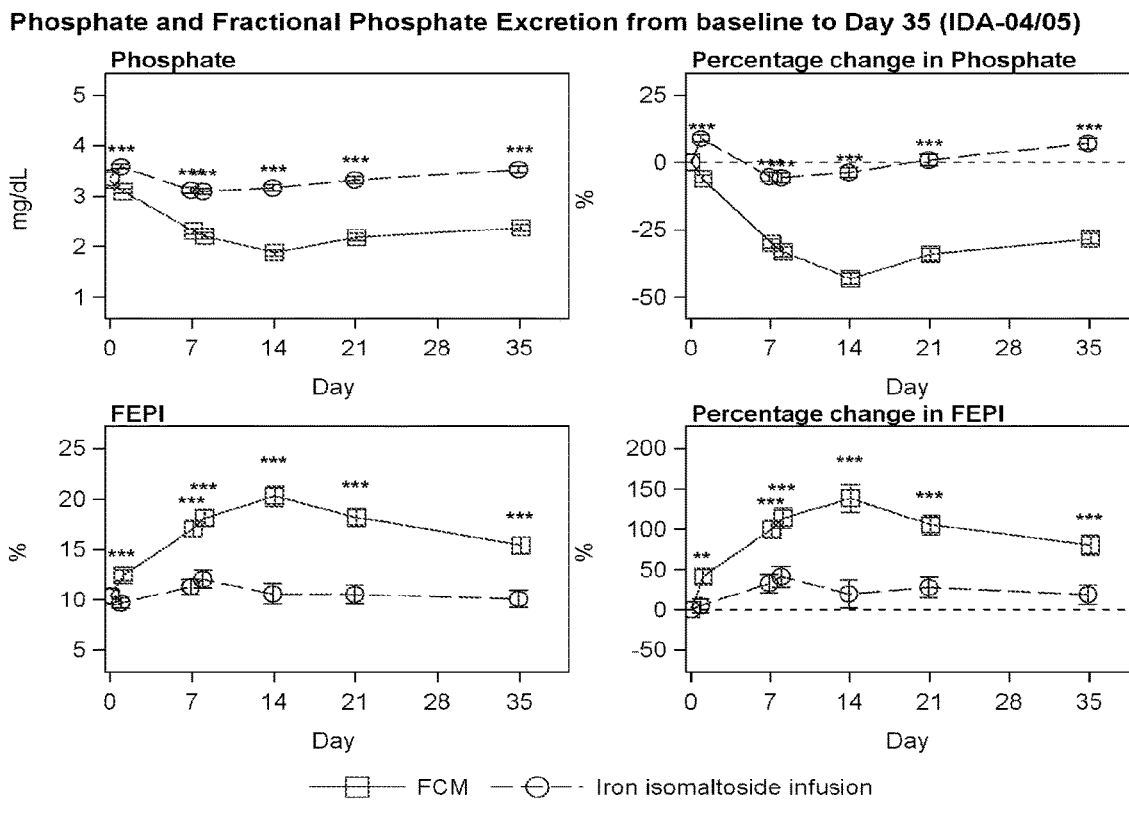
Figure 10

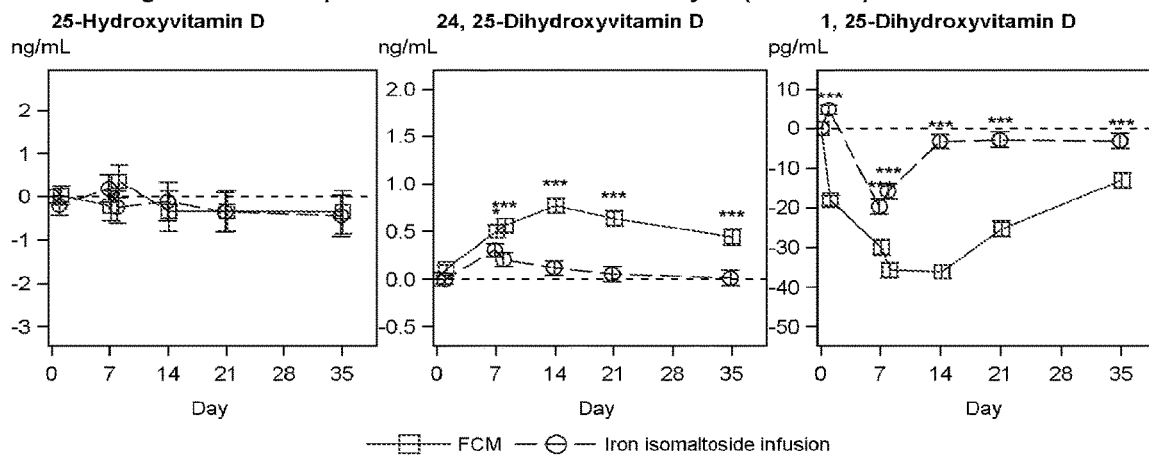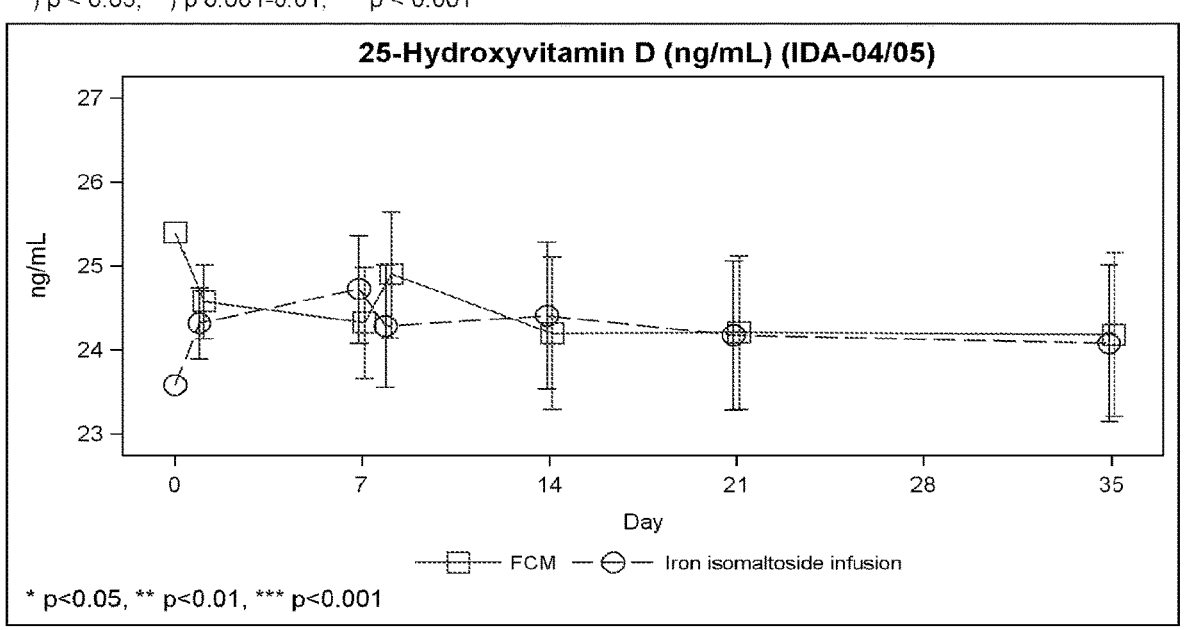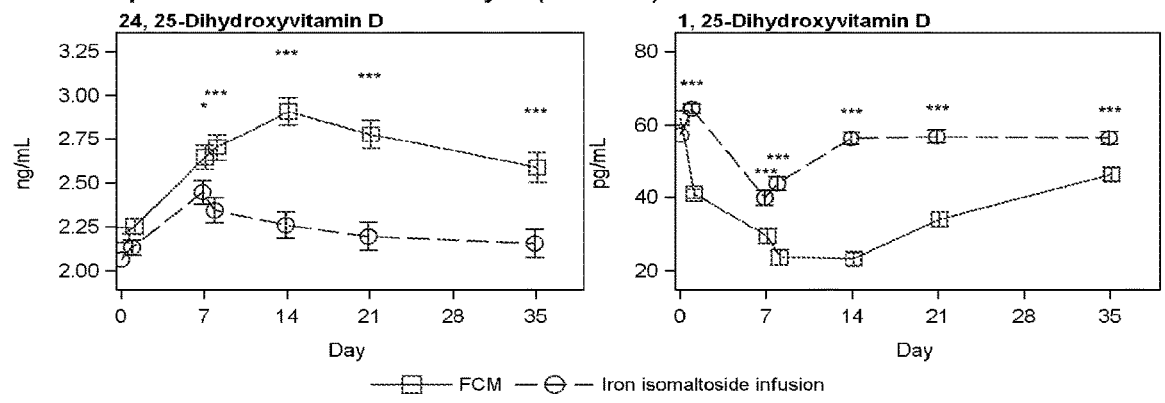
Figure 11

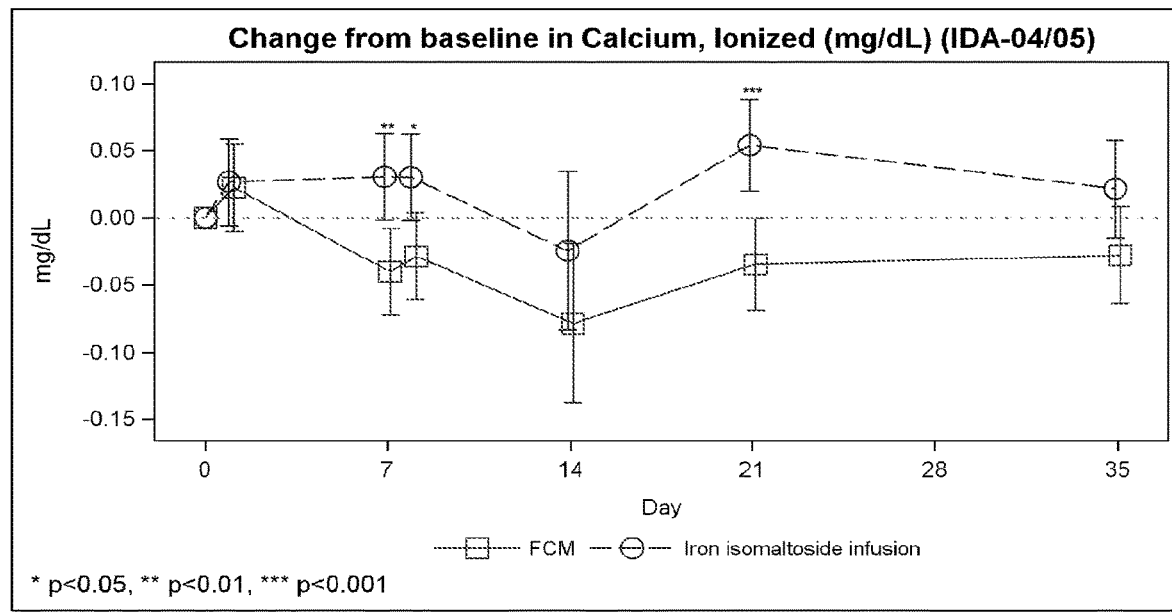
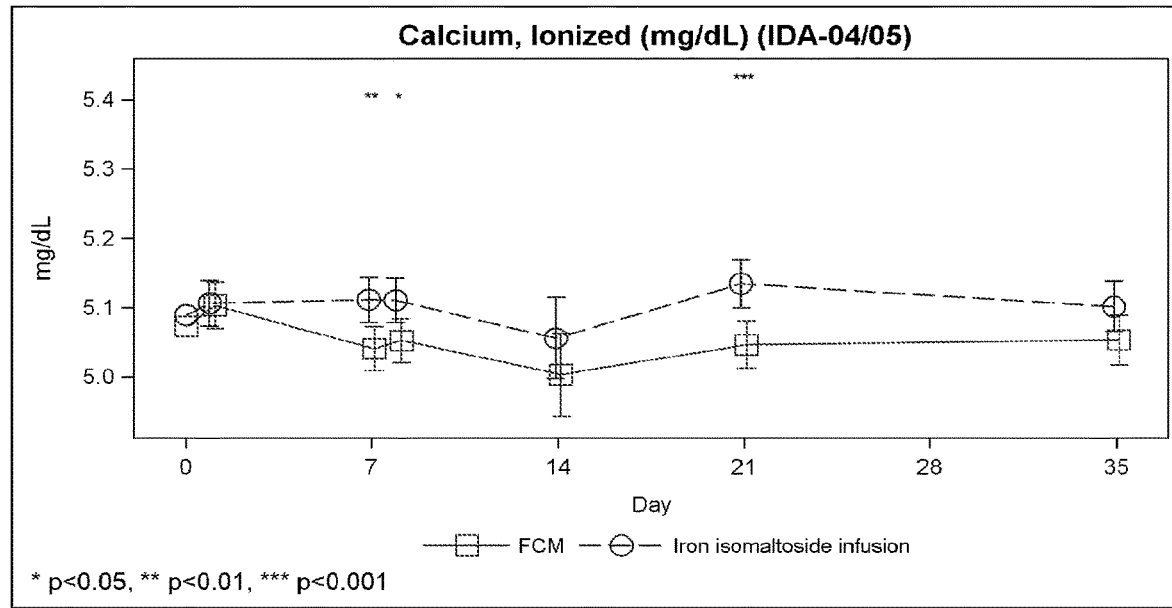
Figure 13

TREATING IRON DEFICIENCY WITH FERRIC CARBOXYMALTOSE

CROSS-REFERENCE TO RELATED APPLICATIONS

This application is a divisional of U.S. application Ser. No. 16/822,911, filed Mar. 18, 2020, which is a divisional of Patent Cooperation Treaty (PCT) Appl. No. PCT/EP2019/079528 filed Oct. 29, 2019 which claims priority to European Patent Application Nos. EP 18203223.5 filed Oct. 29, 2018 and EP 18203818.2 filed Oct. 31, 2018, each of which is hereby incorporated by reference herein in its entirety.

FIELD OF THE INVENTION

The present invention relates to the field of treating iron deficiency with IV iron carbohydrate complexes, monitoring or identifying subjects to determine their eligibility for being administered said IV iron carbohydrate complexes, and combining said IV iron carbohydrate complexes with additional drugs in order to mitigate or reduce side effects induced by the IV iron carbohydrate complexes.

BACKGROUND

Iron deficiency (ID) impairs the body's ability to produce hemoglobin, the key oxygen transporter, and impairs the function of key energy (ATP) producing enzymes. Symptoms consequently include fatigue and other signs of energy deprivation such as rapid heartbeat, shortness of breath, and chest pain.

ID has serious consequences. In chronic heart failure (CHF) patients, the risk of death or hospitalization is increased in patients with ID relative to patients with normal iron status. Quality of life (QoL) is severely affected and improves rapidly upon restoration of iron stores. Patients with ID or IDA undergoing surgery have poor outcomes—in part due to greater risk of blood transfusions. Maternal iron deficiency is associated with increased risk of pre-term birth and impaired fetal brain development.

Iron deficiency anemia (IDA) develops when iron stores are depleted. It is widespread. About 1 billion people worldwide suffer from IDA according to the WHO. 4.5 million patients are diagnosed with IDA. Daily oral iron is the first line therapy for most IDA patients but often fails due to lack of compliance, lack of efficacy and side effects.

High dose intravenous (IV) iron is an attractive treatment option. Patients typically require 1-3 grams of iron per year and high dose IV iron effectively and rapidly improves symptoms and increases hemoglobin levels. High dose IV iron allows treatment in one or few visits and IV iron is the only option for patients failing oral iron.

Ferric carboxymaltose (FCM) belongs to a new generation of high dose IV iron products. While older low dose products (ferric gluconate and iron sucrose) required 5-20 visits, these new generation products allow for iron correction in one or two visits by fast infusion of the product.

Moderate and transient decreases in serum phosphate (S-phosphate) have been observed for all iron complexes upon IV administration in humans to treat iron deficiency or iron deficiency anemia. This general phenomenon is believed by some to be associated with the consumption of phosphate in erythropoiesis, a primary intended effect of parenteral iron therapy. See, for instance, Van Wyck et al., 2009. Others have favored a theory of phosphate wasting which postulates that the renal phosphate loss could be the consequence of proximal tubular dysfunction due to a direct toxic effect of IV iron on proximal renal tubular cells. Prats et al., 2013.

Ferric carboxymaltose (FCM) is a very commonly used iron carbohydrate complex to treat patients with ID or IDA who are not on dialysis. It is commercially available in the United States under the tradename Injectafer® and in the European Union and many other countries under the tradename Ferinject®. A typical treatment regimen of FCM consists either of two doses of 750 mg of elemental iron given as intravenous infusion one week apart (this is the approved use according to the US label) or as an infusion of 1000 mg of elemental iron followed by an additional dose of 500-1000 mg one week after (this is the approved use according to its EU label).

FCM has been shown to lead to a larger and longer reduction in serum phosphate as compared to iron dextran (Wolf et al., 2013), iron sucrose (WO2013/134273 A1) and iron isomaltoside 1000 (Bager et al., 2016, Schaefer et al., 2016, Zoller et al., 2017) and as a result a higher prevalence of hypophosphatemia, i.e., the condition characterized by too low serum phosphate.

Nonetheless, although there are individual case reports on hypophosphatemia resulting from the treatment with FCM (Anand G, Schmid C, BMJ Case rep 2017) and subsequent bone complications such as osteomalacia occurring months thereafter (see, for instance, Schaefer et al. 2017; Klein et al. 2018), such findings have been actively disputed by the majority of publications or characterized as so rare to be a curiosity. A large number of scientific publications on the use of FCM describe how the associated hypophosphatemia is considered to be transient, asymptomatic and/or clinically irrelevant. See, for instance, Aksan et al., 2007; Bregman et al., 2014; Charytan et al., 2013; Evstatiev, 2011; Hussain et al., 2013; Ikuta et al., 2018; Prats et al., 2013; Qunibi et al., 2011; Sari et al., 2017; Seid et al., 2008; Stein et al., 2018; Van Wyck et al., 2009. This perspective has so far been supported by the absence of studies demonstrating any short-term clinical impacts of the lowered phosphate levels despite the changes in biochemical parameters.

US and EU regulators have so far also taken the position that FCM-associated hypophosphatemia is transient, asymptomatic and clinically irrelevant. Although the U.S. FDA in a 2007 non-approval letter listed clinically important hypophosphatemia as one of three potential safety risks that would need to be resolved through additional clinical data in order to verify the safety of the product, the subsequent submission of data by the sponsor of Injectafer® led the agency to conclude in 2013 that all the clinical (efficacy and safety) issues brought forth in the non-approval letter including the issue of clinically important hypophosphatemia had been satisfactorily resolved (U.S. Federal Drug Administration Center for drug evaluation and research, application number: 203565Orig1s000, summary review 2013). The view that hypophosphatemia associated with FCM is mild and transient is also reflected in the currently approved labels, which list hypophosphatemia as a side effect, but do not provide particular warnings related to hypophosphatemia, neither in terms of short- or long-term consequences. On the contrary, aside from listing it as a side effect the only mention of hypophosphatemia in the EU Summary of Product Characteristics (SmPC) which forms part of the regulatory approval of FCM in Europe is the following statement: "In clinical trials, the minimum serum phosphorous values were obtained after approximately 2 weeks, and 4 to 12 weeks following Ferinject treatment the values had returned to those within the range of baseline".

Fibroblast growth factor 23 (FGF23) is an osteocyte-derived hormone that regulates phosphate and vitamin D homeostasis. It undergoes proteolytic cleavage and as a result a mix of uncleaved, i.e. intact FGF23 (iFGF23), and its cleavage fragments are found in vivo. Because reduced serum phosphate in response to intravenous iron was suggested to be mediated by an acute increase in FGF23, Wolf et al. examined the effects of iron deficiency and its rapid correction on C-terminal and intact FGF23 levels in women with iron deficiency anemia secondary to heavy uterine bleeding. Their findings suggested that iron deficiency increases C-terminal FGF23 (cFGF23) levels, and that FCM temporarily increased iFGF23 levels and reduced serum phosphate. Wolf et al., 2013; WO2013/134273 A1.

We have surprisingly found that contrary to the general understanding in the art, treatment with FCM according to current practice leads to direct clinical consequences such as reduced muscle function and increased bone turnover. Furthermore, we have found that the current practice related to repeated dosing of FCM one week apart leads to an auto-synergistic impact on iFGF23, with the second dose leading to a 2-3 fold higher increase than the first dose.

Based on this understanding, there is clearly a need for improved methods of using FCM in the treatment of the underlying ID or IDA, which methods substantially decrease the risk of iFGF23-induced consequences such as reduced muscle function and increased bone turnover. These and other iFGF23-induced metabolic, nutritional and musculo-skeletal consequences of FCM treatment are hereinafter referred to as the iFGF23-mediated or iFGF23-induced side effects.

SUMMARY

In one aspect of this invention, the treatment with ferric carboxymaltose can be completed without loss of efficacy, but with a reduced risk of iFGF23-mediated side effects by adjusting the timing and/or the amount of FCM administered in order to avoid auto-synergistic effects.

In a second aspect of this invention, patients are selected for treatment with ferric carboxymaltose not only based on the criteria commonly used to define eligibility for IV iron, i.e. diagnosis of ID or IDA and a potential lack of the ability to tolerate or absorb oral iron, but also based on being less likely to suffer from iFGF23-mediated side effects.

In a third aspect of this invention, a subject who has been administered a first dose of ferric carboxymaltose is monitored to determine if or when the subject is eligible for being administered a second dose of ferric carboxymaltose.

In a fourth aspect of this invention, a subject having a reduced risk for FGF23-mediated side effects is identified.

In a fifth aspect of this invention, ferric carboxymaltose is combined with supporting drugs to mitigate or reduce the impact of iFGF23-mediated side effects.

In line with these aspects, the present invention in particular relates to therapeutic methods of treating iron deficiency which comprise administering ferric carboxymaltose according to defined regimens and/or to selected subgroups of subjects; diagnostic methods for monitoring subjects who have been administered a first dose of FCM to adjust the timing and/or the amount of further FCM administration, or for identifying subjects suitable for the therapeutic methods of the invention; and combinations of FCM with other drugs that mitigate or reduce the impact of iFGF23-mediated side effects.

In a first embodiment of said first aspect, the present invention relates to a method of treating iron deficiency, which comprises administering a first dose and a second dose of ferric carboxymaltose, wherein the time between the first and the second dose is at least 10 days.

In a second embodiment of said first aspect, the present invention relates to a method of treating iron deficiency, which comprises administering a first dose and a second dose of ferric carboxymaltose, wherein the first and the second dose each do not exceed 500 mg of elemental iron.

In a third embodiment of said first aspect, the present invention relates to a method of treating iron deficiency, which comprises administering one or more doses of ferric carboxymaltose, wherein the total amount of elemental iron administered within a period of 12 months does not exceed 5000 mg.

In a first embodiment of said second aspect, the present invention relates to a method of treating iron deficiency which comprises administering ferric carboxymaltose, wherein the subject having a reduced risk for FGF23-mediated side effects has blood parameters as disclosed herein.

In a second embodiment of said second aspect, the present invention relates to a method of treating iron deficiency which comprises administering ferric carboxymaltose, wherein the subject having a reduced risk for FGF23-mediated side effects is characterized by the absence of exclusion criteria as disclosed herein.

In a third embodiment of said second aspect, the present invention relates to a method of treating iron deficiency which comprises administering ferric carboxymaltose, wherein the subject having a reduced risk for FGF23-mediated side effects is characterized by respiratory capacity as disclosed herein.

In a first embodiment of said third aspect, the present invention relates to a method of monitoring a subject who has been administered a first dose of ferric carboxymaltose, comprising determining in a biological sample obtained from the subject at least one blood or urine parameter selected from the group consisting of (1) serum phosphate level, (2) serum vitamin D level, (3) serum ionized calcium level, (4) serum PTH level and (5) fractionary urinary phosphate excretion, wherein the subject is eligible for being administered a second dose of ferric carboxymaltose if the at least one blood or urine parameter is as disclosed herein.

In a second embodiment of said third aspect, the present invention relates to a method of monitoring a subject who has been administered a first dose of ferric carboxymaltose, comprising determining in a biological sample obtained from the subject at least one blood parameter selected from the group consisting of (1) serum Bone Specific Alkaline Phosphatase level; (2) serum Alkaline Phosphatase level, (3) serum N-terminal Propeptide of Type I Collagen (PINP) level and (4) serum Carboxy-terminal Collagen Crosslinks (CTx) level, wherein the subject is eligible for being administered a second dose of ferric carboxymaltose if the at least one blood parameter is as disclosed herein.

In a third embodiment of said third aspect, the present invention relates to a method of monitoring a subject who has been administered a first dose of ferric carboxymaltose, comprising determining the respiratory capacity of the subject, wherein the subject is eligible for being administered a second dose of ferric carboxymaltose if the respiratory capacity is as disclosed herein.

In a first embodiment of said fourth aspect, the present invention relates to a method of identifying a subject having a reduced risk for FGF23-mediated side effects, comprising determining in a biological sample obtained from the subject at least one blood or urine parameter selected from the group consisting of (1) serum phosphate level, (2) serum vitamin D level, (3) serum ionized calcium level, (4) serum PTH level and (5) fractionary urinary phosphate excretion, wherein the subject has a reduced risk for FGF23-mediated side effects if the at least one blood or urine parameter is as disclosed herein.

In a second embodiment of said fourth aspect, the present invention relates to a method of identifying a subject having a reduced risk for FGF23-mediated side effects, comprising determining in a biological sample obtained from the subject at least one blood parameter selected from the group consisting (1) serum Bone Specific Alkaline Phosphatase level; (2) serum Alkaline Phosphatase level, (3) serum N-terminal Propeptide of Type I Collagen (PINP) level and (4) serum Carboxy-terminal Collagen Crosslinks (CTx) level, wherein the subject has a reduced risk for FGF23-mediated side effects if the at least one blood parameter is as disclosed herein.

In a third embodiment of said fourth aspect, the present invention relates to a method of identifying a subject having a reduced risk for FGF23-mediated side effects, comprising determining whether the subject is characterized by one or more and in particular all of the following exclusion criteria:
  (1) having undergone bariatric surgery;
  (2) obesity;
  (3) cardiac conditions with increased risks of arrhythmias;
  (4) primary or secondary hyperparathyroidism;
  (5) pulmonary disorders such as asthma or chronic obstructive pulmonary disease (COPD)
  (6) genetic diseases leading to hypophosphatemia such as X-linked hypophosphatemia, autosomal dominant hypophosphatemic rickets, autosomal recessive hypophosphatemic rickets;
  (7) secondary hypophosphatemia or tumor induced hypophosphatemia;
  (8) disorders of the bone, such as for example osteoporosis or osteomalacia; and
  (9) being scheduled for surgery within 1 day to two months of the iron administration, wherein the subject has a reduced risk for FGF23-mediated side effects if the subject is characterized by the absence of one or more and in particular all of the exclusion criteria.

In a fourth embodiment of said fourth aspect, the present invention relates to a method of identifying a subject having a reduced risk for FGF23-mediated side effects, comprising determining the respiratory capacity of the subject, wherein the subject has a reduced risk for FGF23-mediated side effects if the respiratory capacity is as disclosed herein.

In a first embodiment of said fifth aspect, the present invention relates to a combination of ferric carboxymaltose with one or more additional drugs selected from the group consisting of:
  (1) vitamin Ds, such as calcitriol;
  (2) phosphates, such as glucose-1-phosphate, calcium phosphate or sodium phosphate; and
  (3) anti-FGF23 antagonistic antibodies, such as burosumab.

BRIEF DESCRIPTION OF THE DRAWINGS

FIG. 1 is a table summarizing the analysis of the occurrence of hypophosphatemia (primary endpoint) for study IDA-04.

FIG. 2 is a table summarizing the analysis of the occurrence of hypophosphatemia (primary endpoint) for study IDA-05.

FIG. 10 shows the change of fractional urinary phosphate excretion over time (IDA-04 and IDA-05 combined).

FIG. 11 shows the mean change from baseline and absolute change of vitamin D levels over time (IDA-04 and IDA-05 combined).

FIG. 13 shows the change from baseline and absolute change of calcium ions over time (IDA-04 and IDA-05 combined).

DETAILED DESCRIPTION

Figure 3:
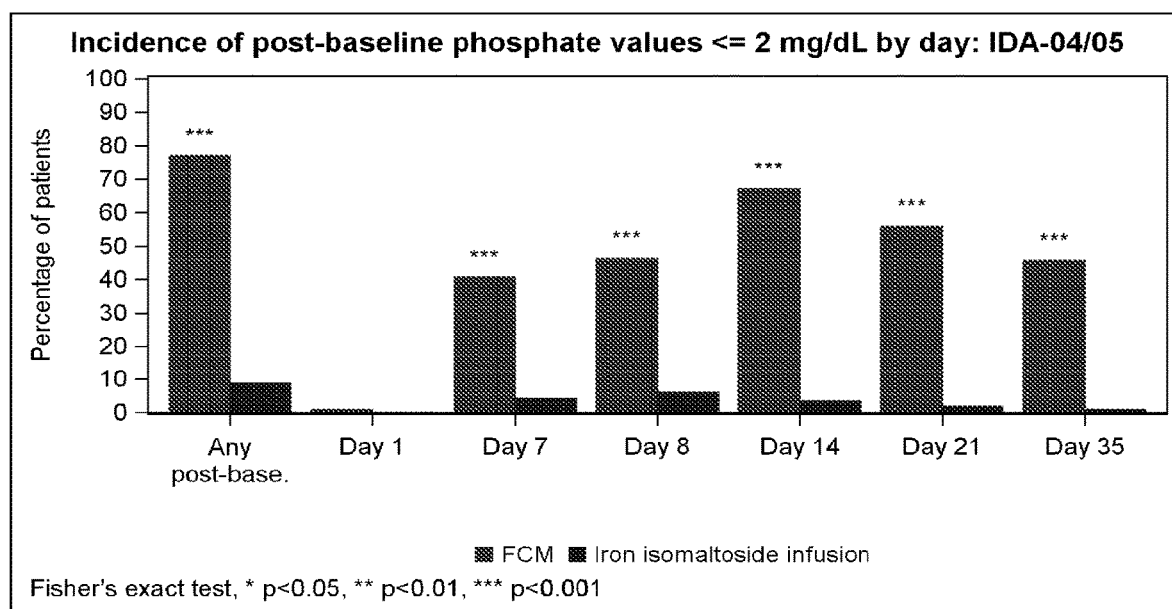
FIG. 3 shows the incidence of phosphate levels ≤2.0 mg/dL by visit (IDA-04 and IDA-05 combined; FCM: left-hand bars, right-hand bars).
Figure 4:
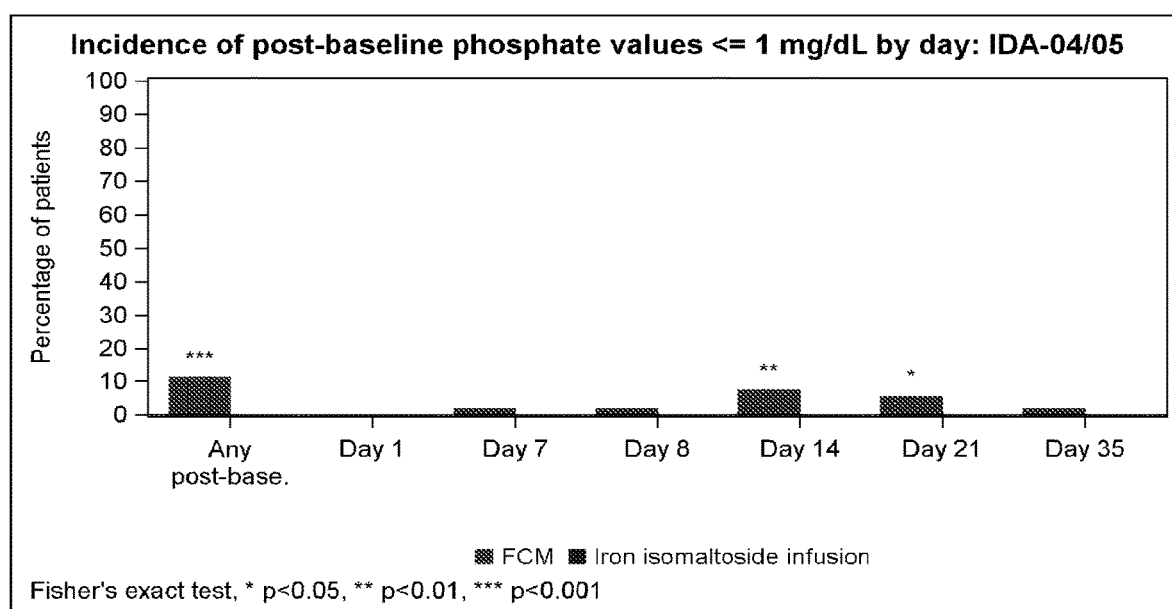
FIG. 4 shows the incidence of phosphate levels ≤1.0 mg/dL by visit (IDA-04 and IDA-05 combined; FCM: left-hand bars, IIM: right-hand bars).
Figure 5:
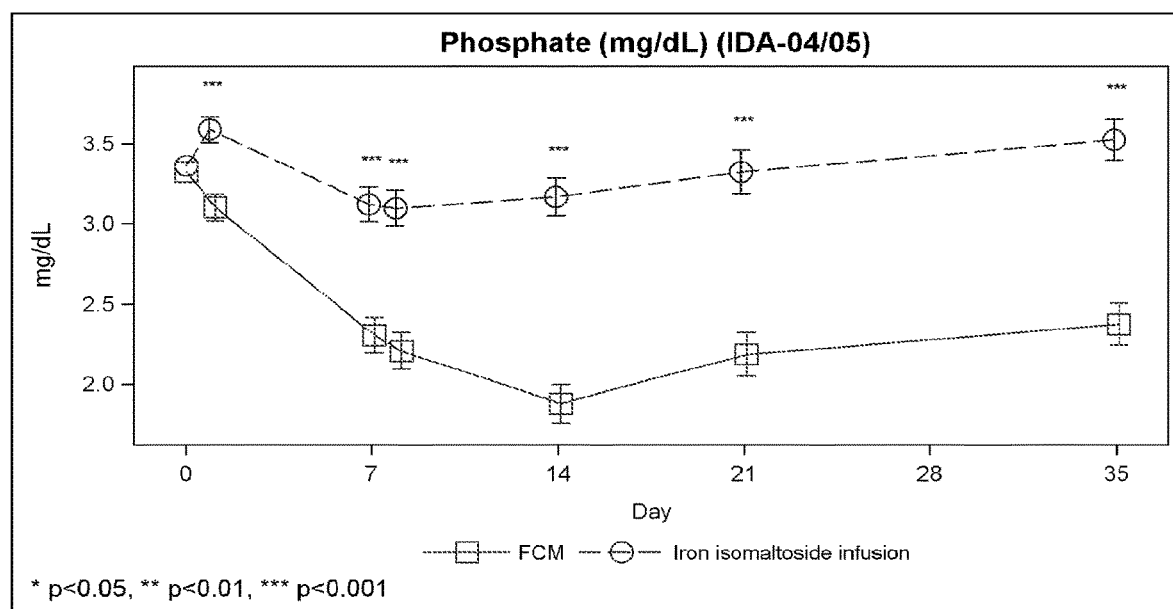
FIG. 5 shows the mean absolute phosphate levels over time (IDA-04 and IDA-05 combined).

Described herein are therapeutic methods of treating iron deficiency which comprise administering an iron carbohydrate complex, methods of monitoring a subject who has been administered a first dose of an iron carbohydrate complex, methods of identifying a subject suitable for the therapeutic methods of the invention, and combinations of an iron carbohydrate complex with additional drugs, wherein the iron carbohydrate complex induces a significant (e.g., statistically significant) increase of iFGF23 levels in subjects under treatment. The methods of the invention are thus applicable to complexes that share the mechanism of inducing significant increases in iFGF23 and which, as a result, can reduce serum phosphate levels and thus lead to hypophosphatemia. While this does not include the other IV iron drugs commonly used in Europe and the US, (such as iron sucrose (Venofer®), iron gluconate (Ferrlecit®), iron isomaltoside 1000 (Monofer®), or iron dextran (Cosmofer®/INFeD® and Dexferrum®), it does include certain complexes available in Asia-Pacific including iron saccharated oxide available in Japan as Fesin® (which despite similarity in name is distinct from iron sucrose in Venofer®), some species of iron polymaltose and above all ferric carboxymaltose (FCM). Results from clinical trials and case reports suggest that the highest risk for an iFGF23-mediated reduction of serum phosphate levels and the development of hypophosphatemia is associated with iron polymaltose, saccharated iron oxide, and above all ferric carboxymaltose. See, for instance, Wolf et al., 2013.

Accordingly, the preferred iron carbohydrate complex of this invention is ferric carboxymaltose (FCM). The term "ferric carboxymaltose" as used herein refers to colloidal complexes comprising iron, e.g., as iron oxide hydroxide, and carboxymaltose. Carboxymaltose is based on starch or starch derivatives that have been carboxylated, i.e., modified to include carboxy groups, for example through oxidation of the aldehyde end groups. A particular ferric carboxymaltose is obtainable by oxidizing maltodextrin, as described, for instance, in WO2007/081744 A1 as VIT-45 and WO2004/037865 A1. A preferred example of ferric carboxymaltose is commercially available in the United States under the tradename Injectafer® and in the European Union and many other countries under the tradename Ferinject®.

Definitions

In order that the present description may be more readily understood, certain terms are first defined. Additional definitions are set forth throughout the detailed description.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease.

A "subject" includes any human or nonhuman animal. The term "nonhuman animal" includes, but is not limited to, vertebrates such as nonhuman primates, sheep, dogs, and rodents such as mice, rats and guinea pigs. In preferred embodiments, the subject is a human. The terms, "subject" and "patient" are used interchangeably herein.

A "therapeutically effective amount" or "therapeutically effective dose" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

"Fibroblast growth factor 23 (FGF23)" is an osteocyte-derived hormone that regulates phosphate and vitamin D homeostasis. FGF23 undergoes proteolytic cleavage and as a result a mix of uncleaved, i.e. intact FGF23 (iFGF23), and its cleavage fragments are found in vivo. The intact form, iFGF23, is the active form in relation to phosphate metabolism where it controls the urinary excretion of phosphate, with increasing levels of iFGF23 leading to urinary wasting of phosphate. Two main types of antibody assays currently exist, one which captures only iFGF23 and another which binds to the C-terminal end of the hormone and therefore captures both iFGF23 and C-terminal fragments. The latter metric, cFGF23, is therefore a measure of the sum of intact FGF23 and C-terminal FGF23 fragments. Thus, two test related to FGF23 exist, iFGF23 and cFGF23, which have different interpretations.

"Hypophosphatemia" is a condition characterized by too low serum phosphate levels. The Common Terminology Criteria for Adverse Events (CTCAE) Version 4.0 provides four grades of hypophosphatemia.

| Grade 1 | Grade 2 | Grade 3 | Grade 4 | Grade 5 |
|---|---|---|---|---|
| <LLN-2.5 mg/dL | <2.5-2.0 mg/dL | <2.0-1.0 mg/dL | <1.0 mg/dL | Death |
| <LLN-0.8 mmol/L | <0.8-0.6 mmol/L | <0.6-0.3 mmol/L | <0.3 mmol/L | |

LLN is the lower limit of normal range used by a specific laboratory.

As used herein, unless specified otherwise, frequencies of hypophosphatemia refer to serum phosphate levels below 2 mg/dL.

The term "serum phosphate (S-phosphate)" as used herein refers to the level of inorganic phosphorus in serum blood as measured as an ammonium phosphomolybdate complex having the formula $(NH_4)_3[PO_4](MoO_3)_{12}$ formed by the reaction of inorganic phosphorous with ammonium molybdate in the presence of sulfuric acid. The complex is determined photometrically in the ultraviolet region (340 nm) of the spectrum using the Roche Modular and Cobas Analyzers.

The term "serum vitamin D" as used herein refers to the level of vitamin Ds, in particular 25-hydroxyvitamin D, 1,25-dihydroxyvitamin D, and 24,25-dihydroxyvitamin D, in blood serum as measured by Liquid Chromatography and Tandem Mass Spectrometry (LC-MS/MS).

The term "serum ionized calcium" as used herein refers to the level of calcium ions ($Ca^{2+}$) in blood serum as measured using the IL GEM Premier 3500 PAK cartridge. The central component is the sensor card, which provides a low volume, gas tight chamber in which the blood sample is presented to the sensors. The pH and electrolyte sensors are all based on the principle of ion-selective electrodes; that is, an electrical potential can be established across a membrane which is selectively permeable to a specific ion. The pH and electrolyte sensors are polyvinyl chloride (PVC) based ion selective electrodes, consisting of an internal Ag/AgCl reference electrode and internal salt layer. The potentials are measured against the card reference electrode.

The term "serum parathyroid hormone (PTH)" as used herein refers to the level of serum parathyroid hormone in blood serum as measured using a two-site sandwich immunoassay using direct chemiluminometric technology, which used constant amounts of two anti-human PTH antibodies. PTH, produced by the parathyroid gland, is the major circulating factor regulating extracellular calcium concentration. Abnormally low ionized calcium concentrations trigger the secretion of PTH. The PTH molecules bind to type 1 PTH receptors in target tissues and initiate a sequence of reactions that results in an increase in extracellular calcium concentrations. PTH stimulates osteoclastic bone resorption resulting in the release of calcium from bone. PTH stimulates transcellular calcium reabsorption from the renal tubules and stimulates the kidney to produce 1,25-dihydroxyvitamin D, which acts on the intestines to increase calcium reabsorption. In most clinical conditions, rising levels of extracellular calcium will suppress PTH secretion through a negative feedback mechanism.

The term "fractionary urinary excretion of phosphate (FEPi)" (sometimes abbreviated FEPO4) is a measure of how much phosphate is not re-absorbed from the pre-urine in the kidneys, i.e., how much phosphate ends up in the urine as a proportion of how much phosphate the subject has in the blood. It is calculated like this: FEPi=[PO4 (Urine)*Creatinine (Serum)]/[PO4 (Serum)*Creatinine (Urine)]*100. An FEPi of 10-20% (0.1-0.2 fraction) is usually considered to be normal; an FEPi<10% (<0.1 fraction) is usually considered to be low; and an FEPi>20% (>0.2 fraction) is usually considered to be high. Phosphate in urine is measured using the same methodology as for serum.

The term "serum Bone Specific Alkaline Phosphatase" as used herein refers to the level of Bone specific Alkaline Phosphatase in blood serum as measured using the Beckman-Coulter Ostase assay which is a one-step immunoenzymatic chemiluminescence assay using a mouse monoclonal antibody specific to Bone Specific Alkaline Phosphatase (BAP).

The term "serum Alkaline Phosphatase" as used herein refers to the level of Alkaline Phosphatase in blood serum as measured enzymatically using a Roche Modular Analyzer. In the presence of magnesium and zinc ions, p-nitrophenyl phosphate is cleaved by phosphatase into phosphate and p-nitrophenol. The p-nitrophenol released is proportional to the Alkaline Phosphatase activity and is measured photometrically.

The term "serum N-terminal Propeptide of Type I Collagen (PINP)" as used herein refers to the level of PINP in blood serum as measured using a sandwich principle, electrochemiluminescence immunoassay (ECLIA) on a Cobas e601 Analyzer. During the first incubation, PINP in the sample and a biotinylated monoclonal PINP-specific antibody are incubated together. During the second incubation, streptavidin-coated labelled microparticles and a monoclonal PINP-specific antibody labelled with ruthenium complex (Trs (2,2-bipyridyl)ruthenium (II)-complex (Ru(bpy)23+)) are added to form a sandwich complex, which binds to the solid phase via interaction of biotin and streptavidin. The reaction mixture is aspirated into the measuring cell where the microparticles are magnetically captured onto the surface of the electrode. A voltage is applied to the electrode, which induces chemiluminescent emission, which is measured by a photomultiplier. Results are determined via a calibration curve, which is instrument-specifically generated by a 2-point calibration and a master curve provided via the reagent barcode.

The term "serum Carboxy-terminal Collagen Crosslinks (CTx)" as used herein refers to the level of CTx in blood serum as measured using a sandwich principle, electrochemiluminescence immunoassay (ECLIA) on a Cobas e601 Analyzer. During the first incubation, 50 µL of sample and biotinylated monoclonal anti-beta-CrossLaps antibodies are incubated together. During the second incubation, streptavidin-coated labelled microparticles and a monoclonal P-beta-CrossLaps-specific antibody labelled with ruthenium complex are added to form a sandwich complex, which binds to the solid phase via interaction of biotin and streptavidin. The reaction mixture is aspirated into the measuring cell where the microparticles are magnetically captured onto the surface of the electrode. Unbound substances are then removed with ProCell. A voltage is applied to the electrode, which induces chemiluminescent emission, which is measured by a photomultiplier. Results are determined via a calibration curve, which is instrument-specifically generated by a 2-point calibration and a master curve provided via the reagent barcode.

The term "serum creatine kinase (CK)" as used herein refers to the CK level in blood serum as measured enzymatically using a Roche Modular and Cobas Analyzers. CK catalyzes the phosphorylation of ADP by creatine phosphate. ATP is performed which phosphorylates glucose and the resulting glucose-6-phosphate converts NADP+ to NADPH. The rate of NADPH formation is proportional to CK activity and is measured photometrically. CK is an enzyme that catalyzes the reversible transfer of phosphate from ATP to Creatine. This makes possible the storage of high-energy phosphate in a more stable form in ATP. CK is present in high concentration in skeletal muscle, cardiac muscle, thyroid, prostate and brain; it is present only in small amounts in liver, kidney, lung and other tissues. Hence, an increase in serum CK activity is ascribed primarily to damage to striated muscle (skeletal or cardiac) and in rare cases, to brain. Differentiation of these various diseases can frequently be made upon clinical grounds, but there are situations when this is not possible. Measurement of CK isoenzymes helps solve the problem.

The term "serum Ferritin" as used herein refers to the level of Ferritin in blood serum as measured using a two-site immunoenzymatic ("sandwich" assay). Ferritin is the major iron storage protein for the body. The concentration of ferritin is directly proportional to the total iron stores of the body, resulting in serum ferritin levels becoming a common diagnostic tool in the evaluation of iron status. Patients with iron deficiency anemia have serum ferritin levels approximately one tenth of normal subjects, while patients with iron overload (hemochromatosis, hemosiderosis) have serum ferritin level much higher than normal. Ferritin levels also provide a sensitive means of detecting iron deficiency at an early stage. In both adults and children, chronic inflammation results in a disproportionate increase in ferritin levels in relation to iron reserves. Elevated ferritin levels also are observed in acute and chronic liver disease, chronic renal failure and in some types of neoplastic disease.

It is noted that while the above blood parameters are determined in serum, they can likewise be determined in plasma. Serum and plasma levels correlate and can be converted into each other.

The term "bariatric surgery" as used herein refers to a surgical procedure aiming at introducing weight loss by reducing the size of the stomach with a gastric band or removal of a portion of the stomach (sleeve gastrectomy or biliopancreatic diversion with duodenal switch) or by resecting and re-routing the small intestine to a small stomach pouch.

"Obesity" is a condition characterized by excessive body weight to the extent when the body mass index (BMI), a measurement obtained by dividing a person's weight by the square of the person's height, is over 30 kg/m$^2$.

"Cardiac conditions with increased risks of arrhythmias" are conditions characterized by cardiovascular conditions and risk factors that increase the chance of developing arrhythmias, or abnormal heart rhythms including but not limited to: Coronary artery disease, endocarditis, valvular heart disease, high blood pressure, diabetes and obesity.

"Primary or secondary hyperparathyroidism" is a condition characterized by excessive secretion of parathyroid hormone.

"Asthma" is a condition characterized by a chronic lung disease that inflames and narrows the airways and causes recurring periods of wheezing, chest tightness, shortness of breath, and coughing.

"Chronic obstructive pulmonary disease (COPD)" is a condition characterized by a chronic inflammatory lung disease that causes obstructed airflow from the lungs.

"X-linked hypophosphatemia" is a condition characterized by a hereditary renal phosphate-wasting disorder characterized by low levels of phosphate in blood, rickets and/or osteomalacia, and diminished growth.

"Autosomal dominant or recessive hypophosphatemic rickets" is a condition characterized by bones that become soft and bend easily, due to low levels of phosphate in the blood.

"Secondary hypophosphatemia" is a condition characterized by low levels of phosphate in blood due to decreased oral intake or decreased intestinal absorption.

"Tumor induced hypophosphatemia" is a condition characterized by low levels of phosphate in blood secondary to tumor, such as FGF23 producing tumors.

"Osteoporosis" is a condition characterized by a bone disease that occurs when the body loses too much bone, makes too little bone, or both. As a result, bones become weak.

"Osteomalacia" is a condition characterized by the softening of the bones caused by impaired bone metabolism primarily due to inadequate levels of available phosphate, calcium, and vitamin D, or because of resorption of calcium. The impairment of bone metabolism causes inadequate bone mineralization.

A subject "being scheduled for surgery within 1 day to two months of the iron administration" is a subject who will have surgery within 1 day to two months of the iron administration.

For the purpose of this text, when specifying a dose in mg or g of an iron carbohydrate complex, consistent with the practice in the literature, the value refers to the amount of elemental iron provided in mg.

A. Therapeutic Methods

Described herein are therapeutic methods of treating iron deficiency which comprise administering ferric carboxymaltose according to defined administration regimens and/or to selected subgroups of subjects. Accordingly, the present invention also relates to ferric carboxymaltose for use in said methods, the use of ferric carboxymaltose for treating iron deficiency and or the use of ferric carboxymaltose in the manufacture of a medicament for treating iron deficiency.

I. Administration Regimens

According to a first embodiment of this aspect of the invention, the method of treating iron deficiency comprises repeated administration of the iron carbohydrate complex, in particular FCM, which is characterized in that the time between the first and the second dose is at least 10 days. For instance, if the first dose is administered at day 0, the second dose is administered at day 10 or thereafter. Preferably, the time between the first and the second dose is at least 14 days, 18 days, 21 days, 28 days, 35 days, 42 days, 49 days, or 56 days. In some cases, it can even be expedient that the time between the first and the second dose is at least 3 months or 6 months.

The daily dose of elemental iron administered is a therapeutically effective amount that may be in the range of 500 mg to 1000 mg, e.g. at 500 mg, 750 mg, or 1000 mg elemental iron.

The dose is in particular a single daily dose. For instance, a typical single daily dose of ferric carboxymaltose is 500 mg, 750 mg or 1000 mg elemental iron. For repeated administration, a first dose of 750 mg elemental iron is followed by a second dose of 750 mg elemental iron, or a first dose of 1000 mg elemental iron is followed by a second dose of 500 mg to 1000 mg of elemental iron, e.g. 500 mg, 750 mg or 1000 mg of elemental iron. Further doses of FCM may follow.

According to a second embodiment of this aspect of the invention, the method of treating iron deficiency comprises repeated administration of the iron carbohydrate complex, in particular FCM, which is characterized in that each of the first and the second dose does not exceed, or is less than, 500 mg of elemental iron. Exemplary amounts include 500 mg, 400 mg, 300 mg, 200 mg and 100 mg.

According to a third embodiment of this aspect of the invention, the method of treating iron deficiency comprises the administration of the iron carbohydrate complex, in particular FCM, which is characterized in that the total amount of elemental iron administered within a period of 12 months does not exceed 5000 mg. Preferably, the total amount of elemental iron administered within a period of 12 months does not exceed 4000 mg, 3000 mg or 2000 mg.

II. Selected Subgroups of Subjects

The methods of the invention are typically performed on a subject in need thereof. A subject in need of the methods of the invention is a subject having, diagnosed with, suspected of having, or at risk for developing iron deficiency, in particular, iron deficiency associated with chronic blood loss, acute blood loss, pregnancy, childbirth, lactation, childhood development, heavy uterine bleeding, menstruation, gastrointestinal bleeding, chronic internal bleeding, inflammatory bowel disease, congestive heart failure, restless leg syndrome, parasitic infections, lost or impaired kidney function such as due to chronic kidney disease or kidney failure, dialysis, surgery, chronic ingestion of agents such as alcohol, salicylates, steroids, non-steroidal anti-inflammatory agents, erythropoiesis stimulating agents (ESAs) or drugs inhibiting iron absorption. Iron deficiency anemia (IDA) develops when iron stores are depleted. Patients who suffer from ID may have IDA; patients with IDA necessarily suffer from ID. Methods to diagnose ID an IDA are well established in the art and commonly used in clinical practice.

Subjects having, diagnosed with, suspected of having, or at risk for developing iron deficiency will be given IV iron in the form of an iron carbohydrate complex, in particular ferric carboxymaltose, if oral iron is not tolerated or not effective in the subject. Another situation where IV iron is indicated is a need to deliver iron rapidly.

A particular group of subjects that are amenable to treatment according to the present invention is characterized as having a reduced risk for FGF23-mediated side effects.

According to a first embodiment of this aspect of the invention, a subject having a reduced risk for FGF23-mediated side effects has a blood or urine parameter selected from the group consisting of:

(1) normal serum phosphate level, in particular >2.5 mg/dL;

(2) normal serum vitamin D level, in particular 1,25-dihydroxyvitamin D being within the following ranges: Males: <16 years: 24-86 pg/mL, ≥16 years: 18-64 pg/mL, Females: <16 years: 24-86 pg/mL, ≥16 years: 18-78 pg/mL;

(3) normal serum ionized calcium level, in particular 1.16-1.32 mmol/L;

(4) normal serum PTH level, in particular 15-65 pg/mL;

(5) normal fractionary urinary phosphate excretion, in particular an FEPi of 10-20% (0.1-0.2 fraction); and (6) a combination of (1), (2), (3), (4), and (5).

According to a second embodiment of this aspect of the invention, a subject having a reduced risk for FGF23-mediated side effects has a blood parameter selected from the group consisting of:

(1) normal serum Bone Specific Alkaline Phosphatase level, in particular 6.5-22.4 U/L;

(2) normal serum Alkaline Phosphatase level, in particular 31-140 U/L;

(3) normal serum N-terminal Propeptide of Type I Collagen (PIMP) level, in particular 15.13-85.50 ng/mL;

(4) normal serum Carboxy-terminal Collagen Crosslinks (CTx) level, in particular 0.03-1.01 ng/mL; and (5) a combination of (1), (2), (3) and (4).

According to a third embodiment of this aspect of the invention, a subject having a reduced risk for FGF23-mediated side effects is characterized by the absence of one or more and in particular all of the following exclusion criteria:
(1) having undergone bariatric surgery;
(2) obesity;
(3) cardiac conditions with increased risks of arrhythmias;
(4) primary or secondary hyperparathyroidism;
(5) pulmonary disorders such as asthma or chronic obstructive pulmonary disease (COPD)
(6) genetic diseases leading to hypophosphatemia such as X-linked hypophosphatemia, autosomal dominant hypophosphatemic rickets, autosomal recessive hypophosphatemic rickets;
(7) secondary hypophosphatemia or tumor induced hypophosphatemia;
(8) disorders of the bone, such as for example osteoporosis or osteomalacia; and
(9) being scheduled for surgery within 1 day to two months of the iron administration such as preferably being scheduled for surgery within 1 to 3 weeks of iron administration.

According to a fourth embodiment of this aspect of the invention, a subject having a reduced risk for FGF23-mediated side effects is characterized by normal respiratory capacity measured as maximal respiratory pressure and maximal inspiratory pressure, in particular a maximal respiratory pressure of: Males: ≥117−(0.83×age) cm $H_2O$, Females: ≥95−(0.57×age) cm $H_2O$; and/or a maximal inspiratory pressure of: Males: ≥62−(0.15×age) cm $H_2O$, Females: ≥62−(0.50×age) cm $H_2O$.

According to a fifth aspect, a subject having a reduced risk for FGF23-mediated side effects has both blood/urine parameters as disclosed herein and is characterized by the absence of exclusion criteria as disclosed herein.

According to a sixth aspect, a subject having a reduced risk for FGF23-mediated side effects has blood/urine parameters as disclosed herein, is characterized by the absence of exclusion criteria as disclosed herein, and is characterized by normal respiratory capacity as disclosed herein.

A further particular group of subjects that are amenable to treatment according to the present invention are subjects with chronic kidney disease (CKD). Frequencies of hypophosphatemia following iron treatment are much lower in patients with chronic kidney disease (CKD), who have impaired renal function and thus impaired ability to excrete phosphate in the urine and as a result tend to rather suffer from hyperphosphatemia (too high phosphate). On the other hand, due to the tendency towards hyperphosphatemia, CKD patients tend to have very high FGF23 levels function due to ongoing attempts of the body to compensate for the high serum phosphate levels by producing iFGF23 to increase the urinary fractional excretion of phosphate via the kidneys. For this reason, iFGF23 levels are elevated in CKD patients, and as a result other downstream effects of iFGF23 may be more pronounced despite the lower risk of hypophosphatemia.

B. Diagnostic Methods

Further described herein are methods of monitoring a subject who has been administered a first dose of an iron carbohydrate complex, comprising determining in a biological sample obtained from the subject at least one blood or urine parameter selected from the group consisting of (1) serum phosphate level, (2) serum vitamin D level, (3) serum ionized calcium level, (4) serum PTH level and (5) fractionary urinary phosphate excretion, wherein the subject is eligible for being administered a second dose of the iron carbohydrate complex if the at least one blood or urine parameter is as disclosed herein.

Further described herein are methods of monitoring a subject who has been administered a first dose of ferric carboxymaltose, comprising determining in a biological sample obtained from the subject at least one blood parameter selected from the group consisting of (1) serum Bone Specific Alkaline Phosphatase level; (2) serum Alkaline Phosphatase level, (3) serum N-terminal Propeptide of Type I Collagen (PINP) level and (4) serum Carboxy-terminal Collagen Crosslinks (CTx) level, wherein the subject is eligible for being administered a second dose of ferric carboxymaltose if the at least one blood parameter is normal as disclosed herein.

Still further described herein are methods of monitoring a subject who has been administered a first dose of ferric carboxymaltose, comprising determining the respiratory capacity of the subject, wherein the subject is eligible for being administered a second dose of ferric carboxymaltose if the respiratory capacity is normal as disclosed herein.

Also described herein are methods of identifying a subject suitable for the therapeutic methods of the invention. Such methods include methods of identifying a subject having a reduced risk for FGF23-mediated side effects, comprising determining in a biological sample obtained from the subject at least one blood or urine parameter selected from the group consisting of (1) serum phosphate level, (2) serum vitamin D level, (3) serum ionized calcium level, (4) serum PTH level and (5) fractionary urinary phosphate excretion, wherein the subject has a reduced risk for FGF23-mediated side effects if the at least one blood or urine parameter is normal as disclosed herein.

Further described herein are methods of identifying a subject having a reduced risk for FGF23-mediated side effects, comprising determining in a biological sample obtained from the subject at least one blood parameter selected from the group consisting (1) serum Bone Specific Alkaline Phosphatase level; (2) serum Alkaline Phosphatase level, (3) serum N-terminal Propeptide of Type I Collagen (PINP) level and (4) serum Carboxy-terminal Collagen Crosslinks (CTx) level, wherein the subject has a reduced risk for FGF23-mediated side effects if the at least one blood or urine parameter is normal as disclosed herein.

Still further described herein are methods of identifying a subject having a reduced risk for FGF23-mediated side effects, comprising determining whether the subject is characterized by one or more and in particular all of the following exclusion criteria:
(1) having undergone bariatric surgery;
(2) obesity;
(3) cardiac conditions with increased risks of arrhythmias;
(4) primary or secondary hyperparathyroidism;
(5) pulmonary disorders such as asthma or chronic obstructive pulmonary disease (COPD)
(6) genetic diseases leading to hypophosphatemia such as X-linked hypophosphatemia, autosomal dominant hypophosphatemic rickets, autosomal recessive hypophosphatemic rickets;
(7) secondary hypophosphatemia or tumor induced hypophosphatemia;
(8) disorders of the bone, such as for example osteoporosis or osteomalacia; and
(9) being scheduled for surgery within 1 day to two months of the iron administration, wherein the subject has a reduced risk for FGF23-mediated side effects if the subject is characterized by the absence of one or more and in particular all of the exclusion criteria.

And yet described herein are methods of identifying a subject having a reduced risk for FGF23-mediated side effects, comprising determining the respiratory capacity of the subject, wherein the subject has a reduced risk for FGF23-mediated side effects if the respiratory capacity is normal as disclosed herein.

The biological sample can be any sample obtained from a subject, wherein the sample allows determining said blood or urine parameters. In some embodiments, the biological sample comprises a blood sample. In some embodiments, the biological sample comprises a plasma sample. In preferred embodiments, the biological sample comprises a serum sample. In other preferred embodiments, the biological sample comprises a urine sample. As the diagnostic methods are performed on a sample of the subject, the methods are carried out ex vivo, in particular in vitro.

The biological sample can be collected and/or obtained by any method known in the art. In some embodiments, the biological sample is obtained directly from a subject, e.g., by withdrawing the sample directly from the circulatory system of a subject. In other embodiment, the biological sample is obtained from a lab, wherein the lab, or a predecessor, previously obtained the biological sample directly from a subject. In some embodiments, the biological sample is fresh, e.g., the sample has not been frozen or stored for an extended period of time. In other embodiments, the biological sample has been stored at a temperature less than 37° C.

The diagnostic methods of monitoring and identifying a subject according to the invention, in some embodiments, further comprises administering the iron carbohydrate complex, in particular ferric carboxymaltose, to a subject identified as being eligible of being administered a second dose of the iron carbohydrate complex and/or as having a reduced risk for FGF23-mediated side effects. The disclosure herein in relation to the administration regimens and selected subgroups of patients is applicable in this regard.

C. Drug Combinations

Further described herein are combinations of FCM with one or more additional drugs for use in treating iron deficiency, wherein the additional drug is selected from the group consisting of:
 (1) vitamin Ds;
 (2) phosphates; and
 (3) anti-FGF23 antagonistic antibodies.

FCM leads to a decrease in active vitamin D, 1,25-dihydroxyvitamin D, and to an increase of 24,25-dihydroxyvitamin D. Administering therapeutically effective amounts of vitamin D can help reducing this effect. To this end, administration of alfacalcidol and in particular calcitriol is preferred. Alternatively, cholecalciferol or ergocalciferol may be administered.

If alfacalcidol or calcitriol is administered it may be administered within three days prior to the administration of the first FCM dose. Alternatively, alfacalcidol or calcitriol administration is started on the same day of first FCM dose. Still a further alternative is to start alfacalcidol or calcitriol administration on day 1, day 2, day 3, day 4, day 5, day 6 or day 7, or day 14 after the administration of the first FCM dose.

Calcitriol is expediently administered in a daily dose of 0.125 µg to 2 µg, such as 0.125 µg to 1 µg, such as 0.25 µg-0.75 µg, for example 0.50 mg.

Alfacalcidol is expediently administered in daily doses of 0.25 µg to 5 µg, such as 0.5 µg to 2 µg, such as 1 mg.

Whether administered as pre-treatment to FCM administration or subsequent to FCM administration, treatment with calcitriol or alfacalcidol is continued for until blood parameters, in particular vitamin D level, are normal or until three weeks, four weeks, five weeks, or six weeks after initiation of treatment, whichever occurs earlier.

Cholecalciferol or ergocalciferol is preferably administered prior to treatment with FCM, such as for a period of 14 days, 7 days, 6 days, alternatively 5 days, 4 days, 3 days, 2 days, 1 day prior to administration of the first FCM dose.

Cholecalciferol is expediently administered in weekly doses from 140 µg to 2500 µg, such as preferably 300 µg-600 µg such as preferably 500 pg.

Ergocalciferol is expediently administered in daily doses of 10 µg to 1250 µg, such as preferably 500 µg.

In one embodiment of the invention, the pre-treatment with either cholecalciferol or ergocalciferol prior to administration of the first FCM dose as disclosed herein is followed by treatment with alfacalcidol or calcitriol subsequent to administration of the first FCM dose as disclosed herein.

Because FCM also leads to a decrease in serum phosphate, administering therapeutically effective amounts of phosphates can help reducing this effect. For example, glucose-1-phosphate or a phosphate salt such as calcium phosphate, potassium phosphate or sodium phosphate can be administered orally or intravenously (IV).

Therapeutically effective amounts of phosphate for IV administration include single doses, preferably singly daily doses, of 10 mmol to 50 mmol, such as 30 mmol to 40 mmol and, in particular, 15 mmol to 35 mmol of phosphate, which may be repeated until serum phosphate have normalized.

Therapeutically effective amounts of phosphate for oral administration include single doses, preferably singly daily doses, of 15 mmol to 85 mmol, such as 30 mmol to 65 mmol and, in particular, 45 mmol to 50 mmol of phosphate, which may be repeated until serum phosphate have normalized.

According to a particular embodiment of the invention, a combination of additional drugs is used. The combination of a vitamin D and a phosphate is a particularly preferred combination.

Anti-FGF23 antibodies are used to treat very rare diseases such as x-linked hypophosphatemia. The first such product to reach the market is burosumab. It is preferred that anti-FGF23 antibodies are used in patients experiencing very severe FGF23 mediated side effects following the administration of FCM such as serum phosphate levels below 1 mg/dL or iFGF23 levels which are increased by 100 pg/mL or more relative to baseline.

According to a preferred embodiment, the additional drug is administered orally. This is in particular expedient if the additional drug is a phosphate, such as glucose-1-phosphate calcium phosphate or sodium phosphate, or a vitamin D, such as calcitriol.

According to a particular embodiment, the additional drug is administered prior to the first dose of FCM administration. This is in particular expedient if the additional drug is cholecalciferol or ergocalciferol.

According to another particular embodiment, the additional drug is administered after the first dose but prior to the second dose of FCM administration. This is in particular expedient if the additional drug is calcitriol or alfacalcidol. If phosphates used as additional drugs, it is likewise preferred to administer them after the first dose of FCM administration.

Dosages for the additional drugs usually refer to amounts of drug administered to adults. Dosages for administration to infants may be adjusted accordingly.

EXEMPLARY EMBODIMENTS

1. A method of treating iron deficiency, which comprises administering a first dose and a second dose of ferric carboxymaltose, wherein the time between the first and the second dose is at least 10 days.

2. The method of embodiment 1, wherein the time between the first and the second dose is at least 14 days, 18 days, 21 days, 28 days, 35 days, 42 days, 49 days, or 56 days.

3. The method of embodiment 1, wherein the time between the first and the second dose is at least 3 months or 6 months.

4. The method of any one of embodiments 1-3, wherein the first and the second dose is a single daily dose.

5. The method of any one of embodiments 1-4, wherein the first dose is 750 mg of elemental iron and the second dose is 750 mg of elemental iron.

6. A method of treating iron deficiency, which comprises administering a first dose and a second dose of ferric carboxymaltose, wherein the first and the second dose each do not exceed, or are less than, 500 mg of elemental iron.

7. A method of treating iron deficiency, which comprises administering one or more doses of ferric carboxymaltose, wherein the total amount of elemental iron administered within a period of 12 months does not exceed 5000 mg.

8. A method of treating iron deficiency, which comprises administering ferric carboxymaltose to a subject, wherein the subject has a reduced risk for FGF23-mediated side effects.

9. The method of embodiment 8, wherein the subject having a reduced risk for FGF23-mediated side effects has a blood or urine parameter selected from the group consisting of:
(1) normal serum phosphate level, in particular >2.5 mg/dL;
(2) normal serum vitamin D level, in particular 1,25-dihydroxy vitamin D being within the following ranges: Males: <16 years: 24-86 pg/mL, ≥16 years: 18-64 pg/mL, Females: <16 years: 24-86 pg/mL, ≥16 years: 18-78 pg/mL;
(3) normal serum ionized calcium level, in particular 1.16-1.32 mg/dL;
(4) normal serum PTH level, in particular 15-65 pg/mL;
(5) normal fractionary urinary phosphate excretion, in particular an FEPi of 10-20% (0.1-0.2 fraction); and
(6) a combination of (1), (2), (3), (4) and (5).

10. The method of embodiment 8, wherein the subject having a reduced risk for FGF23-mediated side effects has a blood parameter selected from the group consisting of:
(1) normal serum Bone Specific Alkaline Phosphatase level, in particular 6.5-22.4 U/L;
(2) normal serum Alkaline Phosphatase level, in particular 31-40 U/L;
(3) normal serum N-terminal Propeptide of Type I Collagen (PINP) level, in particular 15.13-85.50 ng/mL;
(4) normal serum Carboxy-terminal Collagen Crosslinks (CTx) level, in particular 0.03-1.01 ng/mL; and
(5) a combination of (1), (2), (3) and (4).

11. The method of embodiment 8, wherein the subject having a reduced risk for FGF23-mediated side effects is characterized by the absence of one or more and in particular all of the following exclusion criteria:
(1) having undergone bariatric surgery;
(2) obesity;
(3) cardiac conditions with increased risks of arrhythmias;
(4) primary or secondary hyperparathyroidism;
(5) pulmonary disorders such as asthma or chronic obstructive pulmonary disease (COPD)
(6) genetic diseases leading to hypophosphatemia such as X-linked hypophosphatemia, autosomal dominant hypophosphatemic rickets, autosomal recessive hypophosphatemic rickets;
(7) secondary hypophosphatemia or tumor induced hypophosphatemia;
(8) disorders of the bone, such as for example osteoporosis or osteomalacia; and
(9) being scheduled for surgery within 1 day to two months of the iron administration.

12. The method of embodiment 8, wherein the subject having a reduced risk for FGF23-mediated side effects is characterized by normal respiratory capacity measured as maximal respiratory pressure and/or maximal inspiratory pressure, in particular a maximal respiratory pressure of: Males: ≥117−(0.83×age) cm $H_2O$, Females: ≥95−(0.57×age) cm $H_2O$; and/or a maximal inspiratory pressure of: Males: ≥62−(0.15×age) cm $H_2O$, Females: ≥62−(0.50×age) cm $H_2O$.

13. The method of any one of embodiments 1-7 for treating a subject having a reduced risk for FGF23-mediated side effects as defined in embodiments 8-12.

14. A method of monitoring a subject who has been administered a first dose of ferric carboxymaltose, comprising determining in a biological sample obtained from the subject at least one blood or urine parameter selected from the group consisting of (1) serum phosphate level, (2) serum vitamin D level, (3) serum ionized calcium level, (4) serum PTH level and (5) fractionary urinary phosphate excretion, wherein the subject is eligible for being administered a second dose of ferric carboxymaltose if the at least one blood or urine parameter is as defined in embodiment 9.

15. A method of monitoring a subject who has been administered a first dose of ferric carboxymaltose, comprising determining in a biological sample obtained from the subject at least one blood parameter selected from the group consisting of (1) serum Bone Specific Alkaline Phosphatase level; (2) serum Alkaline Phosphatase level, (3) serum N-terminal Propeptide of Type I Collagen (PINP) level and (4) serum Carboxy-terminal Collagen Crosslinks (CTx) level, wherein the subject is eligible for being administered a second dose of ferric carboxymaltose if the at least one blood parameter is as defined in embodiment 10.

16. A method of monitoring a subject who has been administered a first dose of ferric carboxymaltose, comprising determining the respiratory capacity of the subject, wherein the subject is eligible for being administered a second dose of ferric carboxymaltose if the respiratory capacity is normal.

17. A method of identifying a subject having a reduced risk for FGF23-mediated side effects, comprising determining in a biological sample obtained from the subject at least one blood or urine parameter selected from the group consisting of (1) serum phosphate level, (2) serum vitamin D level, (3) serum ionized calcium level, (4) serum PTH level and (5) fractionary urinary phosphate excretion, wherein the subject has a reduced risk for FGF23-mediated side effects if the at least one blood or urine parameter is as defined in embodiment 9.

18. A method of identifying a subject having a reduced risk for FGF23-mediated side effects, comprising determining in a biological sample obtained from the subject at least one blood parameter selected from the group consisting (1) serum Bone Specific Alkaline Phosphatase level; (2) serum Alkaline Phosphatase level, (3) serum N-terminal Propeptide of Type I Collagen (PINP) level and (4) serum Carboxy-terminal Collagen Crosslinks (CTx) level, wherein the subject has a reduced risk for FGF23-mediated side effects if the at least one blood parameter is as defined in embodiment 10.

19. A method of identifying a subject having a reduced risk for FGF23-mediated side effects, comprising determining whether the subject is characterized by one or more and in particular all of the following exclusion criteria:

(1) having undergone bariatric surgery;
(2) obesity;
(3) cardiac conditions with increased risks of arrhythmias;
(4) primary or secondary hyperparathyroidism;
(5) pulmonary disorders such as asthma or chronic obstructive pulmonary disease (COPD)
(6) genetic diseases leading to hypophosphatemia such as X-linked hypophosphatemia, autosomal dominant hypophosphatemic rickets, autosomal recessive hypophosphatemic rickets;
(7) secondary hypophosphatemia or tumor induced hypophosphatemia;
(8) disorders of the bone, such as for example osteoporosis or osteomalacia; and
(9) being scheduled for surgery within 1 day to two months of the iron administration, wherein the subject has a reduced risk for FGF23-mediated side effects if the subject is characterized by the absence of one or more and in particular all of said exclusion criteria.

20. A method of identifying a subject having a reduced risk for FGF23-mediated side effects, comprising determining the respiratory capacity of the subject, wherein the subject has a reduced risk for FGF23-mediated side effects if the respiratory capacity is normal.

21. A combination of ferric carboxymaltose with one or more additional drugs for use in the treatment of iron deficiency, wherein the additional drug is selected from the group consisting of:
(1) vitamin Ds;
(2) phosphates; and
(3) anti-FGF23 antagonistic antibodies.

22. The combination of embodiment 21, wherein the vitamin D is calcitriol, alfacalcidol, cholecalciferol or ergocalciferol.

23. The combination of embodiment 22, wherein calcitriol or alfacalcidol is administered within three days prior to the administration of the first FCM dose.

24. The combination of embodiment 22, wherein administration of calcitriol or alfacalcidol is started on the same day of first FCM dose.

25. The combination of embodiment 22, wherein calcitriol or alfacalcidol administration is started on day 1, day 2, day 3, day 4, day 5, day 6 or day 7, or day 14 after the administration of the first FCM dose.

26. The combination of embodiment 22, wherein cholecalciferol or ergocalciferol is administered for a period of 14 days, 7 days, 6 days, alternatively 5 days, 4 days, 3 days, 2 days, 1 day prior to administration of the first FCM dose.

27. The combination of embodiments 22, wherein cholecalciferol or ergocalciferol is administered prior to administration of the first FCM dose followed by treatment with calcitriol or alfacalcidol subsequent to administration of the first FCM dose.

28. The combination of any one of embodiments 21-27, wherein the additional drug is administered orally.

29. The combination of any one of embodiment 21-28, wherein the additional drug is administered prior to the second dose of ferric carboxymaltose administration.

30. The combination of embodiments 21-29, for use in a method of any one of embodiments 1-13.

The present disclosure is further illustrated by the following examples, which should not be construed as further limiting. The contents of all figures and all references, Genbank sequences, patents and published patent applications cited throughout this application are expressly incorporated herein by reference.

Examples

Two prospective randomized, open-label, comparative trials were performed comparing the incidence of hypophosphatemia in relation to treatment with iron isomaltoside ("IIM", tradename Monofer®, Monoferric®) and ferric carboxymaltose ("FCM", trade name Injectafer, Ferinject) in adult human subjects with iron deficiency anaemia.

Trial Design

The trial was a randomized, open-label, comparative trial. Subjects with Iron Deficiency Anaemia (IDA) were randomized 1:1 to one treatment course of one of the following treatments:
Group A: iron isomaltoside 1000 (Monofer®, Pharmacosmos, Holbæk, Denmark, termed iron isomaltoside in the following), 1000 mg at baseline
Group B: ferric carboxymaltose (Ferinject®/Injectafer®, Vifor Inc, Switzerland), 750 mg at baseline and day 7, cumulative dose: 1500 mg FCM was administered in two single doses of 750 mg of elemental iron one week apart according to its US label. Iron isomaltoside 1000 was administered as a single dose of 1000 mg of elemental iron.

Objectives

The primary objective of the trial was to compare the incidence of hypophosphatemia in subjects with IDA treated with iron isomaltoside or ferric carboxymaltose.

The secondary safety objective of the trial was to compare the effects of iron isomaltoside and ferric carboxymaltose treatment in subjects with IDA on the following:
(1) Incidence of severe hypophosphatemia
(2) Time with hypophosphatemia
(3) Proportion of subjects with hypophosphatemia at the last visit
(4) S-phosphate (absolute [Δ] and relative [%] changes)
(5) Fractional phosphate urinary excretion
(6) Intact Fibroblast Growth Factor 23 (iFGF23), C-terminal FGF23 (cFGF23), vitamin D (25, 1,25, 24,25), Parathyroid Hormone PTH), and ionized calcium
(7) Adverse Events (AEs) and biochemical safety parameters The secondary efficacy objective of the trial was to compare the effects of iron isomaltoside and ferric carboxymaltose treatment in subjects with IDA on Haemoglobin (Hb), s-ferritin, and Transferrin Saturation (TSAT).

In addition to the primary and secondary objectives, exploratory analyses on the effect of iron isomaltoside and ferric carboxymaltose were performed including the following
(1) Biochemical bone/muscle markers
(2) Muscle strength Endpoints The primary endpoint was the incidence of hypophosphatemia (defined as s-phosphate <2 mg/dL) at any time from baseline to day 35.

The secondary safety endpoints were the following:
Incidence of s-phosphate below 1.0 mg/dL at any time from baseline to day 35
Time with hypophosphatemia (i.e. time with s-phosphate <2.0 mg/dL) from baseline to day 35
Proportion of subjects with hypophosphatemia at day 35
Absolute [Δ] and relative [%] changes in s-phosphate from baseline to 1, 7, 8, 14, 21, and 35
Fractional phosphate urinary excretion at 1, 7, 8, 14, 21, and 35
Change in iFGF23, cFGF23, vitamin D (25, 1,25, 24,25), PTH, and ionized calcium from baseline to 1, 7, 8, 14, 21, and 35
Type and incidence of AEs
Serious or severe hypersensitivity reaction starting on or after the first dose of randomized treatment (i.e. treatment emergent). The hypersensitivity terms were defined as standardised Medical Dictionary for Regulatory Activities query (SMQ) terms.

In addition, physical examinations and measurements of vital signs, height, weight, electrocardiogram (ECG), and safety laboratory parameters were measured as part of standard safety assessments.

The secondary efficacy endpoints were the following:
Change in Hb, s-ferritin, and TSAT from baseline to day 1, 7, 8, 14, 21, and 35

The exploratory endpoints were the following:
Change in biochemical bone/muscle markers (serum N-terminal Propeptide of Type I Collagen (PINP), Carboxy-terminal Collagen Crosslinks (CTx), s-alkaline phosphatase (bone specific and total), and creatine kinase) from baseline to day 1, 7, 8, 14, 21, and 35
Change in fatigue symptoms from baseline to day 14 and 35 measured by the Functional Assessment of Chronic Illness Therapy (FACIT) Fatigue Scale
Change in QoL from baseline to day 14 and 35 measured by Short Form (SF)-36 questionnaire
Change in bone pain from baseline to day 14 and 35 measured on a Visual Analogue Scale (VAS)
Change in muscle strength from baseline to day 14 and 35 measured by grip strength
Change in upper and lower limb proximal muscle function from baseline to day 14 and 35 measured by the "1 kg arm lift" test and the "30 sec chair stand" test.
Change in respiratory muscles strength from baseline to day 14 and 35 measured by Maximal Inspiratory Pressure (MIP) and Maximal Expiratory Pressure (MEP)

Safety Assessments

The trial included the following safety assessments:
Measurements of s-phosphate (blood and urine), iFGF23, cFGF23, vitamin D (25, 1,25, 24,25), PTH, and ionized calcium
AEs will be collected and evaluated for relatedness, severity, seriousness, and expectedness. They will be reported to authorities and followed-up according to international and local requirements
Physical examinations, measurements of vital signs, ECG, height, weight, and safety laboratory parameters Efficacy Assessments The trial included the following efficacy assessments:
Hb, s-ferritin, TSAT, and s-iron Exploratory Assessments The exploratory assessments included the following:
Measurement of serum N-terminal PINP, CTx, s-alkaline phosphatase (bone specific and total), and creatine kinase
MIP and MEP Trial Duration and Number of Visits For the individual subject, duration of the trial was 5 weeks (including a 28 days screening period) and each subject attended 8 visits.

Subject Population

Subjects, who fulfilled the following eligibility criteria, were included.

Inclusion Criteria:

A subject will be eligible for inclusion in the trial if he/she fulfils the following criteria:
1. Men or women >18 years having IDA caused by different aetiologies* such as abnormal uterine bleeding, gastrointestinal diseases, cancer, bariatric procedures (gastric bypass operations), and other conditions leading to significant blood loss
2. Hb≤11 g/dL
3. Body weight >50 kg
4. S-ferritin ≤100 ng/mL
5. Estimated Glomerular Filtration Rate (eGFR) ≥65 mL/min/1.73 m$^2$
6. S-phosphate >2.5 mg/dL
7. Documented history of intolerance or unresponsiveness to oral iron therapy for at least one month* prior to trial enrolment
8. Willingness to participate and signing the Informed Consent Form (ICF)

*The aetiology (also if unknown) for IDA was documented in the medical history and verified in the source documents.
**The intolerance and non-response to oral iron treatment was documented with sign and symptoms in the medical history and verified in the source document.
***There was a documentation of intolerance or unresponsiveness to at least one month of prescribed oral iron therapy per investigator's judgment within the last 9 months and they would not be candidates for oral iron again.

Exclusion Criteria:

A subject was not eligible for inclusion in this trial if he/she fulfilled any of the following criteria:
1. Acute bleeding >500 mL within 72 hours
2. Anaemia predominantly caused by factors other than IDA according to Investigator's judgment
3. Hemochromatosis or other iron storage disorders
4. Known hypersensitivity reaction to any component of iron isomaltoside or ferric carboxymaltose
5. Previous serious hypersensitivity reactions to any IV iron compounds
6. Treatment with IV iron within the last 30 days prior to screening
7. Treatment with erythropoietin or erythropoietin-stimulation agents, red blood cell transfusion, radiotherapy, and/or chemotherapy within the last 30 days prior to screening
8. Received an investigational drug within the last 30 days prior to screening
9. Planned surgical procedure within the trial period
10. Alanine Aminotransferase (ALAT) and/or Aspartate Aminotransferase (ASAT) >3 times upper limit of normal (e.g. decompensated liver cirrhosis or active hepatitis)
11. Surgery under general anaesthesia within the last 30 days prior to screening
12. Any non-viral infection within the last 30 days prior to screening
13. Alcohol or drug abuse within the past 6 months
14. Untreated hyperparathyroidism
15. Kidney transplantation
16. Estimated life expectancy of <6 months or, for cancer patients, an Eastern Cooperative Oncology Group (ECOG) performance status >1
17. Conditions that interfere with the subject's ability to understand the requirements of the trial and/or presumable non-compliance
18. Any other laboratory abnormality, medical condition, or psychiatric disorders which, in the opinion of the Investigator, will put the subject's disease management at risk or may result in the subject being unable to comply with the trial requirements
19. Pregnant or nursing women. In order to avoid pregnancy, women of childbearing potential have to use adequate contraception (e.g. intrauterine devices, hormonal contraceptives, or double barrier method) during the whole trial period and 7 days after the last dosing A summary of the subject population included is provided in the following table:

|  | IDA04 | | IDA05 | |
| --- | --- | --- | --- | --- |
|  | Iron Isomaltoside | Ferric Carboxymaltose | Iron Isomaltoside | Ferric Carboxymaltose |
| Safety Analysis set (N, %) | 63 (100.0) | 60 (100.0) | 62 (100.0) | 57 (100.0) |
| Age (years) | | | | |
| Mean (SD) | 43.9 (10.4) | 46.3 (11.6) | 42.2 (12.9) | 43.1 (11.5) |
| Median | 44.0 | 45.5 | 41.0 | 44.0 |
| Min-Max | 25-74 | 27-77 | 19-79 | 20-76 |
| Sex (N, %) | | | | |
| Female | 61 (95.8) | 57 (95.0) | 58 (93.5) | 54 (94.7) |
| Male | 2 (3.2) | 3 (5.0) | 4 (6.5) | 3 (5.3) |
| Race (N, %) | | | | |
| White | 38 (60.3) | 38 (63.3) | 28 (45.2) | 29 (50.9) |
| Asian | 2 (3.2) | 1 (1.7) | | |
| Black or African American | 22 (34.9) | 19 (31.7) | 32 (51.6) | 27 (47.4) |
| Other | 1 (1.6) | 2 (3.3) | 2 (3.2) | 1 (1.8) |

Trial Treatment

The subjects were dosed with either one treatment course of iron isomaltoside (group A) or one treatment course of ferric carboxymaltose (group B) as described below.

Group A: iron isomaltoside was administered as a single IV infusion of 1000 mg at baseline diluted in 100 mL 0.9% sodium chloride and given over approximately 20 minutes (50 mg iron/min, cumulative dose: 1000 mg).

Group B: ferric carboxymaltose was administered as 750 mg infused over at least 15 minutes at baseline and day 7 (cumulative dose: 1500 mg).

No premedication (e.g. antihistamine or steroids) was allowed before administration of the trial drug. If the subject was in daily treatment for e.g. allergy or asthma this was not considered as "premedication" and could be continued.

Statistical Analyses

The primary endpoint, incidence of hypophosphatemia (defined as s-phosphate <2 mg/dL) at any time from baseline to day 35, was tabulated and exact 95% CI were estimated for each treatment group.

Iron isomaltoside was compared to ferric carboxymaltose by estimation of the risk difference and the associated 95% CI, adjusting for strata (type of underlying disease (women with IDA due to gynaecological blood losses; yes/no) and screening s-phosphate level (< or ≥3.5 mg/dL)) using the Cochran-Mantel-Haenszel method.

As to sensitivity, the treatment groups were compared between the treatment groups by a logistic regression model with treatment and type of underlying disease as factors and baseline s-phosphate as covariate and by Fisher's exact tests.

All subjects in the safety analysis set were included in the analysis. The first post-baseline phosphate measurement was taken at day 1; hence, very few missing values are expected. If there were subject(s), for whom no post-baseline phosphate measurement(s) were available, these subjects will be set as having s-phosphate <2 mg/dL in the primary analysis.

All the statistical analyses will be described in a statistical analysis plan.

Baseline Assessment

|  | IDA04 | | IDA05 | |
| --- | --- | --- | --- | --- |
|  | Iron Isomaltoside N (%) | Ferric Carboxymaltose N (%) | Iron Isomaltoside N (%) | Ferric Carboxymaltose N (%) |
| Disease stratum: IDA due to gynaecological blood losses | | | | |
| Yes | 41 (65.1) | 42 (70.0) | 44 (71.0) | 39 (68.4) |
| No | 22 (34.9) | 18 (30.0) | 18 (29.0) | 18 (31.6) |
| Disease stratum: Screening s-phosphate level | | | | |
| <3.5 mg/dL | 32 (50.8) | 33 (55.0) | 35 (56.5) | 32 (56.1) |
| ≥3.5 mg/dL | 31 (49.2) | 27 (45.0) | 27 (43.5) | 25 (43.9) |

Trial Assessments

Demographic and Baseline Assessments

Date of birth, gender, race, ethnicity, and smoking habits were collected. A current smoker was defined as a subject who had been smoking within the last 6 months.

Pregnancy Test

A urine pregnancy test was performed for all women of childbearing potential. The test was handled and interpreted by the site personnel.

Relevant Medical History

Relevant medical history was recorded. Changes in medical history were recorded at the subsequent visits during the trial (worsening of symptoms or diseases were recorded as AEs). The following was collected: disease and start and stop date. Except for underlying disorder causing IDA, start dates occurring >12 months before the enrolment into the trial were set as >12 months.

Concomitant Medication

If the subject was receiving any concomitant medication it was recorded at the baseline visit. Changes in concomitant medication were recorded in the subsequent visits during the trial. The following was collected: brand name, indication, route, dose, frequency, unit, and start and stop date. Start dates occurring >12 months before the enrolment into the trial were set as >12 months.

Physical Examination

A physical examination was performed based upon the Investigator's judgement and could include the following:

Head-Eyes-Ear-Nose-Throat
Cardiovascular system
Respiratory system
Nervous system
Gastrointestinal system
Musculo-skeletal system
Urogenital system
Dermatology system
Others, if required Height Height was measured without shoes.

Weight

Weight was measured.

Vital Signs

Heart rate and blood pressure were measured at the following time points when a subject received trial drug: approximately 0-10 minutes before infusion, during infusion, 5-15 minutes, and 20-40 minutes after the infusion has ended. If vital signs were measured more than once in the given time interval, the lowest measurement of diastolic blood pressure (including the attendant systolic blood pressure and heart rate) for the period was noted in the electronic Case Report Form (eCRF).

Electrocardiogram

A standard 12 lead ECG was recorded (including date, time, and signature). At baseline and other treatment visits, two ECGs were recorded; one before administration of the trial drug and one approximately 30 minutes after start of the dosing. Only one ECG was recorded at the follow-up visits.

The ECGs did not need to be evaluated by a cardiologist.

Respiratory Muscles Strength

The measurements of MIP and MEP provided a non-invasive clinical method for evaluating the strength of respiratory muscles, and it was the most widely used test to assess muscle pressures [ATS/ERS statement, 2002]. The MIP reflected the strength of the diaphragm and other inspiratory muscles, while the MEP reflects the strength of the abdominal muscles and other expiratory muscles. MIP and MEP were measured by MicroRPM (CareFusion Germany 234 GmbH, Hoechberg, Germany). Three tests were performed for both MIP and MEP with the highest value from the three tests taken as the achieved result.

Laboratory Assessments

It was requested that the blood samples were drawn before administering the trial drug, and, if possible, that they were drawn at the same time of the day at all visits in order to reduce any diurnal fluctuation in the parameters.

Laboratory assessments were performed at a central laboratory. A Laboratory Manual was provided to each site in which all laboratory procedures were described.

Eligibility Laboratory Assessments

The following eligibility laboratory assessments were performed:

Complete haematology set: Hb, leucocytes/White Blood Cells (WBC), erythrocytes/Red Blood Cells (RBC), haematocrit, platelets, neutrophil granulocytes, lymphocytes, monocytes, eosinophils, basophils, Mean Corpuscular Haemoglobin (MCH), Mean Corpuscular Volume (MCV), Mean Corpuscular Haemoglobin Concentration (MCHC), and reticulocyte count Biochemistry:
S-ferritin
S-phosphate
Alanine Aminotransferase (ALAT) and Aspartate Aminotransferase (ASAT)
C-reactive Protein (CRP)
Estimated Glomerular Filtration Rate (eGFR)
PTH Vitamin E Vitamin E was measured at baseline visit as part of the demographic data.

Safety Laboratory Assessments

The following safety laboratory assessments were analysed:

S-phosphate: inorganic phosphorous forms an ammonium phosphomolybdate complex having the formula $(NH_4)_3[PO_4](MoO_3)_{12}$ with ammonium molybdate in the presence of sulfuric acid. The complex was determined photometrically in the ultraviolet region (340 nm) of the spectrum using the Roche Modular and Cobas Analyzer.

iFGF23 and cFGF23: the human intact FGF23 was measured by the 2nd generation Elisa kit manufactured by Immonotropics, Inc, San Clemente, Calif. This was a two-site enzyme-linked immunosorbent assay. The human C-terminal FGF23 was measured by the Elisa kit manufactured by Immonotropics, Inc, San Clemente, Calif. This was a two-site enzyme-linked immunosorbent assay.

Vitamin D (25, 1,25, 24,25): Following protein precipitation, 25-hydroxyvitamin D2, 25-hydroxyvitamin D3 and their internal standards were extracted by supported liquid extraction (SLE). After evaporation under nitrogen, the residue was reconstituted and analyzed using Liquid Chromatography (LC) with Tandem Mass Spectrometric detection (MS/MS). The standard curve range was 0.5 ng/mL to 200.00 ng/mL using a serum volume of 0.1 mL.

PTH: The Intact PTH assay was performed using the iPTH reagent packs for the ADVIA Centaur XP instruments. The assay was a two-site sandwich immunoassay using direct chemiluminometric technology, which used constant amounts of two anti-human PTH antibodies in the Lite Reagent. The first antibody was a polyclonal goat anti-human PTH (N-terminal 1-34) antibody labeled with acridinium ester. The second antibody was a biotinylated polyclonal goat anti-human PTH (39-84 region) antibody. Streptavidin in the Solid Phase was covalently coupled to paramagnetic latex particles. A direct relationship exists between the amount of PTH present in the patient sample and the amount of relative light units (RLUs) detected by the system.

Ionized calcium: Measured by the IL GEM Premier 3500 PAK cartridge. The central component was the sensor card, which provided a low volume, gas tight chamber in which the sample was presented to the sensors. The pH and electrolyte sensors were all based on the principle of ion-selective electrodes; that is, an electrical potential could be established across a membrane which was selectively permeable to a specific ion. The pH and electrolyte sensors were polyvinyl chloride (PVC) based ion selective electrodes, consisting of an internal Ag/AgCl reference electrode and internal salt layer. The potentials were measured against the card reference electrode.

Complete haematology set: Leucocytes/WBC, erythrocytes/RBC, haematocrit, platelets, neutrophil granulocytes, lymphocytes, monocytes, eosinophils, basophils, MCH, MCV, MCHC, and reticulocyte count Biochemistry:
S-sodium, s-potassium, s-calcium, s-urea, s-creatinine, s-albumin
S-bilirubin, ASAT, ALAT
CRP Efficacy Laboratory Assessments The following efficacy laboratory parameters were analysed:
Hb
S-ferritin: The Access ferritin assay was a two-site immunoenzymatic ("sandwich" assay). A sample was added to a reaction vessel with goat anti-ferritin-alkaline phosphatase conjugate, and paramagnetic particles coated with goat anti-mouse: mouse anti-ferritin complexes. Serum or plasma (heparin) ferritin binds to the immobilized monoclonal anti-ferritin on the solid phase, while the goat anti-ferritin enzyme conjugate reacts with different antigenic sites on the ferritin molecules. Separation in a magnetic field and washing removed materials not bound to the solid phase. A chemiluminescent substrate, Lumi-Phos* 530, was added to the reaction vessel and light generated by the reaction was measured with a luminometer.
TSAT (s-iron and transferrin will be collected to calculate the TSAT)

Exploratory Laboratory Assessments

The following exploratory laboratory assessments were analysed:
Serum N-terminal PINP: The measurement method was a sandwich principle, electrochemiluminescence immunoassay (ECLIA). During the first incubation, PINP in the sample and a biotinylated monoclonal PINP-specific antibody were incubated together. During the second incubation, streptavidin-coated labelled microparticles and a monoclonal PINP-specific antibody labelled with a ruthenium complex (Trs (2,2-bipyridyl)ruthenium (II)-complex (Ru(bpy)23+)) were added to form a sandwich complex, which bound to the solid phase via interaction of biotin and streptavidin. The reaction mixture was aspirated into the measuring cell where the microparticles were magnetically captured onto the surface of the electrode. A voltage was applied to the electrode, which induced chemiluminescent emission, which was measured by a photomultiplier. Results were determined via a calibration curve, which was instrument-specifically generated by a 2-point calibration and a master curve provided via the reagent barcode. The method was run on a Cobas e601 Analyzer.
CTx: During the first incubation, 50 μL of sample and biotinylated monoclonal anti-beta-CrossLaps antibody were incubated together. During the second incubation, streptavidin-coated labelled microparticles and a monoclonal P beta-CrossLaps-specific antibody labelled with ruthenium complex were added to form a sandwich complex, which bound to the solid phase via interaction of biotin and streptavidin. The reaction mixture was aspirated into the measuring cell where the microparticles were magnetically captured onto the surface of the electrode. Unbound substances were then removed with ProCell. A voltage was applied to the electrode, which induced chemiluminescent emission, which was measured by a photomultiplier. Results were determined via a calibration curve, which was instrument-specifically generated by a 2-point calibration and a master curve provided via the reagent barcode. The method was run on a Cobas e601 Analyzer.

S-alkaline phosphatase (bone specific and total): Bone Specific Phosphatase (BAP) was measured on Beckman Dxi 800. The Beckman-Coulter Ostase assay was a one-step immunoenzymatic chemiluminescence assay. A mouse monoclonal antibody specific to Bone Specific Alkaline phosphatase (BAP) was added to a reaction vessels with paramagnetic particles coated with goat anti-mouse polyclonal antibody. Calibrators, controls, and samples containing BAP were added to the coated particles and bound to the anti-BAP monoclonal antibody. Chemiluminescent substrate, Lumi-Phos*530, was added to the reaction vessel and light generated by the reaction was measured with a luminometer. The light production is directly proportional to the amount of BAP in the sample. The amount of BAP in the sample was determined by means of a stored multi-point calibration curve. The level of total Alkaline Phosphatase in blood serum was measured using a Roche Modular Analyzer. In the presence of magnesium and zinc ions, p-nitrophenyl phosphate was cleaved by phosphatase into phosphate and p-nitrophenol. The p-nitrophenol released is proportional to the ALP activity and was measured photometrically.

Creatine kinase: The creatine kinase (CK) assay was performed on the Roche Modular and Cobas Analyzers. The reaction proceeded as follows:

Creatine phosphate+ADP CK>creatine+ATP
ATP+glucose HK>ADP+G-6-P
G-6-P+NADP+>G-6-PDH 6-PG+NADPH+H+

The formation of NADPH proceeded at the same rate as the formation of creatine in equimolar amounts. The rate of NADPH formation is proportional to CK activity and is measured photometrically.

Urine Assessments

A spot urine sampling was collected in order to assess the level of fractional s-phosphate excretion.

Adverse Events

AEs were collected and evaluated for relatedness to trial drug, seriousness, severity, and expectedness.

Results

Key findings include a clear impact of the FCM dosing regimen on the endocrine system managing phosphate, vitamin-D and calcium.

The rate of hypophosphatemia was significantly higher for FCM vs TIM, both in terms of the moderate to severe form with serum phosphate below 2 mg/dL and the severe form of serum phosphate at or below 1.0 mg/dL. See FIGS. 1 to 5.

Figure 6:
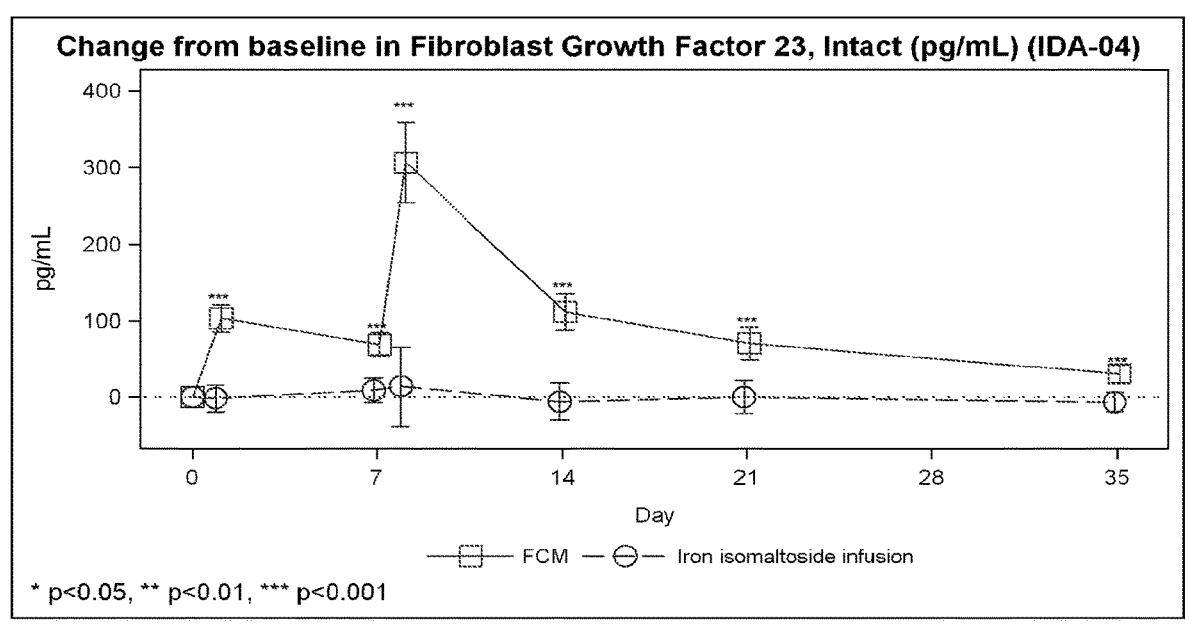
FIG. 6 shows the change in iFGF23 over time (IDA-04).
Figure 7:
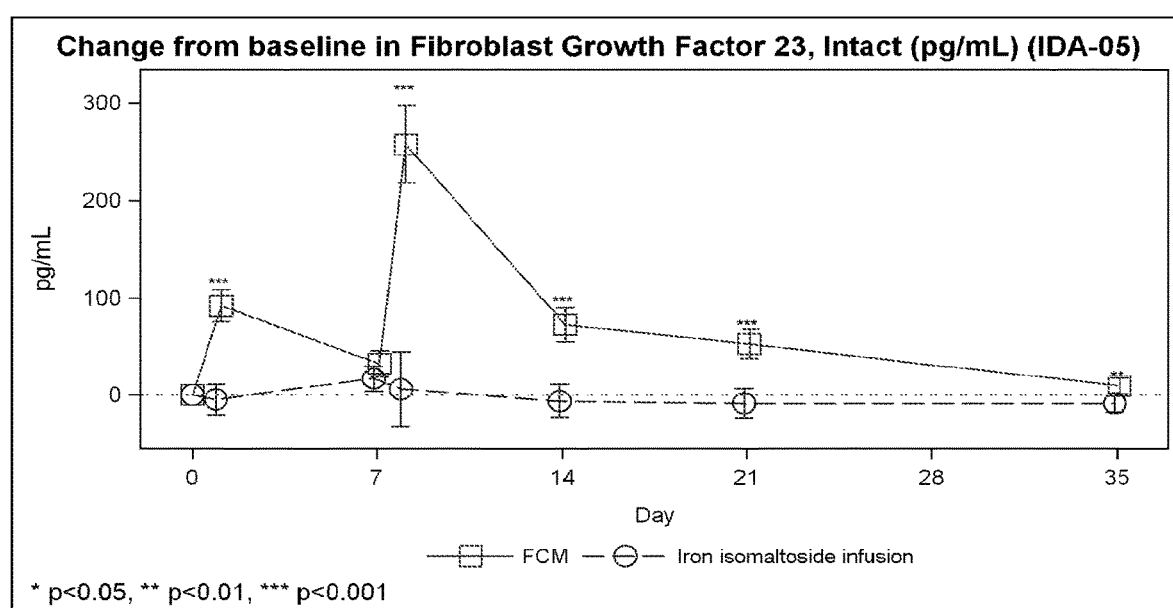
FIG. 7 shows the change in iFGF23 over time (IDA-05).
Figure 8:
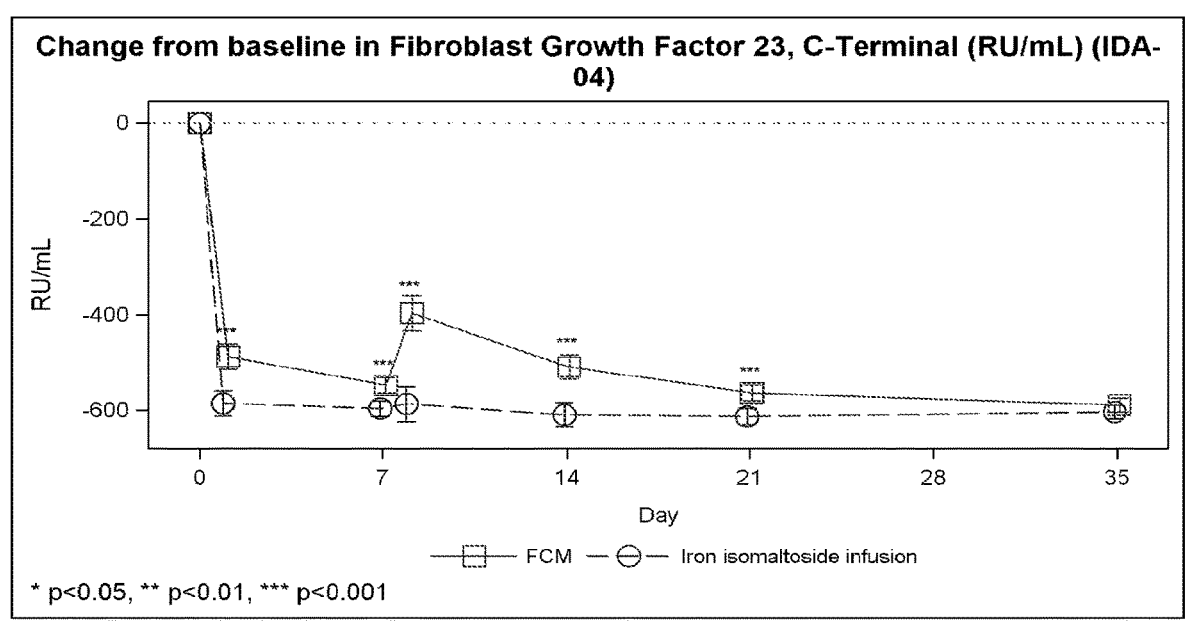
FIG. 8 shows the change in cFGF23 over time (IDA-04).
Figure 9:
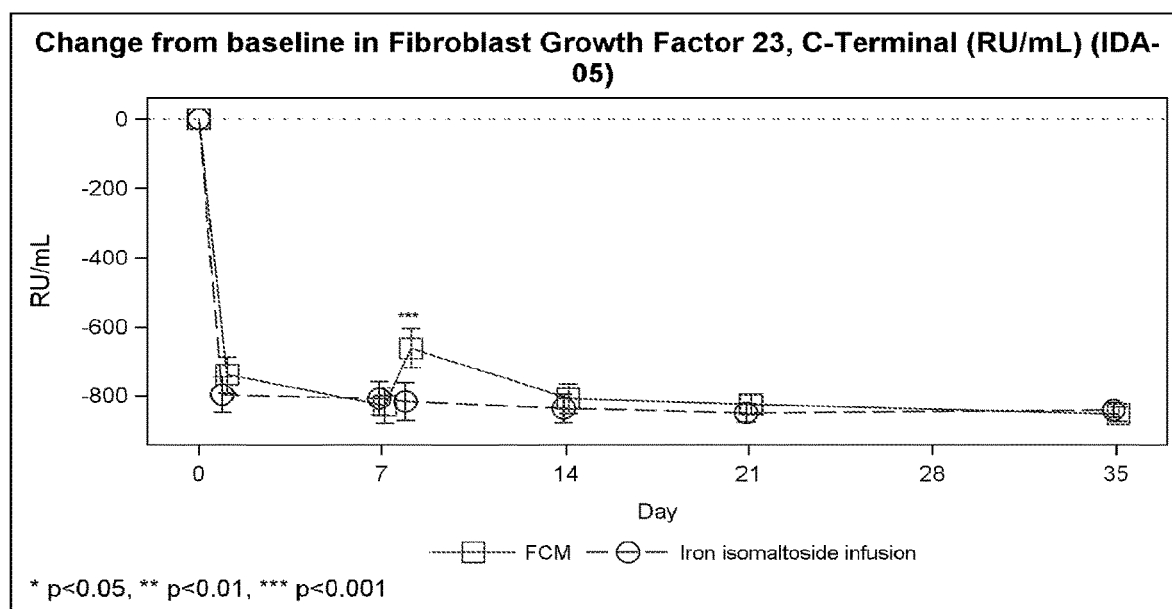
FIG. 9 shows the change in cFGF23 over time (IDA-05).
Figure 12:
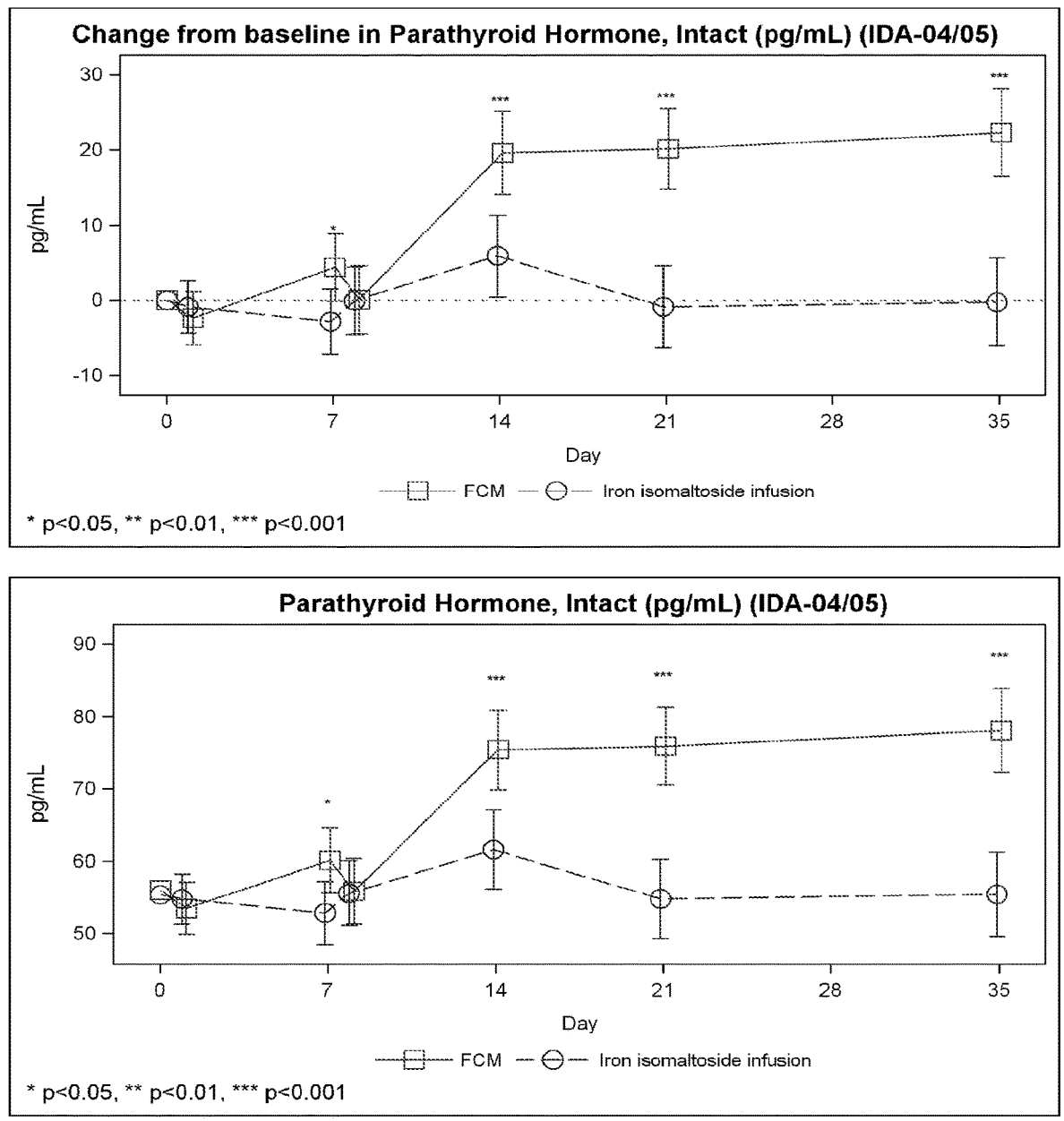
FIG. 12 shows the change from baseline and absolute change of intact parathyroid hormone levels over time (IDA-04 and IDA-05 combined).

Intact iFGF23 (iFGF23) increased sharply after administration of FCM and then gradually declined over a matter of days. On the second administration, iFGF23 again increased, but this time to a level several fold higher than the initial level, i.e. a surprising and previously unknown self-amplifying effect. For IIM essentially no change of the iFGF23 level was observed. See FIGS. 6 and 7. C-terminal FGF23 (cFGF23) which was initially high due to the underlying iron deficiency anemia dropped sharply on the first administration of FCM whereas it increased on the second administration of FCM. See FIG. 8. Fractional urinary excretion of phosphate was significantly increased for FCM vs IIM. See FIG. 10. FCM led to an increase in PTH, a decrease in 1,25-dihydroxyvitamin D, an increase in 24,25-dihydroxyvitamin D and a decrease in ionized calcium. See FIGS. 11 to 13.

Moreover, FCM led to the significant changes in bone turnover and muscle function as measured by the following biochemical bone/muscle markers.

Figure 14:
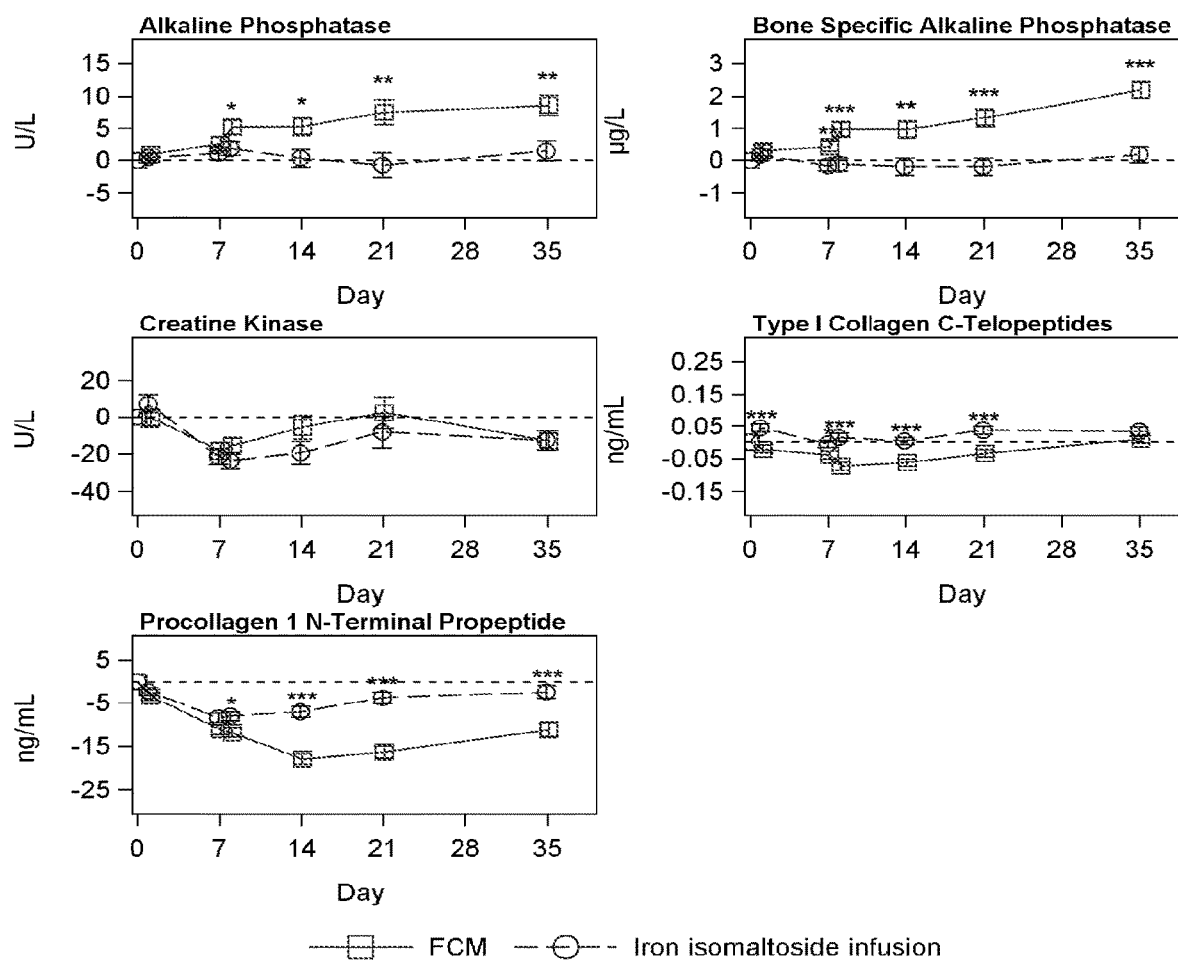
FIG. 14 shows the mean change of several makers of muscle function and bone turnover over time (IDA-04 and IDA-05 combined).

FCM induced a statistically significant increase of Bone Specific Alkaline Phosphatase compared to IMM. See FIG. 14.

FCM induced statistically significant lower N-terminal PINP values than IMM. See FIG. 14.

FCM induced a statistically significant lower CTx values than IMM. See FIG. 14.

FCM induced a statistically significant increase of Alkaline Phosphatase compared to IMM. See FIG. 14.

Figure 15:
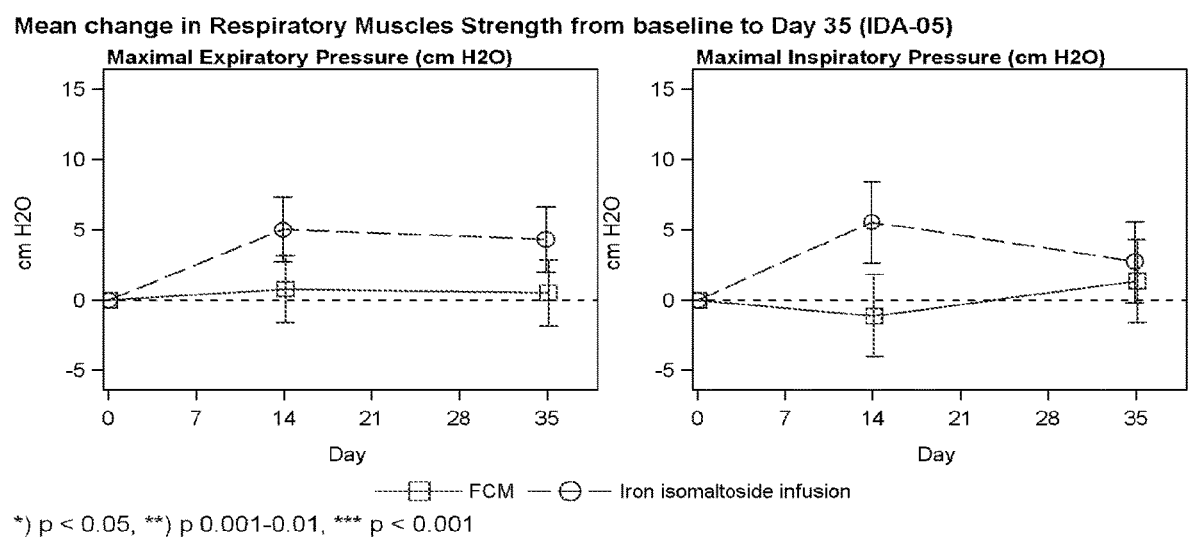
FIG. 15 shows the mean change in respiratory muscle strength over time (IDA-04 and IDA-05 combined).

FCM also lead to reduced muscle function relative to the comparator IV iron treatment as specifically measured through respiratory capacity measured as maximal respiratory pressure and/or maximal inspiratory pressure. See FIG. 15.

EQUIVALENTS

Those skilled in the art will recognize, or be able to ascertain using no more than routine experimentation, many equivalents of the specific embodiments disclosed herein. Such equivalents are intended to be encompassed by the following claims.

NON-PATENT PUBLICATIONS

Aksan et al., Aliment Pharmacol Ther 2017, 45(10), 1303-1318
Bager et al., Br J Clin Pharmacol 2017, 83, 1118-1125
Bregman et al., Ther Adv Hematol 2014, 5(2), 48-60
Charytan et al., Nephrol Dial Transplant 2013, 28, 953-964
Evstatiev, Gastroenterology 2011, 141, 846-853
Hussain et al., Anemia 2013, Article ID 169107, 10 pages
Ikuta et al., Int J Hematol 2018, https://doi.org/10.1007/s12185-018-2501-8
Klein et al. BMJ Case Rep 2018; doi:10.1136/bcr-2017-222851
Prats et al., BMC Nephrology 2013, 14:167
Qunibi et al., Nephrol Dial Transplant 2011, 26, 1599-1607
Sari et al., Neth J Med 2017, 75(2), 65-73
Schaefer et al., Gastroenterology 2017, 152(6), e5-e6
Seid et al., Am J Obstet Gynecol 2008, 199:435.e1-435.e7
Stein et al., Scand J Gastroenterol 2018, https://doi.org/10.1080/00365521.2018.1498914
Van Wyck et al., Transfusion 2009, 49(12), 2719-2728
Wolf et al., Journal of Bone and Mineral Research 2013, 28(8), 1793-1803
Zoller et al., Curr Opin Nephrol Hypertens 2017, 26(4), 266-275

The invention claimed is:

1. A method of treating iron deficiency in a human subject, which comprises administering a dose followed by a further dose of ferric carboxymaltose to the subject, wherein:
   a. the dose of ferric carboxymaltose contains 750 mg of elemental iron and the further dose of ferric carboxymaltose contains 750 mg of elemental iron; or
   b. the dose of ferric carboxymaltose contains 1000 mg of elemental iron and the further dose of ferric carboxymaltose contains in the range of 500 mg to 1000 mg of elemental iron,
wherein the subject has a reduced risk for hypophosphatemia, wherein the subject having a reduced risk for hypophosphatemia has a normal serum phosphate level.

2. The method of claim 1, wherein hypophosphatemia is low serum phosphate, optionally below 2 mg/dL.

3. The method of claim 1, wherein hypophosphatemia is symptomatic hypophosphatemia.

4. The method of claim 1, wherein iron deficiency is iron deficiency anemia.

5. The method of claim 4, wherein the subject has intolerance to oral iron or has had unsatisfactory response to oral iron.

6. The method of claim 4, wherein the subject has chronic kidney disease.

7. The method of claim 1, wherein the dose is administered as a single-dose treatment.

8. The method of claim 1, wherein the further dose is administered as a single-dose treatment.

9. The method of claim 1, wherein the subject requires a repeat course of treatment.

10. The method of claim 1, wherein iron deficiency is iron deficiency associated with heart failure.

11. The method of claim 1, wherein the normal serum phosphate level is >2.5 mg/dL.

12. The method of claim 1, wherein the subject having a reduced risk for hypophosphatemia further has a blood or urine parameter selected from the group consisting of:
   (1) normal serum vitamin D level;
   (2) normal serum parathyroid hormone (PTH) level; and
   (3) a combination of (1) and (2).

13. The method of claim 12, wherein the normal serum vitamin D level is a 1,25-dihydroxyvitamin D level within the following ranges: Males: <16 years: 24-86 pg/mL, ≥16 years: 18-64 pg/mL, Females: <16 years: 24-86 pg/mL, ≥16 years: 18-78 pg/mL.

14. The method of claim 12, wherein the normal serum PTH level is 15-65 pg/mL.

15. The method of claim 1, wherein the subject having a reduced risk for hypophosphatemia is characterized by the absence of one or more and in particular all of the risk factors:
   (1) primary or secondary hyperparathyroidism;
   (2) decreased intestinal absorption of phosphate; and
   (3) disorders of the bone, optionally osteoporosis or osteomalacia.

16. A method of monitoring serum phosphate level in a human subject who has been administered a dose of ferric carboxymaltose, comprising determining serum phosphate level in a biological sample obtained from the subject, wherein the subject is eligible for being administered a further dose of ferric carboxymaltose if the serum phosphate level is normal.

17. The method of claim 16, wherein the dose is administered as a single-dose treatment.

18. The method of claim 16, wherein the further dose is administered as a single-dose treatment.

19. The method of claim 16, wherein the subject requires a repeat course of treatment.

20. The method of claim 16, wherein the normal serum phosphate level is >2.5 mg/dL.

21. The method of claim 16, further comprising determining in the biological sample obtained from the subject at least one blood or urine parameter selected from the group consisting of (1) serum vitamin D level and (2) serum PTH level, wherein the subject is eligible for being administered a further dose of ferric carboxymaltose if:
   (1) serum vitamin D level is normal;
   (2) serum PTH level is normal; or
   (3) a combination of (1) and (2).

22. The method of claim 21, wherein the normal serum vitamin D level is a 1,25-dihydroxyvitamin D level within the following ranges: Males: <16 years: 24-86 pg/mL, ≥16 years: 18-64 pg/mL, Females: <16 years: 24-86 pg/mL, ≥16 years: 18-78 pg/mL.

23. The method of claim 21, wherein the normal serum PTH level is 15-65 pg/mL.

24. The method of claim 16, wherein the dose of ferric carboxymaltose contains 750 mg of elemental iron and the further dose of ferric carboxymaltose contains 750 mg of elemental iron, or the dose of ferric carboxymaltose contains 1000 mg of elemental iron and the further dose of ferric carboxymaltose contains in the range of 500 mg to 1000 mg of elemental iron.

25. The method of claim 16, wherein the subject has an increased risk for hypophosphatemia, wherein the subject having an increased risk for hypophosphatemia is characterized by one or more and in particular all of the following criteria:
(1) primary or secondary hyperparathyroidism;
(2) decreased intestinal absorption of phosphate; and
(3) disorders of the bone, optionally osteoporosis or osteomalacia.

26. A method of identifying a human subject for treatment with ferric carboxymaltose, wherein the subject has a reduced risk for hypophosphatemia, and the method comprises determining in a biological sample obtained from the subject serum phosphate level, wherein the subject has a reduced risk for hypophosphatemia if the serum phosphate level is normal.

27. The method of claim 26, wherein the subject requires a repeat course of treatment.

28. The method of claim 26, wherein the normal serum phosphate level is >2.5 mg/dL.

29. The method of claim 26, further comprising determining in the biological sample obtained from the subject at least one blood or urine parameter selected from the group consisting of (1) serum vitamin D level and (2) serum PTH level, wherein the subject has a reduced risk for hypophosphatemia if:
(1) serum vitamin D level is normal;
(2) serum PTH level is normal; or
(3) a combination of (1) and (2).

30. The method of claim 29, wherein the normal serum vitamin D level is a 1,25-dihydroxyvitamin D level within the following ranges: Males: <16 years: 24-86 pg/mL, ≥16 years: 18-64 pg/mL, Females: <16 years: 24-86 pg/mL, ≥16 years: 18-78 pg/mL.

31. The method of claim 29, wherein the normal serum PTH level is 15-65 pg/mL.

32. The method of claim 26, wherein the subject having reduced risk for hypophosphatemia is characterized by the absence of at least one or all of the following exclusion criteria:
(1) primary or secondary hyperparathyroidism;
(2) decreased intestinal absorption of phosphate; and
(3) disorders of the bone, optionally osteoporosis or osteomalacia.

33. The method of claim 1, wherein in step b., the dose of ferric carboxymaltose contains 1000 mg of elemental iron and the further dose of ferric carboxymaltose contains 500 mg, 750 mg or 1000 mg of elemental iron.

34. The method of claim 24, wherein the dose of ferric carboxymaltose contains 1000 mg of elemental iron and the further dose of ferric carboxymaltose contains 500 mg, 750 mg or 1000 mg of elemental iron.

* * * * *